US012557831B2

(12) United States Patent
Prakash et al.

(10) Patent No.: US 12,557,831 B2
(45) Date of Patent: Feb. 24, 2026

(54) MOGROSIDES AND USES OF THE SAME

(71) Applicant: The Coca-Cola Company, Atlanta, GA (US)

(72) Inventors: Indra Prakash, Alpharetta, GA (US); Gil Ma, Atlanta, GA (US); Christopher Mercogliano, Atlanta, GA (US); Goran Petrovic, Atlanta, GA (US)

(73) Assignee: The Coca-Cola Company, Atlanta, GA (US)

( * ) Notice: Subject to any disclaimer, the term of this patent is extended or adjusted under 35 U.S.C. 154(b) by 532 days.

(21) Appl. No.: 17/434,235

(22) PCT Filed: Feb. 26, 2020

(86) PCT No.: PCT/US2020/019864
§ 371 (c)(1),
(2) Date: Aug. 26, 2021

(87) PCT Pub. No.: WO2020/176602
PCT Pub. Date: Sep. 3, 2020

(65) Prior Publication Data
US 2022/0142216 A1 May 12, 2022

Related U.S. Application Data

(60) Provisional application No. 62/810,556, filed on Feb. 26, 2019.

(51) Int. Cl.

| | |
|---|---|
| ***A23L 27/30*** | (2016.01) |
| ***A23L 2/60*** | (2006.01) |
| ***C07J 17/00*** | (2006.01) |

(52) U.S. Cl.
CPC ................ *A23L 27/36* (2016.08); *A23L 2/60* (2013.01); *C07J 17/005* (2013.01); *A23V 2002/00* (2013.01)

(58) Field of Classification Search
CPC .......... A23L 27/36; A23L 2/60; C07J 17/005; C07H 15/24
See application file for complete search history.

(56) References Cited

U.S. PATENT DOCUMENTS

2017/0029458 A1 2/2017 Siems et al.
2019/0367961 A1* 12/2019 Ono .................... C12Y 204/01

FOREIGN PATENT DOCUMENTS

WO WO-2014086842 A1 * 6/2014 .......... C12N 9/0071
WO WO 2014/140634 9/2014
WO WO 2014/146089 9/2014
WO WO-2015082012 A1 * 6/2015 .............. A23G 3/36
(Continued)

OTHER PUBLICATIONS

Hikaru, Plant-derived isoprenoid sweeteners: recent progress in biosynthesis gene discovery and perspectives on microbial production, Biosci, Biotech. and Biochem,, 2018, 82, 6, 927-934 (Year: 2018).*

(Continued)

*Primary Examiner* — Changqing Li
(74) *Attorney, Agent, or Firm* — King & Spalding

(57) ABSTRACT

Mogrosides containing non-glucose glycosides are provided herein. Compositions, including consumables comprising the novel mogrosides described herein, are also provided.

11 Claims, 10 Drawing Sheets

(56) References Cited

FOREIGN PATENT DOCUMENTS

| | | | | | |
|---|---|---|---|---|---|
| WO | WO 2017/075257 | | 5/2017 | | |
| WO | WO-2018089469 | A1 * | 5/2018 | ............... | A23L 2/60 |
| WO | WO-2021152028 | A1 * | 8/2021 | ............. | A23F 3/163 |

OTHER PUBLICATIONS

International Search Report for PCT/US2020/019864, issued Jun. 24, 2020.

* cited by examiner

| Peak | Ret. Time | Area | Area% |
|---|---|---|---|
| 45 | 13.097 | 13973494 | 6.410 |
| 46 | 13.693 | 15989222 | 7.335 |
| 47+48 | 15.072 | 188018678 | 86.254 |
| Total | | 217981394 | 100.000 |

| Peak | Ret. Time | Area | Area% |
|---|---|---|---|
| 108 | 11.212 | 5027723 | 2.263 |
| 109 | 11.826 | 22754127 | 10.243 |
| 110 | 13.643 | 5168164 | 2.326 |
| 111+112 | 45.341 | 189199156 | 85.168 |
| Total | | 222149170 | 100.000 |

MOGROSIDES AND USES OF THE SAME

CROSS REFERENCE TO RELATED APPLICATION

This application is a national phase application under 35 U.S.C. § 371 of International Application No. PCT/US2020/019864, filed Feb. 26, 2020, which claims priority to U.S. Provisional Application No. 62/810,556, filed Feb. 26, 2019. The contents of each of the above-identified applications is hereby fully incorporated herein by reference.

FIELD OF THE INVENTION

The disclosure relates to mogroside compounds containing one or more non-glucose carbohydrates and methods for producing the same. More specifically, the disclosure relates to use of mogroside compounds containing one or more non-glucose carbohydrates as sweeteners in consumables.

BACKGROUND

Extracts of monk fruit obtained from *Siraitia grosvenori* (a plant of the Cucurbitaceae family) are commercially used as natural sweeteners. Yet, monk fruit extract may have taste characteristics that discourage their use as a replacement for caloric sweeteners (e.g., sugar) in food and beverage compositions. For example, the extracts may have certain off-flavors or a lingering aftertaste or may take longer than desired to develop a sweet taste after being consumed (i.e., a delayed onset of sweetness).

There remains a need for sweeteners with reduced calorie content having low or no calories having improved taste characteristics, as well as food and beverages containing the same.

SUMMARY

Typical mogrosides are characterized by glucose-containing glycosides at the C-3 and C24 position of the mogrol core. The present disclosure relates to novel mogroside compounds that contain at least one carbohydrate other than glucose in the glycosides at the C3 and C24 position.

In one aspect, the present invention provides a mogroside of Formula I:

Formula I

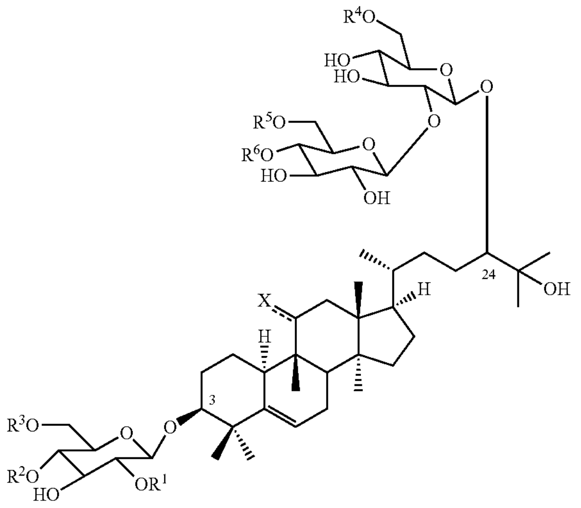

wherein:

when ⎓ is a double bond, X is O;

when ⎓ is a single bond, X is selected from OH and H and the carbon to which X is attached is substituted with H to provide proper valence (e.g. H—C[($CH_2$)(C)]—X);

$R^1$, $R^2$, $R^3$, $R^4$, $R^5$, and $R^6$ are each independently selected from hydrogen or a pentose or hexose carbohydrate, wherein at least one of $R^1$-$R^6$ is a pentose or hexose carbohydrate that is not glucose; and the total number of carbohydrates is four, five or six.

In each instance, the pentose or hexose carbohydrate can be selected from any known pentose or hexose carbohydrate. Exemplary pentose and hexose carbohydrates include, but are not limited to, glucose, xylose, ribose, arabinose, deoxyglucose, lyxose, fucose, allose, allulose, altrose, mannose, gulose, iodose, galactose, talose, and rhamnose. The carbohydrate linkage can be in the α- or β-configuration. The carbohydrate can be in the D- or L-configuration.

In one embodiment, one of $R^1$-$R^4$ is a pentose or hexose carbohydrate that is not glucose and $R^5$ and $R^6$ are hydrogen.

In another embodiment, one of $R^1$-$R^4$ is a xylose and $R^5$ and $R^6$ are hydrogen.

In certain embodiments, the total number of carbohydrates in the compound of Formula I is four, five or six and the non-glucose pentose or hexose carbohydrate is xylose.

In certain other embodiments, the total number of carbohydrates in the compound of Formula I is four, five or six and the non-glucose pentose or hexose carbohydrate is not xylose.

In a second aspect, the present invention provides a mogroside of Formula II:

Formula II

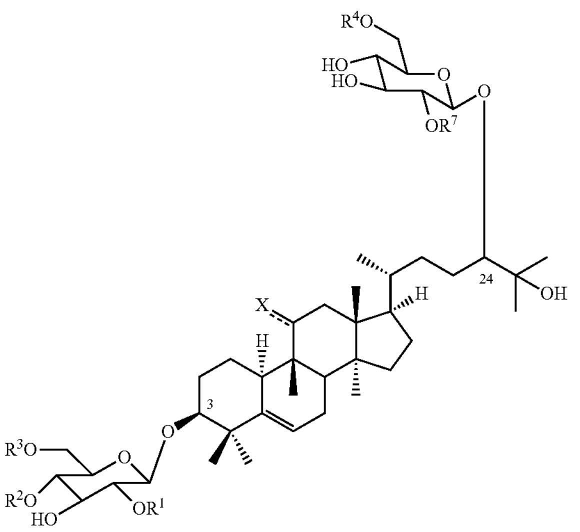

wherein:

when ⎓ is a double bond, X is O;

when ⎓ is a single bond, X is selected from OH and H and the carbon to which X is attached is substituted with H to provide proper valence (e.g. H—C[($CH_2$)(C)]—X);

$R^1$, $R^2$, $R^3$, $R^4$, and $R^7$ are each independently selected from hydrogen or a pentose or hexose carbohydrate, wherein at least one of $R^1$, $R^2$, $R^3$, $R^4$ and $R^7$ is a pentose or hexose carbohydrate that is not glucose.

In each instance, the pentose or hexose carbohydrate can be selected from any known pentose or hexose carbohydrate. Exemplary pentose and hexose carbohydrates include, but are not limited to, glucose, xylose, ribose, arabinose, deoxyglucose, lyxose, fucose, allose, allulose, altrose, mannose, gulose, iodose, galactose, talose, and rhamnose. The carbohydrate linkage can be in the α- or β-configuration.

In certain embodiments, when the total number of carbohydrates in the compound of Formula II is three, four, five or six, the non-glucose pentose or hexose carbohydrate is xylose.

Specific mogrosides of the present disclosure include, but are not limited to, Mogrol-3-O-[β-D-glucopyranoside]-24-O-{[β-D-glucopyranosyl-(1→2)]-[β-D-xylopyranosyl-(1→6)]-β-D-glucopyranoside}, Mogrol-3-O-[β-D-glucopyranoside]-24-O-{[β-D-glucopyranosyl-(1→2)]-[α-L-rhamnopyranosyl-(1→6)]-β-D-glucopyranoside}, Mogrol-3-O-[β-D-glucopyranosyl-(1→6)-β-D-glucopyranoside]-24-O-[β-D-xylopyranosyl-(1→6)-β-D-glucopyranoside], Mogrol-3-O-[β-D-glucopyranoside]-24-O-[{β-D-glucopyranosyl-(1→2)]-[α-D-galactopyranosyl-(1→6)]-β-D-glucopyranoside}, Mogrol-3-O-[α-L-rhamnopyranosyl-(1→6)-β-D-glucopyranoside]-24-O-[β-D-glucopyranosyl-(1→2)-β-D-glucopyranoside], mogrol-3-O-[{β-D-glucopyranosyl-(1→6)}-β-D-glucopyranoside]-24-O-[{β-D-xylopyranosyl-(1→2)}-{β-D-glucopyranosyl-(1→6)}β-D-glucopyranoside], mogrol-3-O-[α-D-xylopyranosyl-(1→6)-β-D-glucopyranoside]-24 xylopyranosyl-(1→6)-β-D-glucopyranoside, mogrol-3-O-[β-D-xylopyranosyl-(1→4)]-[β-D-xylopyranosyl-(1→6)]-β-D-glucopyranoside-24-O-[β-D-glucopyranosyl-(1→2)]-[β-D-glucopyranosyl-(1→6)]-β-D-glucopyranoside, mogrol-3-O-{[β-D-glucopyranosyl-(1→6)]-β-D-glucopyranoside}-24-O-{[α-L-rhamnopyranosyl-(1→2)]-[3-D-glucopyranosyl-(1→6)]-β-D-glucopyranoside}, mogrol-3-O-[α-D-xylopyranosyl-(1→6)-β-D-glucopyranoside]-24-O-[α-D-xylopyranosyl-(1→6)-β-D-glucopyranoside], mogrol-3-O-[β-D-glucopyranoside]-24-O-[α-D-xylopyranosyl-(1→6)-β-D-glucopyranoside], mogrol-3-O-[α-D-xylopyranosyl-(1→6)-β-D-glucopyranoside]-24-O-β-D-glucopyranoside, 3-O-β-D-Glucopyranosyl mogrol 24-O-α-L-rhamnopyranosyl-(1→2)-β-D-glucopyranosyl-(1→6)-β-D-glucopyranoside and mogrol-3-O-{[β-D-glucopyranosyl-(1→6)]-O-D-glucopyranoside-24-O-[β-D-glucopyranosyl-(1→2)]-[β-D-xylopyranosyl-(1→6)]-β-D-glucopyranoside}.

In a particular embodiment, the mogroside is isolated and purified.

In a further aspect, the present invention is a composition comprising at least one mogroside described herein. In a particular embodiment, the present invention is a composition comprising at least one isolated and purified mogroside described herein.

In one embodiment, the present invention is a sweetener composition comprising at least one mogroside described herein.

In another embodiment, the present invention is a taste enhancing composition comprising at least one mogroside described herein, wherein the mogroside is present in the composition in an amount effective to provide a concentration at or below the flavor recognition threshold of the mogroside when the added to a consumable.

In yet another embodiment, the present invention is a sweetness enhancing composition comprising at least one mogroside described herein, wherein the mogroside is present in the composition in an amount effective to provide a concentration at or below the sweetness recognition threshold of the mogroside when the sweetness enhancing composition is added to a consumable.

In yet another embodiment, the present invention is a consumable comprising at least one mogroside described herein. Suitable consumables include, but are not limited to, liquid-based or dry consumables, such as, for example, pharmaceutical compositions, edible gel mixes and compositions, dental compositions, foodstuffs, beverages and beverage products.

In a particular embodiment, the present invention is a beverage comprising at least one mogroside described herein. In a particular embodiment, the mogroside is present in the beverage at a concentration that is above, at or below the threshold sweetness recognition concentration of the mogroside.

In another aspect, the present invention is a method of preparing a consumable comprising (i) providing a consumable matrix and (ii) adding at least one mogroside described herein to the consumable matrix to provide a consumable.

In a particular embodiment, the present invention is a method of preparing a beverage comprising (i) providing a beverage matrix and (ii) adding at least one mogroside described herein to the beverage matrix to provide a beverage.

In another aspect, the present invention is a method of enhancing the sweetness of a consumable comprising (i) providing a consumable comprising at least one sweet ingredient and (ii) adding at least one isolated and purified mogroside described herein to the consumable to provide a consumable with enhanced sweetness, wherein the mogroside is present in the consumable with enhanced sweetness at a concentration at or below the sweetness recognition threshold of the mogroside. In a particular embodiment, the consumable is a beverage.

In some embodiments, the compositions of the present invention comprise one or more sweeteners, additives and/or functional ingredients.

In one embodiment, the present invention is a consumable comprising at least one mogroside of the present invention and one or more sweeteners, additives and/or functional ingredients. In another embodiment, the present invention is a beverage comprising at least one mogroside of formula of the present invention and one or more sweeteners, additives and/or functional ingredients.

In another aspect, the present invention is a method of purifying a mogroside of the present invention comprising (i) passing a solution comprising a source material comprising a mogroside of the present invention through a HPLC column and (ii) eluting fractions comprising a mogroside of the present invention to provide a purified mogroside composition comprising a mogroside of the present invention in at least about 80% by weight. Exemplary source materials include, but are not limited to, mixtures of mogrosides, Luo Han Guo extract (commercial or prepared), and compositions resulting from the bioconversion processes described herein.

DETAILED DESCRIPTION

Figure 1A:
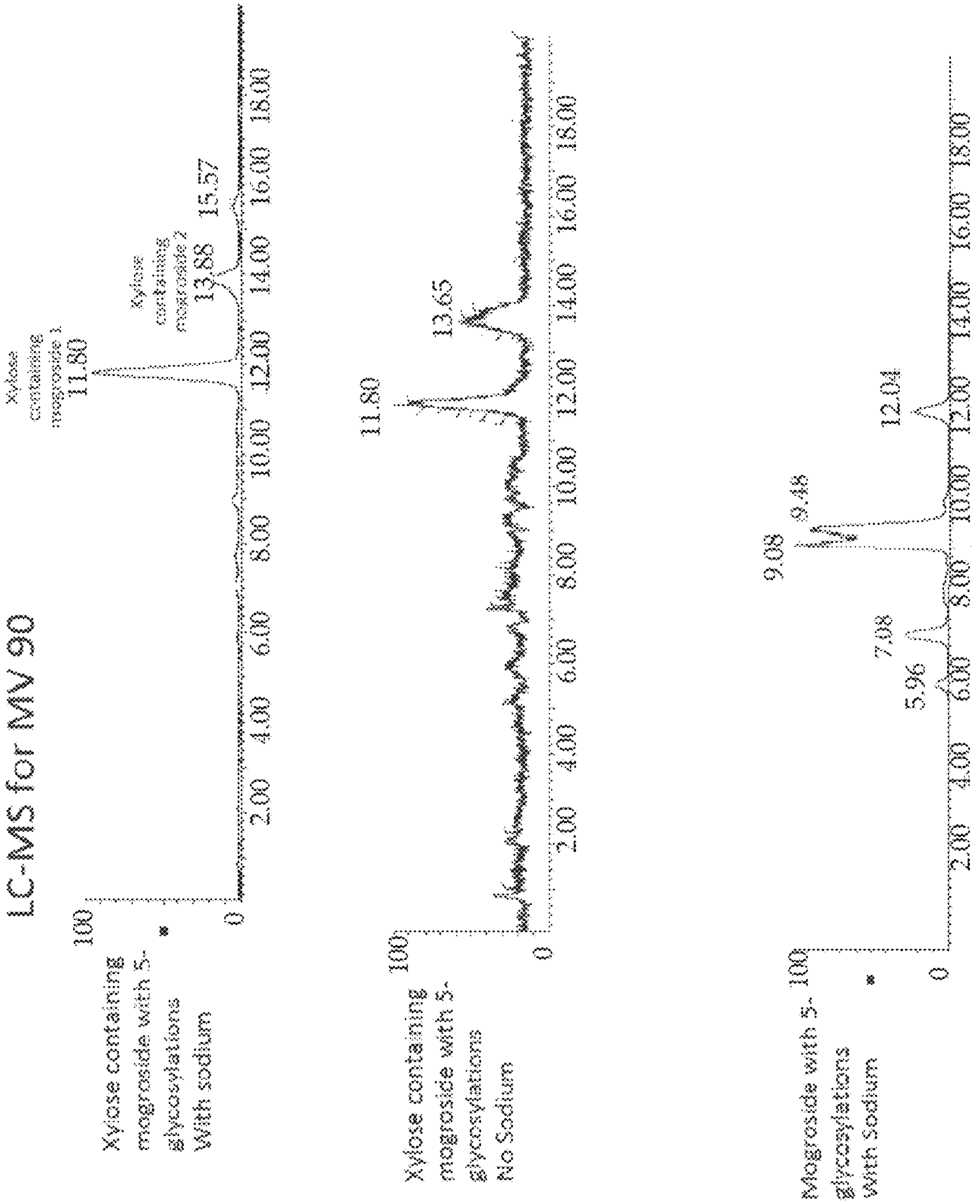
FIG. 1 shows the LC-MS for the 90% Mogroside V starting material (MV 90) (Example 1).

Disclosed herein are compounds, compositions and methods for use as sweeteners in beverages and foods. The disclosed compounds include mogroside compounds containing non-glucose carbohydrate units. Surprisingly, it has been found that mogrosides of the present invention are useful in various applications, for example as a sweetener or food additive in consumables such as for example beverages and foods. Such compositions include mogrosides of the present invention alone or in blends with other sweeteners, additives or taste enhancers.

I. Definitions

As used herein, the term “consumable” refers to a substance suitable for ingestion by an individual. Exemplary consumables include but are not limited to edible gel mixes and compositions, dental compositions, foodstuffs (confections, condiments, chewing gum, cereal compositions, baked goods, dairy products, and tabletop sweetener compositions) beverages and beverage products.

As used herein, the term “monk fruit” or “Luo Han Guo” (luo han guo) refers to the fruit of *Siraitia grosvenori*, a member of the Curcubitaceae.

As used herein, the term “pH” refers to a figure expressing the acidity or alkalinity of a solution on a logarithmic scale on which 7 is neutral, lower values are more acid, and higher values more alkaline. The pH is equal to −log 10 c, where c is the hydrogen ion concentration in moles per liter.

As used herein, the term “purified” means that the compound has been increased in purity, such that it exists in a form that is more pure than it exists in its natural environment and/or in an extract. Purity is a relative term and does not necessarily mean absolute purity.

II. Compounds

The present disclosure provides a mogroside compound of Formula I:

Formula I

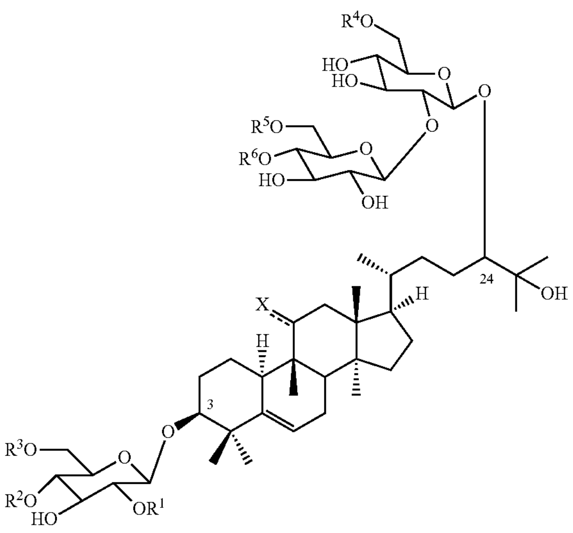

wherein:

when ⎓ is a double bond, X is O;

when ⎓ is a single bond, X is selected from OH and H and the carbon to which X is attached is substituted with H to provide proper valence (e.g. H—C[$(CH_2)$(C)]—X);

$R^1$, $R^2$, $R^3$, $R^4$, $R^5$, and $R^6$ are each independently selected from hydrogen or a pentose or hexose carbohydrate, wherein at least one of $R^1$-$R^6$ is a pentose or hexose carbohydrate that is not glucose; and the total number of carbohydrates is four, five or six.

In each instance, the pentose or hexose carbohydrate can be selected from any known pentose or hexose carbohydrate. Exemplary pentose and hexose carbohydrates include, but are not limited to, glucose, xylose, ribose, arabinose, deoxyglucose, lyxose, fucose, allose, allulose, altrose, mannose, gulose, iodose, galactose, talose, and rhamnose. The carbohydrate linkage can be in the α- or β-configuration. The carbohydrate can be in the D- or L-configuration.

Compounds of Formula I have at least four total carbohydrates (i.e. the sum of the carbohydrate units at the C-3 and C-24 positions). In one embodiment, the compound of Formula I has four total carbohydrates. In still another embodiment, the compound of Formula I has five total carbohydrates. In yet another embodiment, the compound of Formula I has six total carbohydrates.

In one embodiment, one of $R^1$-$R^4$ is a pentose or hexose carbohydrate that is not glucose and $R^5$ and $R^6$ are hydrogen.

In one embodiment, the total number of carbohydrates in the compound of Formula I is four, five or six and the non-glucose pentose or hexose carbohydrate is xylose.

In another embodiment, the total number of carbohydrates in the compound of Formula I is four, five or six and the non-glucose pentose or hexose carbohydrate is rhamnose.

In still another embodiment, the total number of carbohydrates in the compound of Formula I is four, five or six and the non-glucose pentose or hexose carbohydrate is galactose.

In certain embodiments, the mogroside of Formula I is an 11-oxomogroside of Formula Ia:

Formula Ia

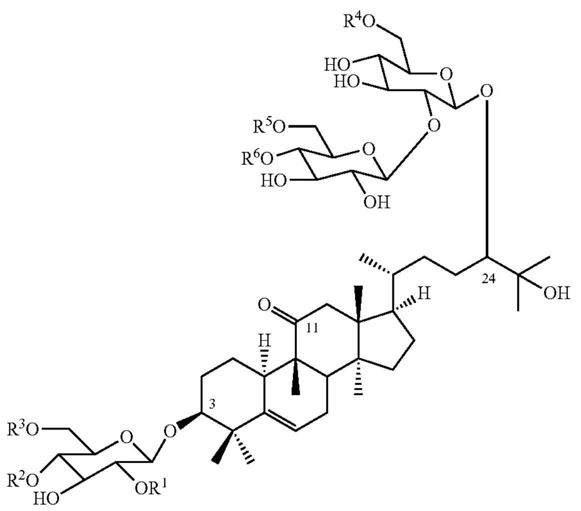

wherein $R^1$, $R^2$, $R^3$, $R^4$, $R^5$, and $R^6$ are as defined above for Formula I.

In certain other embodiments, the mogroside of Formula I is an 11-deoxomogroside of Formula Ib:

Formula Ib

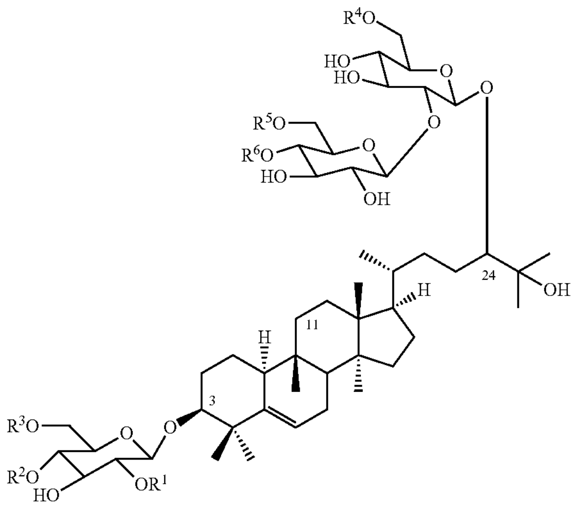

wherein $R^1$, $R^2$, $R^3$, $R^4$, $R^5$, and $R^6$ are as defined above for Formula I.

In certain other embodiments, the mogroside of Formula I is a compound of Formula Ic:

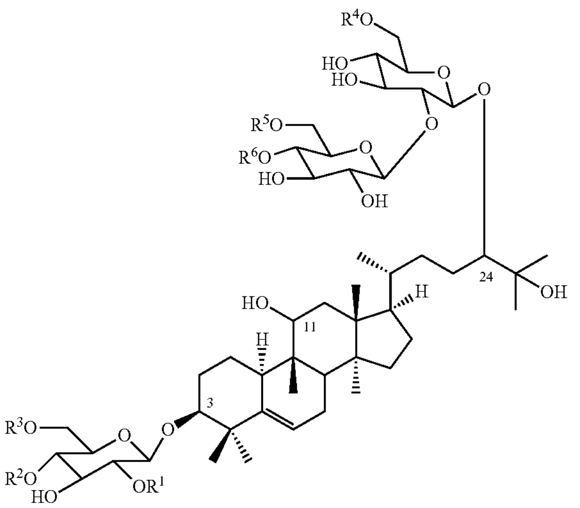

wherein $R^1$, $R^2$, $R^3$, $R^4$, $R^5$, and $R^6$ are as defined above for Formula I.

The 11-OH can be in the R- or S-configuration.

The present disclosure also provides a mogroside of Formula II:

Formula II

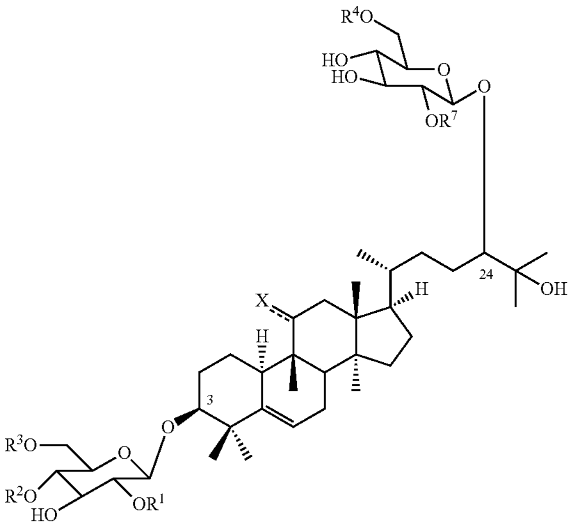

wherein:

when $\overline{\cdots}$ is a double bond, X is O;

when $\overline{\cdots}$ is a single bond, X is selected from OH and H and the carbon to which X is attached is substituted with H to provide proper valence (e.g. H—C[($CH_2$)(C)]—X);

$R^1$, $R^2$, $R^3$, $R^4$, and $R^7$ are each independently selected from hydrogen or a pentose or hexose carbohydrate, wherein at least one of $R^1$, $R^2$, $R^3$, $R^4$ and $R^7$ is a pentose or hexose carbohydrate that is not glucose.

In each instance, the pentose or hexose carbohydrate can be selected from any known pentose or hexose carbohydrate. Exemplary pentose and hexose carbohydrates include, but are not limited to, glucose, xylose, ribose, arabinose, deoxyglucose, lyxose, fucose, allose, allulose, altrose, mannose, gulose, iodose, galactose, talose, and rhamnose. The carbohydrate linkage can be in the α- or β-configuration.

Compounds of Formula II have at least three total carbohydrates (i.e. the sum of the carbohydrate unites at the C-3 and C-24 positions). In one embodiment, the compound of Formula II has three total carbohydrates. In another embodiment, the compound of Formula II has four total carbohydrates. In still another embodiment, the compound of Formula II has five total carbohydrates. In yet another embodiment, the compound of Formula II has six total carbohydrates.

In one embodiment, the total number of carbohydrates in the compound of Formula II is three, four, five or six and the non-glucose pentose or hexose carbohydrate is xylose.

In another embodiment, the total number of carbohydrates in the compound of Formula II is three, four, five or six and the non-glucose pentose or hexose carbohydrate is rhamnose.

In certain embodiments, the mogroside of Formula II is an 11-oxomogroside of Formula IIa:

Formula IIa

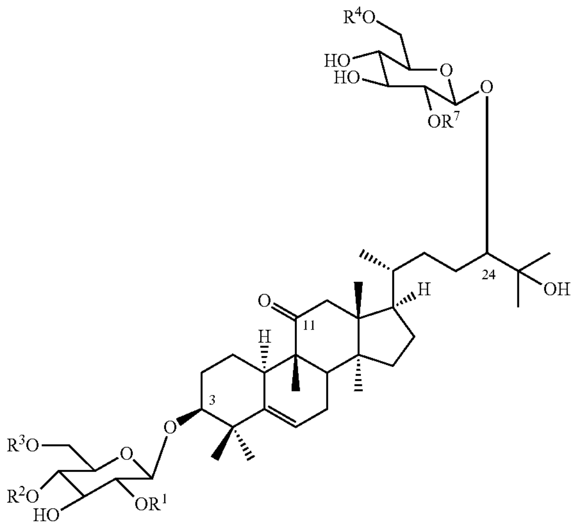

wherein $R^1$, $R^2$, $R^3$, $R^4$, and $R^7$ are as defined above for Formula II.

In certain other embodiments, the mogroside of Formula II is an 11-deoxomogroside of Formula IIb:

Formula IIb

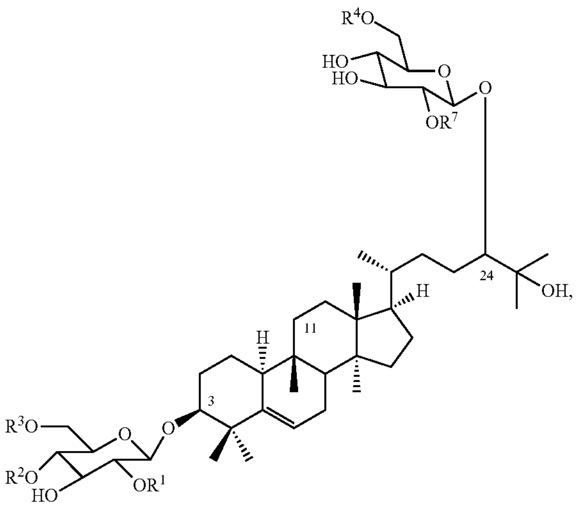

wherein $R^1$, $R^2$, $R^3$, $R^4$, and $R^7$ are as defined above for Formula II.

In certain other embodiments, the mogroside of Formula II is a compound of Formula IIC:

Formula IIc

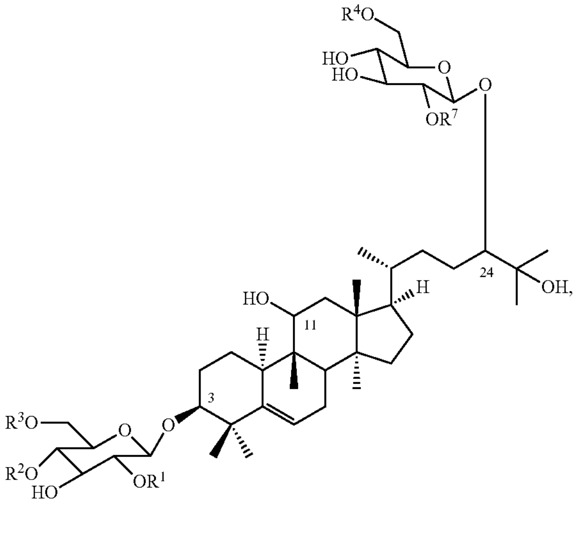

wherein $R^1$, $R^2$, $R^3$, $R^4$, and $R^7$ are as defined above for Formula II. The 11-OH can be in the R- or S-configuration.

In one embodiment, the mogroside of the present invention is selected from the following:

(i) mogrol-3-O-[β-D-glucopyranoside]-24-O-{[β-D-glucopyranosyl-(1→2)]-[β-D-xylopyranosyl-(1→6)]-β-D-glucopyranoside} (CC-00489):
CC-00489
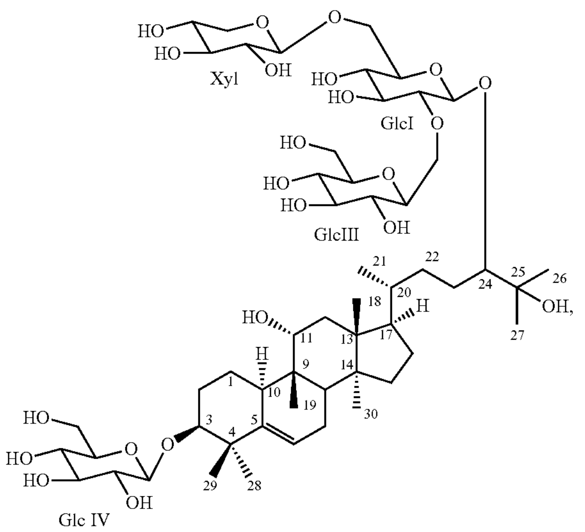
(ii) mogrol-3-O-[β-D-glucopyranoside]-24-O-{[β-D-glucopyranosyl-(1→2)]-[α-L-rhamnopyranosyl-(1→6)]-β-D-glucopyranoside} (CC-00491):
CC-00491
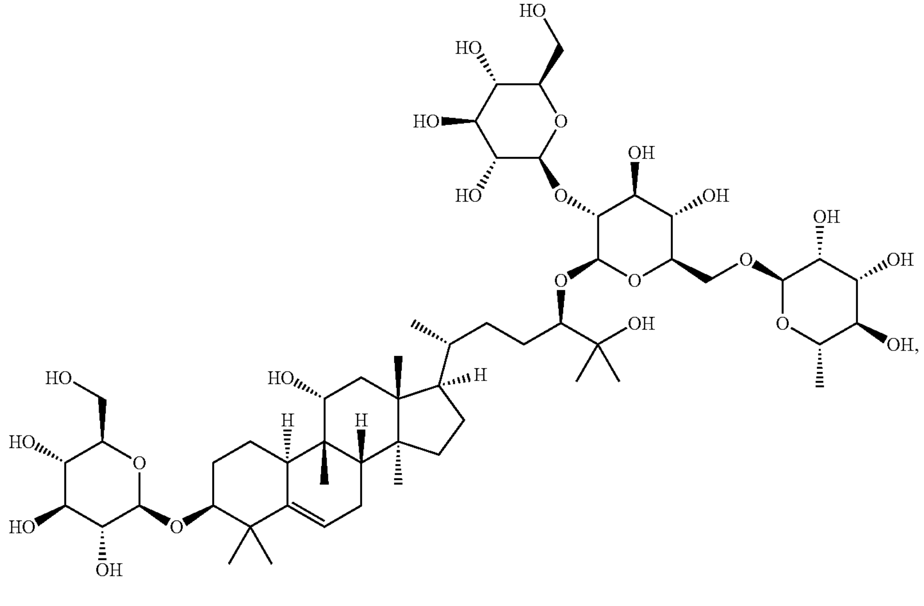

(iii) mogrol-3-O-[β-D-glucopyranosyl-(1→6)-β-D-glucopyranoside]-24-O-[β-D-xylopyranosyl-(1→6)-β-D-glucopyranoside] (CC-00497):
CC-00497
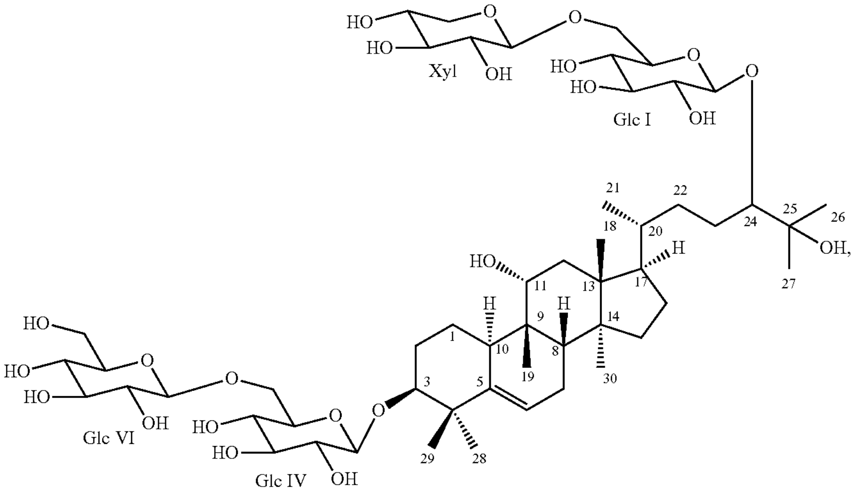
(iv) mogrol-3-O-[β-D-glucopyranoside]-24-O-{[β-D-glucopyranosyl-(1→2)]-[α-D-galactopyranosyl-(1→6)]-β-D-glucopyranoside} (CC-00498):
CC-00498
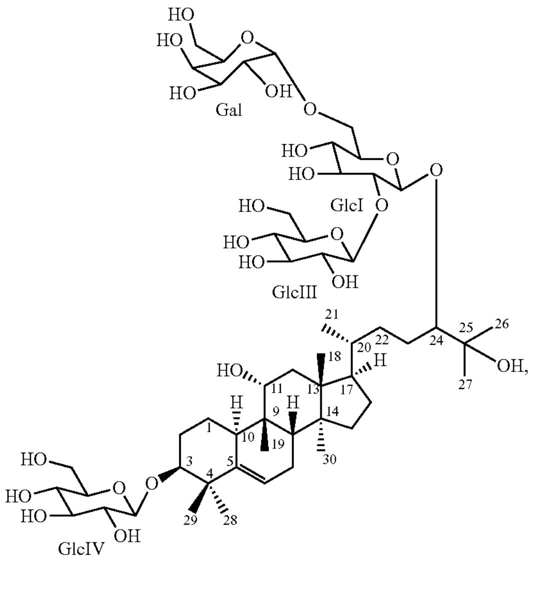
and (v) mogrol-3-O-[α-L-rhamnopyranosyl-(1→6)-β-D-glucopyranoside]-24-O-[β-D-glucopyranosyl-(1→2)-β-D-glucopyranoside] (CC-00500):
CC-00500
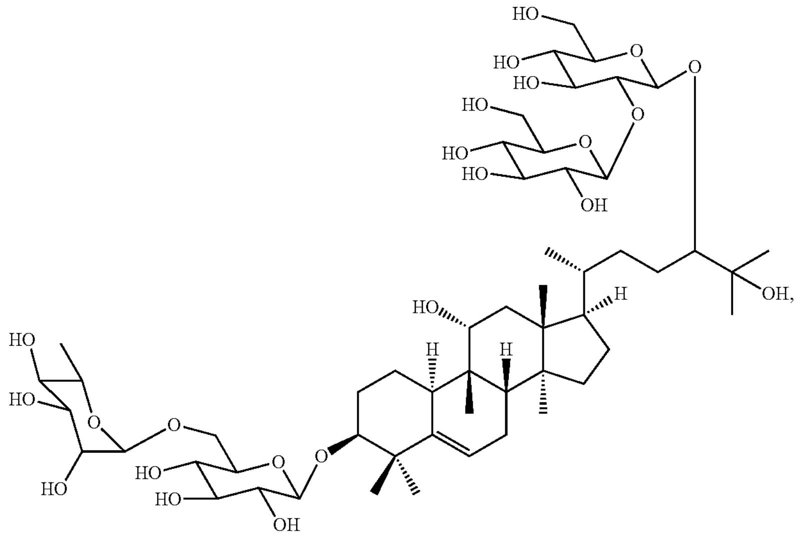
(vi) mogrol-3-O-[{β-D-glucopyranosyl-(1→6)}-β-D-glucopyranoside]-24-O-[{β-D-xylopyranosyl-(1→2)}-{β-D-glucopyranosyl-(1→6)}β-D-glucopyranoside] (CC-00507):
CC-00507
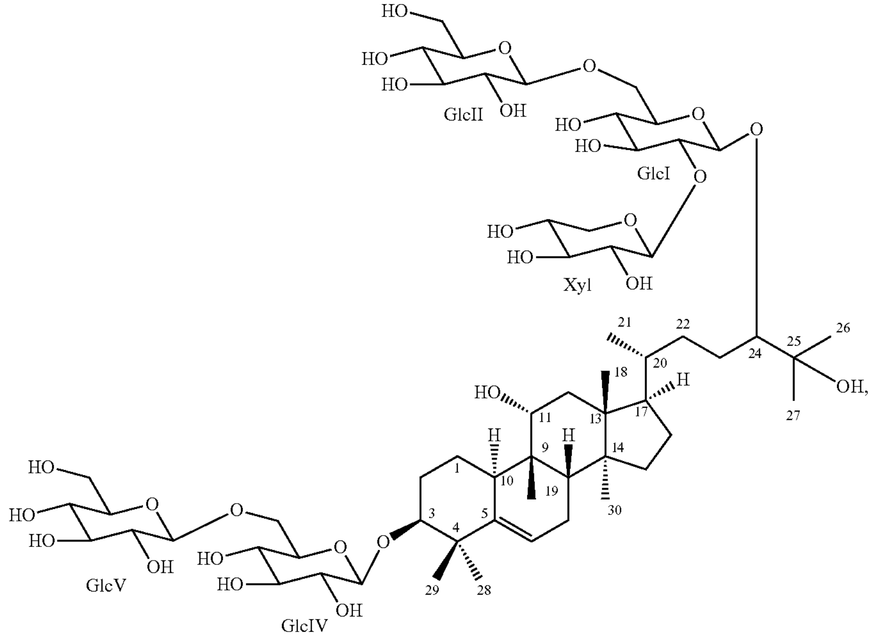

(vii) mogrol-3-O-[α-D-xylopyranosyl-(1→6)-β-D-glucopyranoside]-24-O-[α-D-xylopyranosyl-(1→6)-β-D-glucopyranoside] (CC-00518)
CC-00518
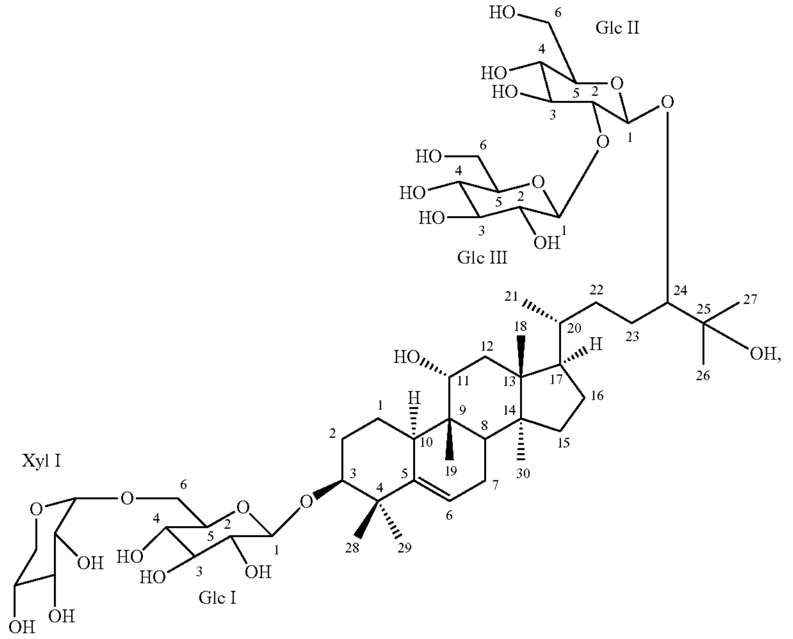
(viii) mogrol-3-O-{[β-D-xylopyranosyl-(1→4)]-[β-D-glucopyranosyl-(1→6)]-β-D-glucopyranoside}-24-O-{[β-D-glucopyranosyl-(1→2)]-[β-D-glucopyranosyl-(1→6)-β-D-glucopyranoside} (CC-00520)
CC-00520
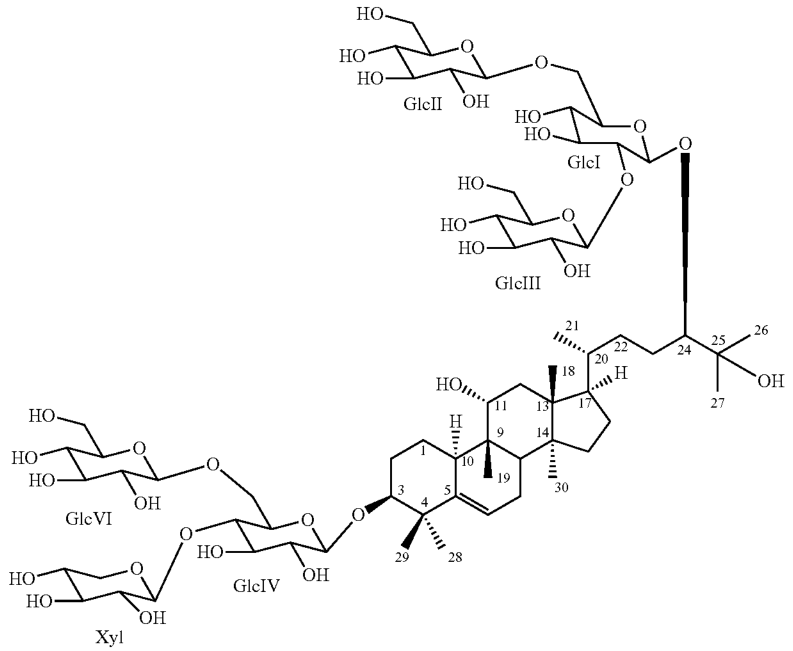

(ix) Mogrol-3-O-{[β-D-glucopyranosyl-(1→6)]-β-D-glucopyranoside}-24-O-{[α-L-rhamnopyranosyl-(1→2)]-[β-D-glucopyranosyl-(1→6)]-β-D-glucopyranoside} (CC-00539)
CC-00539
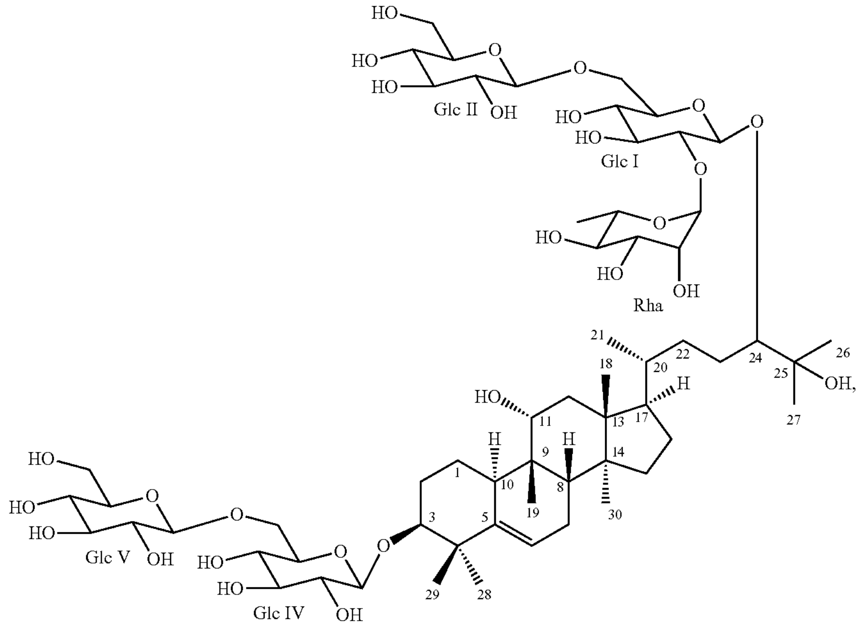
(x) mogrol-3-O-[α-D-xylopyranosyl-(1→6)-β-D-glucopyranoside]-24-O-[α-D-xylopyranosyl-(1→6)-β-D-glucopyranoside] (CC-00540)
CC-00540
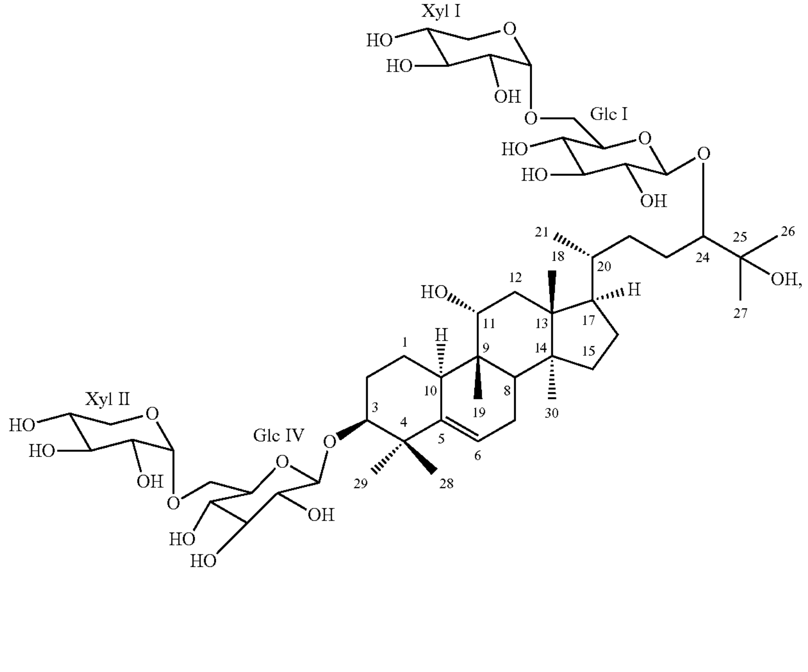

(xi) mogrol-3-O-[β-D-glucopyranoside]-24-O-[α-D-xylopyranosyl-(1→6)-β-D-glucopyranoside] (CC-00541)
CC-00541
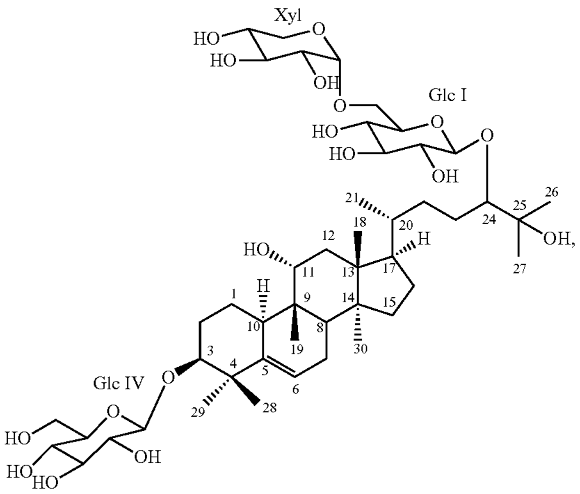
(xii) Mogrol-3-O-[α-D-xylopyranosyl-(1→6)-β-D-glucopyranoside]-24-O-β-D-glucopyranoside (CC-00542)
CC-00542
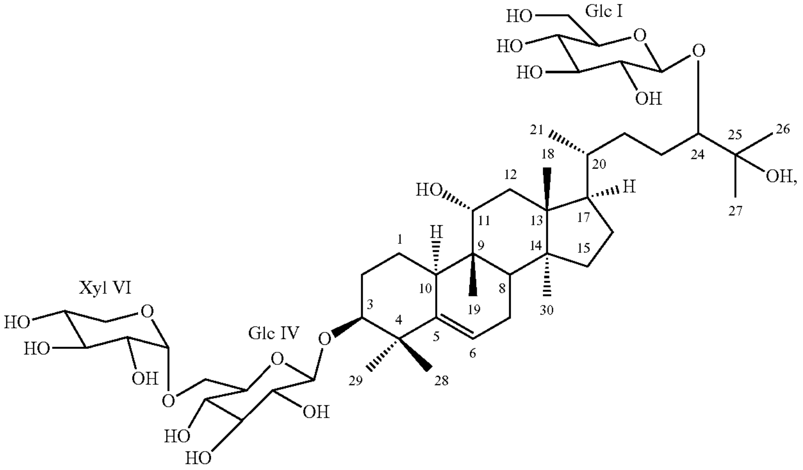

(xiii) 3-O-β-D-Glucopyranosyl mogrol 24-O-α-L-rhamnopyranosyl-(1→2)-β-D-glucopyranosyl-(1→6)-β-D-glucopyranoside (CC-00550)

CC-00550

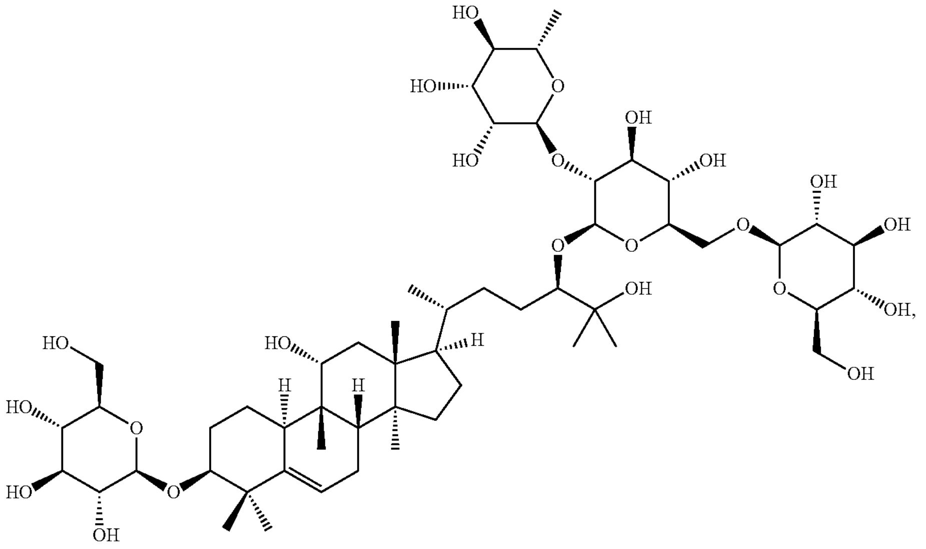

and (xiv) Mogrol-3-O-{[β-D-glucopyranosyl-(1→6)]-O-D-glucopyranoside}-24-O-{[β-D-glucopyranosyl-(1→2)]-[β-D-xylopyranosyl-(1→6)]-β-D-glucopyranoside} (CC-00551)

CC-00551

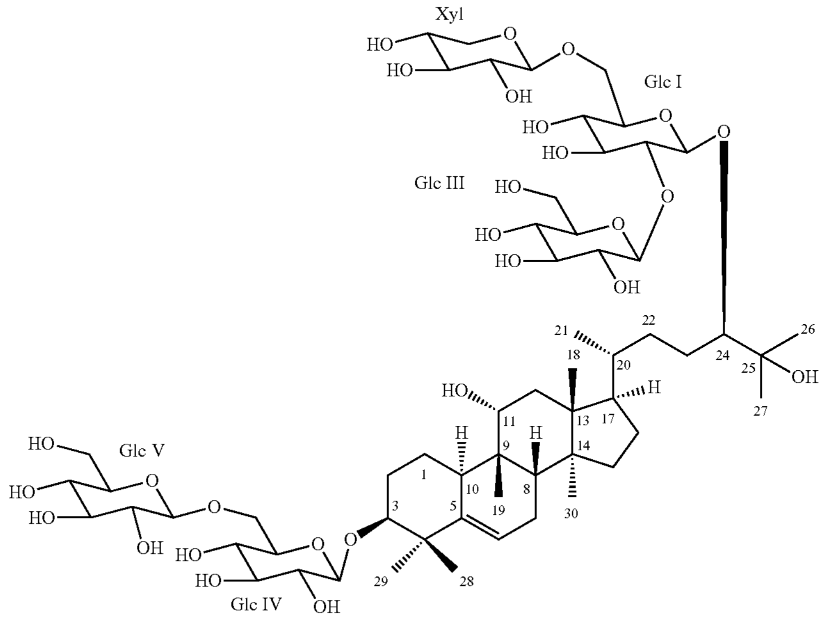

In exemplary embodiments, the mogroside of the present invention is isolated and purified.

The term "isolated and purified", as used herein, means that the compound is about 95% by weight or greater on a dry basis, i.e. is greater than 95% pure. The remainder of the mixture is typically other mogrosides and/or Luo Han Guo extract. In more specific embodiments, the mogroside of the formulae described herein has a purity of about 96% or greater, about 97% or greater, about 98% or greater or about 99% or greater. In some embodiments, the mogroside is enzymatically produced.

In some embodiments, the mogroside of the present invention is sweet. The sweetness of a given composition is typically measured with reference to a solution of sucrose. See generally "A Systematic Study of Concentration-Response Relationships of Sweeteners," G. E. DuBois, D. E. Walters, S. S. Schiffman, Z. S. Warwick, B. J. Booth, S. D. Pecore, K. Gibes, B. T. Carr, and L. M. Brands, in *Sweet-*

*eners: Discovery, Molecular Design and Chemoreception*, D. E. Walters, F. T. Orthoefer, and G. E. DuBois, Eds., American Chemical Society, Washington, DC (1991), pp 261-276.

The sweetness of a non-sucrose sweetener can be measured against a sucrose reference by determining the non-sucrose sweetener's sucrose equivalence (SE). Typically, taste panelists are trained to detect sweetness of reference sucrose solutions containing between 1-15% sucrose (w/v). Other non-sucrose sweeteners are then tasted at a series of dilutions to determine the concentration of the non-sucrose sweetener that is as sweet as a given percent sucrose reference. For example, if a 1% solution of a non-sucrose sweetener is as sweet as a 10% sucrose solution, then the sweetener is said to be 10 times as potent as sucrose, and has 10% sucrose equivalence.

In one embodiment, the mogroside is present in an amount that, when added to a consumable, provides a sucrose equivalence of greater than about 2% (w/v), such as, for example, greater than about 3% SE, about 4% SE, about 5% SE, about 6% SE, about 7% SE, about 8% SE, about 9% SE, about 10% SE, about 11% SE, about 12%, SE about 13% SE or about 14% SE.

The amount of sucrose, and thus another measure of sweetness, in a reference solution may be described in degrees Brix (° Bx). One degree Brix is 1 gram of sucrose in 100 grams of solution and represents the strength of the solution as percentage by weight (% w/w) (strictly speaking, by mass). In one embodiment, the mogroside of the present invention is present in an amount that, when added to a consumable, provides a sweetness equivalent from about 0.50 to 14 degrees Brix, such as, for example, from about 5 to about 12 degrees Brix, about 7 to 10 degrees Brix, or above 10 degrees Brix.

In exemplary embodiments, an isolated and purified mogroside of the present invention has about 30% or more sweetness compared to the partially purified mogroside or Luo Han Guo, such as, for example, about 40% or more, about 50% or more, about 60% or more, about 70% or more, about 80% or more or about 90% or more.

In other exemplary embodiments, an isolated and purified mogroside of the present invention has at least about 30% less bitterness (the taste stimulated by certain substances such as quinine, caffeine and sucrose octa-acetate) compared the partially purified mogroside or Luo Han Guo, such as, for example, at least about 40%, at least about 50%, at least about 60%, at least about 70%, at least about 80% or at least about 90%. In a particular embodiment, the isolated and purified mogroside of the present invention has substantially no bitterness. Methods of measuring bitterness of a compound are known in the art In still other exemplary embodiments, an isolated and purified mogroside of the present invention has at least about 30% less sweet lingering aftertaste (the intensity of the sweet taste after expectoration) compared to the partially purified mogroside or Luo Han Guo, such as, for example, at least about 50%, at least about 60%, at least about 70%, at least about 80% or at least about 90%. In a particular embodiment, the isolated and purified mogroside of the present invention has substantially no sweet lingering aftertaste. Methods of measuring sweet lingering aftertaste are known in the art.

In yet other exemplary embodiments, an isolated and purified mogroside of the present invention has at least about 30% less metallic taste (taste associated with metals, tinny or iron) compared to the partially purified mogroside or Luo Han Guo, such as, for example, at least about 50%, at least about 60%, at least about 70%, at least about 80% or at least about 90%. In a particular embodiment, the isolated and purified mogroside of the present invention has substantially no metallic taste.

In exemplary embodiments, an isolated and purified mogroside of the present invention exhibits a maximal response (maximum sweetness (% SE) achieved with increasing concentration of compound) that is at least about 30% greater compared to the partially purified mogroside or Luo Han Guo, such as, for example, at least about 40% greater, at least about 50% greater, at least about 60% greater, at least about 70% greater, at least about 80% greater or at least about 90% greater. Methods of measuring the maximal response of a compound are known in the art. In one embodiment, the method is an in vitro cell assay. In some embodiments, the cell is expressing a sweet taste receptor or a dimer of sweet taste receptor.

In other exemplary embodiments, an isolated and purified mogroside of the present invention exhibits a sweetness onset (the time until maximum sweetness is experienced) that is at least about 30% shorter than the partially purified mogroside or Luo Han Guo, such as, for example, at least about 40% short, at least about 50% shorter, at least about 60% shorter, at least about 70% shorter, at least about 80% shorter or at least about 90% shorter. Methods of measuring sweetness onset are known in the art. In one embodiment, the method is an in vitro cell assay. In some embodiments, the cell is expressing a sweet taste receptor or a dimer of sweet taste receptor.

III. Compositions

The present invention includes compositions comprising at least one mogroside of the present invention. "Composition," as the term is used herein, refers to a mixture of at least one mogroside of the present invention and at least one other substance.

In a particular embodiment, the at least one other substance does not occur and/or is not admixed with the diterpene glycoside in nature. As such, these compositions do not occur in nature.

In one embodiment, the present invention is a composition comprising at least one mogroside of the present invention, provided as part of a mixture. In a particular embodiment, the mixture is selected from the group consisting of mogrosides, Luo Han Guo, by-products of other mogrosides' isolation and purification processes, commercially available mogroside extracts, by-products of biotransformation reactions, or any combination thereof.

In one embodiment, the mixture contains at least one mogroside of the present invention in an amount that ranges from about 1% to about 99% by weight on a dry basis, such as, for example, about 5% to about 99%, from about 10% to about 99%, from about 20% to about 99%, from about 30% to about 99%, from about 40% to about 99%, from about 50% to about 99%, from about 60% to about 99%, from about 70% to about 99%, from about 80% to about 99% and from about 90% to about 99%. In a particular embodiment, the mixture contains at least one mogroside of the present invention in an amount greater than about 90% by weight on a dry basis, for example, greater than about 91%, greater than about 92%, greater than about 93%, greater than about 94%, greater than about 95%, greater than about 96%, greater than about 97%, greater than about 98% and greater than about 99%.

A composition may comprise at least about 5% of a mogroside of the present invention by weight, such as, for example, at least about 10%, at least about 20%, at least about 30%, at least about 40%, at least about 50%, at least about 60%, at least about 70%, at least about 80%, at least about 90%, at least about 95% or at least about 97%.

In other embodiments, a composition has a total mogroside content of about 95% by weight or greater on a dry basis. In some embodiments, the composition has a total mogroside content of about 96% or greater, about 97% or greater, about 98% or greater or about 99% or greater. "Total mogroside content", as used herein, refers to the sum of the relative weight contributions of each mogroside in a sample, including the non-glucose substituted mogrosides as described herein.

The term "purified mogroside", as used herein, refers to a mogroside present in at least about 50% by weight in a mixture, e.g. Luo Han Guo, such as, for example, at least about 60%, at least about 70%, at least about 80%, at least about 90%, at least about 95% or at least about 97%.

In one embodiment, the present invention is a composition comprising at least one mogroside described herein provided as a pure compound, i.e. >99% by weight on a dry basis.

A mogroside of the present invention may be present in the composition in an amount effective to provide a concentration of the mogroside of the present invention from about 1 ppm to about 10,000 ppm when the composition is added to a consumable, such as, for example, from about 1 ppm to about 4,000 ppm, from about 1 ppm to about 3,000 ppm, from about 1 ppm to about 2,000 ppm, from about 1 ppm to about 1,000 ppm, from about 1 ppm to about 600 ppm, from about 1 ppm to about 500 ppm, from about 1 ppm to about 400 ppm, from about 1 ppm to about 300 ppm, from about 1 ppm to about 200 ppm or from about 1 ppm to about 100 ppm.

In another embodiment, the mogroside of the present invention is present in the composition in an amount effective to provide a concentration of the mogroside of the present invention from about 10 ppm to about 1,000 ppm, from about 25 ppm to about 1,000 ppm, from about 50 ppm to about 1,000 ppm, from about 100 ppm to about 1,000 ppm.

The weight ratio of the at least one other substance to the mogroside of the present invention can vary. Typically, the weight ratio of the at least one other substance to the mogroside of the present invention is from about 500:1 to about 2:1, such as, for example, from about 100:1 to about 2:1, from about 50:1 to about 2:1, from about 25:1 to about 2:1, from about 10:1 to about 2:1, from about 5:1 to about 2:1, from about 500:1 to about 400:1, from about 500:1 to about 300:1, from about 500:1 to about 200:1, from about 500:1 to about 100:1, from about 500:1 to about 50:1, from about 500:1 to about 25:1, from about 500:1 to about 10:1, from about 400:1 to about 300:1, from about 400:1 to about 200:1, from about 400:1 to about 100:1, from about 400:1 to about 50:1, from about 400:1 to about 25:1, from about 400:1 to about 10:1, from about 400:1 to about 6.67:1, from about 300:1 to about 200:1, from about 300:1 to about 100:1, from about 300:1 to about 50:1, from about 300:1 to about 25:1, from about 300:1 to about 10:1, from about 300:1 to about 6.67:2, from about 200:1 to about 100:1, from about 200:1 to about 50:1, from about 200:1 to about 25:1, from about 200:1 to about 10:1, from about 100:1 to about 50:1, from about 100:1 to about 25:1, from about 100:1 to about 10:1, from about 100:1 to about 6.67:1, from about 50:1 to about 25:1, from about 50:1 to about 25:1, from about 50:1 to about 10:1, from about 50:1 to about 6.65:1, from about 25:1 to about 10:1, from about 25:1 to about 6.67:1, from about 10:1 to about 6.67:1 and any range in between.

A. Sweetener Compositions

As noted above, in some embodiments, the mogroside of the present invention is sweet. Accordingly, the present invention also provides a sweetener composition comprising at least one mogroside of the present invention. "Sweetener composition," as the term is used herein, refers to a mixture of at least one mogroside of the present invention and at least one other substance.

In a particular embodiment, the at least one other substance does not occur and/or is not admixed with the mogroside in nature. As such, these sweetener compositions do not occur in nature. In one embodiment, the at least one other substance modulates the taste profile of the at least one mogroside to provide a composition with a more sucrose-like taste profile compared to the mogroside in nature and (if applicable) the at least one other substance in nature. For example, in certain embodiments the composition exhibits one or more of the following characteristics: improved sweetness potency, improved mouthfeel, decreased sweetness linger, decreased bitterness and/or decreased metallic taste.

In one aspect, the sweetener composition comprises a mogroside of the present invention in a sweetening amount. "Sweetening amount", as used herein, refers to the amount of compound required to provide detectable sweetness when present in a consumable, e.g. a beverage and is also referred to as "sweetness recognition threshold".

In one embodiment, the sweetener composition provides a sucrose equivalence of greater than about 2% (w/v) when added to a sweetenable composition or sweetenable consumable, such as, for example, greater than about 3%, about 4%, about 5%, about 6%, about 7%, about 8%, about 9%, about 10%, about 11%, about 12%, about 13% or about 14%.

In certain embodiments, the sweetener composition comprises at least about 5% of a mogroside of the present invention by weight, such as, for example, at least about 10%, at least about 20%, at least about 30%, at least about 40%, at least about 50%, at least about 60%, at least about 70%, at least about 80%, at least about 90%, at least about 95% or at least about 97%.

In certain embodiments, the sweetener composition comprises at least about 5% of the at least one other substance (e.g. sweetener) by weight, such as, for example, at least about 10%, at least about 20%, at least about 30%, at least about 40%, at least about 50%, at least about 60%, at least about 70%, at least about 80%, at least about 90%, at least about 95% or at least about 97%.

In some embodiments, the at least one other substance is a sweetener, i.e. a sweetener composition is a sweetener blend or comprises a sweetener blend. Such sweetener compositions may provide a sucrose equivalence of greater than about 2% (w/v) when added to a sweetenable composition or sweetenable consumable, such as, for example, greater than about 3%, about 4%, about 5%, about 6%, about 7%, about 8%, about 9%, about 10%, about 11%, about 12%, about 13% or about 14%.

In one embodiment, the at least one other substance is a sweetener that is not the same as the mogroside of the present invention. The sweetener can be present in a sweetening amount.

In one embodiment, the at least one other substance is a natural high potency sweetener. As used herein, the phrase "natural high potency sweetener" refers to any sweetener found in a plant or other species without requiring further modification and that has a sweetness potency greater than sucrose, fructose, or glucose, yet has less calories. The natural high potency sweetener can be provided as a pure compound or, alternatively, as part of an extract.

In another embodiment, at least one other substance is a synthetic sweetener. As used herein, the phrase "synthetic sweetener" refers to any composition which is not found naturally in nature and characteristically has a sweetness potency greater than sucrose, fructose, or glucose, yet has less calories.

In still other embodiments, combinations of natural high potency sweeteners and synthetic sweeteners are contemplated.

In other embodiments, the at least one other substance is a carbohydrate sweetener. Suitable carbohydrate sweeteners are selected from, but not limited to, the group consisting of sucrose, glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheltulose, octolose, fucose, rhamnose, arabinose, turanose, sialose and combinations thereof.

Other suitable sweeteners include rebaudioside A, rebaudioside B, rebaudioside C, rebaudioside D, rebaudioside E, rebaudioside F, rebaudioside I, rebaudioside H, rebaudioside L, rebaudioside K, rebaudioside J, rebaudioside M, rebaudioside N, rebaudioside O, dulcoside A, dulcoside B, rubusoside, stevia, stevioside, mogroside IV, mogroside V, mogroside VI, Luo han guo, siamenoside I, mogroside IIIE, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, steviolbioside, hesperitin and cyclocarioside I, sugar alcohols such as erythritol, sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, glucosylated steviol glycosides (GSGs) and combinations thereof.

In a particular embodiment, the sweetener is at least one calorie-providing carbohydrate sweetener.

In one embodiment, the sweetener is a caloric sweetener or mixture of caloric sweeteners. In another embodiment, the caloric sweetener is selected from sucrose, fructose, glucose, high fructose corn/starch syrup, a beet sugar, a cane sugar, and combinations thereof.

In another embodiment, the sweetener is a rare sugar selected from allulose, sorbose, lyxose, ribulose, xylose, xylulose, D-allose, L-ribose, D-tagatose, L-glucose, L-fucose, L-arabinose, turanose, kojibiose and combinations thereof.

In one embodiment, the sweetener composition comprises at least one additional mogroside. The mogroside can be provided in pure form or as part of mixture, i.e. a mogroside blend. Exemplary mogrosides include, but are not limited to, any of grosmogroside I, mogroside IA, mogroside IE, 11-oxomogroside IA, mogroside II, mogroside IIA, mogroside IIB, mogroside II E, 7-oxomogroside IIE, mogroside III, mogroside IIIE, 11-oxomogroside IIIE, 11-deoxymogroside III, mogroside IV, Mogroside IVA 11-oxomogroside IV, 11-oxomogroside IVA, mogroside V, isomogroside V, 11-oxosiamenoside I, 11-deoxymogroside V, 7-oxomogroside V, 11-oxomogroside V, isomogroside V, mogroside VI, mogrol, 11-oxomogrol, siamenoside I, 11-oxosiamenosdie I, an isomer of siamenoside I (e.g. those disclosed in 20170119032; incorporated by reference in its entirety), in particular the 1,6-α isomer of siamenoside I and combinations thereof. Additional exemplary mogrosides include those described in U.S. Patent Application Publication 2016039864, the contents of which are incorporated by reference herein.

In one embodiment, the at least one additional substance is siamenoside I in a sweetening amount.

In another embodiment, the at least one additional substance is the 1,6-α isomer of siamenoside I (mogrol-3-O-[β-D-glucopyranoside]-24-O-{[β-D-glucopyranosyl-(1→2)]-[α-D-glucopyranosyl-(1→6)]-β-D-glucopyranoside}) in a sweetening amount.

In still another embodiment, the at least one additional substance is mogroside V in a sweetening amount.

In yet another embodiment, the at least one additional substance is Rebaudioside M in a sweetening amount.

In still another embodiment, the at least one additional substance is Rebaudioside A in a sweetening amount.

In a further embodiment, the at least one additional substance is Rebaudioside D in a sweetening amount.

IV. Taste Enhancing Compositions

In some embodiments, the mogroside of the present invention is a taste enhancer. For example, in some embodiments the at least one mogroside of the present invention modulates one or more taste attributes of a consumable sweetened with a non-sucrose sweetener, thus making the consumable taste more like a sucrose-sweetened consumable. Exemplary taste attribute modulations include increasing sweetness, decreasing or eliminating bitterness, decreasing or eliminating bitter linger, decreasing or eliminating sourness, decreasing or eliminating astringency, decreasing or eliminating saltiness, decreasing or eliminating metallic notes, improving mouthfeel, decreasing or eliminating sweetness linger, and increasing sweetness onset. Multiple taste attributes of the sweetener can be modulated simultaneously, such that the consumable, overall, has more sucrose-sweetened characteristics. Methods of quantifying improvement in sucrose-sweetened characteristics are known in the art and includes, e.g., taste testing and histogram mapping.

In a particular embodiment, the mogroside of the present invention is a sweetness enhancer or modifier. "Sweetness enhancer", as the term is used herein, refers to a compound that enhances, amplifies or potentiates the perception of sweetness of a consumable (e.g. a beverage) when said compound is present in the consumable in a concentration at or below the compound's sweetener recognition threshold, i.e. in a concentration at which compound does not contribute any noticeable sweet taste in the absence of additional sweetener(s).

"Sweetness modifier", as the term is used herein, refers to a compound that changes the taste properties (such as linger, off-notes, or the like) of sweetness of a consumable (e.g. a beverage) when said compound is present in the consumable in a concentration at or below the compound's sweetener recognition threshold.

The term "sweetness enhancer" is synonymous with the terms "sweet taste potentiator," "sweetness potentiator," "sweetness amplifier," and "sweetness intensifier."

In one embodiment, a mogroside of the present invention may be added directly to the consumable, i.e., not provided in the form of a composition but rather as compound, to enhance sweetness. In this embodiment, a mogroside of the present invention is added to the consumable at a concentration at or below its sweetness recognition threshold concentration, i.e., a sweetness enhancer. In a particular embodiment, a mogroside of the present invention is added to the consumable at a concentration below its sweetness recognition threshold concentration, i.e., a sweetness enhancer.

In certain embodiments, a mogroside of the present invention is a sweetness enhancer or modifier and is added to the consumable in an amount that will provide a concentration of the mogroside that is at least about 1%, at least about 5%, at least about 10%, at least about 15%, at least about 20%, at least about 25%, at least about 30%, at least about 35%, at least about 40%, at least about 45% or at least about 50% or more below its sweetness recognition threshold.

In some embodiments, the mogroside of the present invention enhances the sucrose equivalence (SE) of the consumable by at least about 0.5%, about 0.6%, about 0.7%, about 0.8%, about 0.9%, about 1.0%, about 1.5%, about 2.0%, about 2.5%, about 3.0%, about 4.0% or about 5.0%, when compared to the SE of the consumable in the absence of the mogroside of the present invention.

In other embodiments, at least one mogroside of the present invention may be added to the consumable in the form of a sweetness enhancing composition. "Sweetness enhancing composition," as the term is used herein, refers to a composition of the present invention—as described above—wherein the composition enhances, amplifies or potentiates the perception of sweetness of a consumable (e.g. a beverage) when a mogroside of the present invention is present in the sweetness enhancer composition in an amount that will provide a concentration of the mogroside that is at or below its sweetness recognition threshold when added to the consumable. In a particular embodiment, the mogroside of the present invention is present in an amount that will provide a concentration of the mogroside of the present invention that is below its sweetness recognition threshold.

It is contemplated that the sweetness enhancing composition can include one or more sweetness enhancers or modifiers in addition to at least one mogroside of the present invention. In one embodiment, the sweetness enhancing composition can include one additional sweetness enhancer. In other embodiments, the composition can include two or more additional sweetness enhancers. In embodiments where two or more sweetness enhancers or modifiers are utilized, each one should be present at or below its respective sweetness recognition threshold concentration.

The one or more other sweetness enhancers or modifiers are selected from, but not limited to, the group consisting of 2-hydroxybenzoic acid, 3-hydroxybenzoic acid, 4-hydroxybenzoic acid, 2,4-dihydroxybenzoic acid, 3,4-dihydroxybenzoic acid, 2,5-dihydroxybenzoic acid, 2,6-dihydroxybenzoic acid, 2,3,4-trihydroxybenzoic acid, 2,4,6-trihydroxybenzoic acid, 3-aminobenzoic acid, 4-aminobenzoic acid, 4-O-β-D-glucosyl-hesperetin dihydrochalcone, MG isomogrosaide V, 4-hydroxycinnamic acid, 4-methoxycinnamic acid, 1-(2-hydroxyphenyl)-3-(4-pyridyl)-1-propanone, 4-ethoxybenzonitrile, 2-methoxy-5-(phenoxymethyl)-phenol, 1-(2, 4-dihydroxyphenyl)-2-(3-methoxy-4-hydroxyphenyl)-ethanone, Hesperetin dihydrochalcone-4'-(3-D-glucoside, hesperetin, 2,3',6-trihydroxy-4'-methoxydihydrochalcone, N-(3'-methoxy-4'-hydroxybenzyl)-2,4,6-trihydroxybenzamide, 3'-7-dihydroxy-4'-methoxyflavan, phloretin, FEMA GRAS flavor 4669, FEMA GRAS flavor 4701, FEMA GRAS flavor 4720, FEMA GRAS flavor 4774, FEMA GRAS flavor 4708, FEMA GRAS flavor 4728, FEMA GRAS flavor 4601, FEMA GRAS flavor 4802, hesperitin dihydrochalcone, FEMA GRAS flavor 4872, FEMA GRAS flavor 4899, 4-amino-5-(cyclohexyloxy)-2-methylquinoline-3-carboxylic acid, rebaudioside M, rebaudioside N, rebaudioside O, rebaudioside C and combinations thereof.

In another particular embodiment, the mogroside of the present invention is a flavor enhancer. "Flavor enhancer", as the term is used herein, refers to a compound that enhances, amplifies or potentiates the perceptions of a flavor ingredient (i.e. any substance that provides sweetness, sourness, saltiness, savoriness, bitterness, metallic taste, etc.) when said compound is present in a consumable (e.g. a beverage) in a concentration at or below the compound's flavor recognition threshold, i.e. in a concentration at which compound does not contribute any noticeable flavor in the absence of any flavor ingredient(s). The term "flavor recognition threshold", as generally used herein, is the lowest known concentration of a compound that is perceivable by the human sense of taste as the particular flavor. The flavor recognition threshold concentration is specific for a particular compound, and can vary based on temperature, matrix, ingredients and/or flavor system.

The term "flavor enhancer" is synonymous with the terms "flavor potentiator," "flavor amplifier," and "flavor intensifier."

In one embodiment, at least one mogroside of the present invention is added directly to the consumable, i.e., not provided in the form of a composition but rather as a compound, to enhance a flavor. In this embodiment, the mogroside of the present invention is added to the consumable at a concentration at or below its flavor recognition threshold concentration, i.e., a flavor enhancer. In a particular embodiment, the mogroside of the present invention is added to the consumable at a concentration below its flavor recognition threshold concentration, i.e., a flavor enhancer.

The mogrosides of the present invention enhances the flavor of the consumable by at least about 0.5%, about 0.6%, about 0.7%, about 0.8%, about 0.9%, about 1.0%, about 1.5%, about 2.0%, about 2.5%, about 3.0%, about 4.0% or about 5.0%, when compared to the flavor of the consumable in the absence of the mogroside of the present invention.

In other embodiments, at least one mogroside of the present invention may be added to the consumable in the form of a flavor enhancing composition. "Flavor enhancing composition," as the term is used herein, refers to a mixture of at least one mogroside of the present invention and at least one flavor ingredient, wherein the at least one mogroside is admixed with the at least one flavor ingredient—wherein the composition enhances, amplifies or potentiates the perception of the flavor ingredient in a consumable (e.g. a beverage) when the at least one mogroside of the present invention is present in the flavor enhancer composition in an amount that will provide a concentration of the mogroside that is at or below its flavor recognition threshold when added to the consumable.

Addition of the flavor enhancing composition increases the detected flavor of the at least one flavor ingredient in the consumable compared to the detected flavor of the same ingredient in the consumable in the absence of the flavor enhancer. Without being bound by theory, the flavor enhancing composition likely does not contribute any noticeable taste to the consumable to which it is added because the flavor enhancer is present in the consumable in a concentration at or below the its flavor recognition threshold.

Suitable flavor ingredients include, but are not limited to, vanillin, vanilla extract, mango extract, cinnamon, citrus, coconut, ginger, viridiflorol, almond, menthol (including menthol without mint), grape skin extract, and grape seed extract. "Flavorant" and "flavoring ingredient" are synonymous and can include natural or synthetic substances or combinations thereof. Flavorants also include any other substance which imparts flavor and may include natural or non-natural (synthetic) substances which are safe for human or animals when used in a generally accepted range. Non-limiting examples of proprietary flavorants include Dohler™ Natural Flavoring Sweetness Enhancer K14323 (Dohler™, Darmstadt, Germany), Symrise™ Natural Flavor Mask for Sweeteners 161453 and 164126 (Symrise™, Holzminden, Germany), Natural Advantage™ Bitterness Blockers 1, 2, 9 and 10 (Natural Advantage™, Freehold, New Jersey, U.S.A.), and Sucramask™ (Creative Research Management, Stockton, California, U.S.A.).

In another embodiment, the flavor enhancing composition comprising at least one mogroside of the present invention enhances flavors (either individual flavors or the overall flavor) when added to the consumable. These flavors include, but are not limited to, fruit flavors, including tropical fruit flavors, and vanilla-caramel type flavors.

V. Additives

In another aspect, compositions described herein (i.e. the compositions described above and the consumables described below) may comprise one or more additional additives and/or functional ingredients.

Exemplary additives include, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, caffeine, flavorants and flavoring ingredients, astringent compounds, proteins or protein hydrolysates, surfactants, emulsifiers, plant extracts, flavonoids, alcohols, polymers and combinations thereof.

In one embodiment, the composition further comprises one or more polyols. The term "polyol", as used herein, refers to a molecule that contains more than one hydroxyl group. A polyol may be a diol, triol, or a tetraol which contains 2, 3, and 4 hydroxyl groups respectively. A polyol also may contain more than 4 hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group.

Non-limiting examples of polyols in some embodiments include maltitol, mannitol, sorbitol, lactitol, xylitol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, reduced glucose syrup, and sugar alcohols or any other carbohydrates capable of being reduced which do not adversely affect taste.

Suitable amino acid additives include, but are not limited to, aspartic acid, arginine, glycine, glutamic acid, proline, threonine, theanine, cysteine, cystine, alanine, valine, tyrosine, leucine, arabinose, trans-4-hydroxyproline, isoleucine, asparagine, serine, lysine, histidine, ornithine, methionine, carnitine, aminobutyric acid (α-, β-, and/or δ-isomers), glutamine, hydroxyproline, taurine, norvaline, sarcosine, and their salt forms such as sodium or potassium salts or acid salts. The amino acid additives also may be in the D- or L-configuration and in the mono-, di-, or tri-form of the same or different amino acids. Additionally, the amino acids may be α-, β-, γ- and/or δ-isomers if appropriate. Combinations of the foregoing amino acids and their corresponding salts (e.g., sodium, potassium, calcium, magnesium salts or other alkali or alkaline earth metal salts thereof, or acid salts) also are suitable additives in some embodiments. The amino acids may be natural or synthetic. The amino acids also may be modified. Modified amino acids refers to any amino acid wherein at least one atom has been added, removed, substituted, or combinations thereof (e.g., N-alkyl amino acid, N-acyl amino acid, or N-methyl amino acid). Non-limiting examples of modified amino acids include amino acid derivatives such as trimethyl glycine, N-methyl-glycine, and N-methyl-alanine. As used herein, modified amino acids encompass both modified and unmodified amino acids. As used herein, amino acids also encompass both peptides and polypeptides (e.g., dipeptides, tripeptides, tetrapeptides, and pentapeptides) such as glutathione and L-alanyl-L-glutamine. Suitable polyamino acid additives include poly-L-aspartic acid, poly-L-lysine (e.g., poly-L-α-lysine or poly-L-ε-lysine), poly-L-ornithine (e.g., poly-L-α-ornithine or poly-L-ε-ornithine), poly-L-arginine, other polymeric forms of amino acids, and salt forms thereof (e.g., calcium, potassium, sodium, or magnesium salts such as L-glutamic acid mono sodium salt). The poly-amino acid additives also may be in the D- or L-configuration. Additionally, the poly-amino acids may be α-, β-, γ-, δ-, and ε-isomers if appropriate. Combinations of the foregoing poly-amino acids and their corresponding salts (e.g., sodium, potassium, calcium, magnesium salts or other alkali or alkaline earth metal salts thereof or acid salts) also are suitable additives in some embodiments. The poly-amino acids described herein also may comprise co-polymers of different amino acids. The poly-amino acids may be natural or synthetic. The poly-amino acids also may be modified, such that at least one atom has been added, removed, substituted, or combinations thereof (e.g., N-alkyl poly-amino acid or N-acyl poly-amino acid). As used herein, poly-amino acids encompass both modified and unmodified poly-amino acids. For example, modified poly-amino acids include, but are not limited to, poly-amino acids of various molecular weights (MW), such as poly-L-α-lysine with a MW of 1,500, MW of 6,000, MW of 25,200, MW of 63,000, MW of 83,000, or MW of 300,000.

Suitable sugar acid additives include, but are not limited to, aldonic, uronic, aldaric, alginic, gluconic, glucuronic, glucaric, galactaric, galacturonic, and salts thereof (e.g., sodium, potassium, calcium, magnesium salts or other physiologically acceptable salts), and combinations thereof.

Suitable nucleotide additives include, but are not limited to, inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, alkali or alkaline earth metal salts thereof, and combinations thereof. The nucleotides described herein also may comprise nucleotide-related additives, such as nucleosides or nucleic acid bases (e.g., guanine, cytosine, adenine, thymine, uracil).

Suitable organic acid additives include any compound which comprises a —COOH moiety, such as, for example, C2-C30 carboxylic acids, substituted hydroxyl C2-C30 carboxylic acids, butyric acid (ethyl esters), substituted butyric acid (ethyl esters), benzoic acid, substituted benzoic acids (e.g., 2,4-dihydroxybenzoic acid), substituted cinnamic acids, hydroxyacids, substituted hydroxybenzoic acids, anisic acid substituted cyclohexyl carboxylic acids, tannic acid, aconitic acid, lactic acid, tartaric acid, citric acid, isocitric acid, gluconic acid, glucoheptonic acids, adipic acid, hydroxycitric acid, malic acid, fruitaric acid (a blend of malic, fumaric, and tartaric acids), fumaric acid, maleic acid, succinic acid, chlorogenic acid, salicylic acid, creatine, caffeic acid, bile acids, acetic acid, ascorbic acid, alginic acid, erythorbic acid, polyglutamic acid, glucono delta lactone, and their alkali or alkaline earth metal salt derivatives thereof. In addition, the organic acid additives also may be in either the D- or L-configuration.

Suitable organic acid additive salts include, but are not limited to, sodium, calcium, potassium, and magnesium salts of all organic acids, such as salts of citric acid, malic acid, tartaric acid, fumaric acid, lactic acid (e.g., sodium lactate), alginic acid (e.g., sodium alginate), ascorbic acid (e.g., sodium ascorbate), benzoic acid (e.g., sodium benzoate or potassium benzoate), sorbic acid and adipic acid. The examples of the organic acid additives described optionally may be substituted with at least one group chosen from hydrogen, alkyl, alkenyl, alkynyl, halo, haloalkyl, carboxyl, acyl, acyloxy, amino, amido, carboxyl derivatives, alkylamino, dialkylamino, arylamino, alkoxy, aryloxy, nitro, cyano, sulfo, thiol, imine, sulfonyl, sulfenyl, sulfinyl, sulfamyl, carboxalkoxy, carboxamido, phosphonyl, phosphinyl, phosphoryl, phosphino, thioester, thioether, anhydride, oximino, hydrazino, carbamyl, phosphor or phosphonato.

Suitable inorganic acid additives include, but are not limited to, phosphoric acid, phosphorous acid, polyphosphoric acid, hydrochloric acid, sulfuric acid, carbonic acid, sodium dihydrogen phosphate, and alkali or alkaline earth metal salts thereof (e.g., inositol hexaphosphate Mg/Ca).

Suitable bitter compound additives include, but are not limited to, caffeine, quinine, urea, bitter orange oil, naringin, quassia, and salts thereof.

Suitable flavorants and flavoring ingredient additives include, but are not limited to, vanillin, vanilla extract, mango extract, cinnamon, citrus, coconut, ginger, viridiflorol, almond, menthol (including menthol without mint), grape skin extract, and grape seed extract. “Flavorant” and “flavoring ingredient” are synonymous and can include natural or synthetic substances or combinations thereof. Flavorants also include any other substance which imparts flavor and may include natural or non-natural (synthetic) substances which are safe for human or animals when used in a generally accepted range. Non-limiting examples of proprietary flavorants include Dohler™ Natural Flavoring Sweetness Enhancer K14323 (Dohler™, Darmstadt, Germany), Symrise™ Natural Flavor Mask for Sweeteners 161453 and 164126 (Symrise™, Holzminden, Germany), Natural Advantage™ Bitterness Blockers 1, 2, 9 and 10 (Natural Advantage™ Freehold, New Jersey, U.S.A.), and Sucramask™ (Creative Research Management, Stockton, California, U.S.A.).

Suitable polymer additives include, but are not limited to, chitosan, pectin, pectic, pectinic, polyuronic, polygalacturonic acid, starch, food hydrocolloid or crude extracts thereof (e.g., gum acacia senegal (Fibergum™), gum acacia seyal, carageenan), poly-L-lysine (e.g., poly-L-α-lysine or poly-L-ε-lysine), poly-L-ornithine (e.g., poly-L-α-ornithine or poly-L-ε-ornithine), polypropylene glycol, polyethylene glycol, poly(ethylene glycol methyl ether), polyarginine, polyaspartic acid, polyglutamic acid, polyethylene imine, alginic acid, sodium alginate, propylene glycol alginate, and sodium polyethyleneglycolalginate, sodium hexametaphosphate and its salts, and other cationic polymers and anionic polymers.

Suitable protein or protein hydrolysate additives include, but are not limited to, bovine serum albumin (BSA), whey protein (including fractions or concentrates thereof such as 90% instant whey protein isolate, 34% whey protein, 50% hydrolyzed whey protein, and 80% whey protein concentrate), soluble rice protein, soy protein, protein isolates, protein hydrolysates, reaction products of protein hydrolysates, glycoproteins, and/or proteoglycans containing amino acids (e.g., glycine, alanine, serine, threonine, asparagine, glutamine, arginine, valine, isoleucine, leucine, norvaline, methionine, proline, tyrosine, hydroxyproline, and the like), collagen (e.g., gelatin), partially hydrolyzed collagen (e.g., hydrolyzed fish collagen), and collagen hydrolysates (e.g., porcine collagen hydrolysate).

Suitable surfactant additives include, but are not limited to, polysorbates (e.g., polyoxyethylene sorbitan monooleate (polysorbate 80), polysorbate 20, polysorbate 60), sodium dodecylbenzenesulfonate, dioctyl sulfosuccinate or dioctyl sulfosuccinate sodium, sodium dodecyl sulfate, cetylpyridinium chloride (hexadecylpyridinium chloride), hexadecyltrimethylammonium bromide, sodium cholate, carbamoyl, choline chloride, sodium glycocholate, sodium taurodeoxycholate, lauric arginate, sodium stearoyl lactylate, sodium taurocholate, lecithins, sucrose oleate esters, sucrose stearate esters, sucrose palmitate esters, sucrose laurate esters, and other emulsifiers, and the like.

Suitable flavonoid additives are classified as flavonols, flavones, flavanones, flavan-3-ols, isoflavones, or anthocyanidins. Non-limiting examples of flavonoid additives include, but are not limited to, catechins (e.g., green tea extracts such as Polyphenon™ 60, Polyphenon™ 30, and Polyphenon™ 25 (Mitsui Norin Co., Ltd., Japan), polyphenols, rutins (e.g., enzyme modified rutin Sanmelin™ AO (San-fi Gen F.F.I., Inc., Osaka, Japan)), neohesperidin, naringin, neohesperidin dihydrochalcone, and the like.

Suitable alcohol additives include, but are not limited to, ethanol.

Suitable astringent compound additives include, but are not limited to, tannic acid, europium chloride ($EuCl_3$), gadolinium chloride ($GdCl_3$), terbium chloride ($TbCl_3$), alum, tannic acid, and polyphenols (e.g., tea polyphenols).

The compositions provided herein can also contain one or more functional ingredients, which provide a real or perceived heath benefit to the composition. Functional ingredients include, but are not limited to, saponins, antioxidants, dietary fiber sources, fatty acids, vitamins, glucosamine, minerals, preservatives, hydration agents, probiotics, prebiotics, postbiotics, weight management agents, osteoporosis management agents, phytoestrogens, long chain primary aliphatic saturated alcohols, phytosterols and combinations thereof.

Exemplary functional ingredients include, but are not limited to, saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

In certain embodiments, the functional ingredient is at least one saponin. As used herein, the at least one saponin may comprise a single saponin or a plurality of saponins as a functional ingredient for the composition provided herein. Saponins are glycosidic natural plant products comprising an aglycone ring structure and one or more sugar moieties.

Non-limiting examples of specific saponins for use in particular embodiments of the invention include group A acetyl saponin, group B acetyl saponin and group E acetyl saponin. Several common sources of saponins include soybeans, which have approximately 5% saponin content by dry weight, soapwort plants (*Saponaria*), the root of which was used historically as soap, as well as alfalfa, aloe, asparagus, grapes, chickpeas, yucca, and various other beans and weeds. Saponins may be obtained from these sources by using extraction techniques well known to those of ordinary skill in the art. A description of conventional extraction techniques can be found in U.S. Pat. Appl. No. 2005/0123662, the disclosure of which is expressly incorporated by reference.

In certain embodiments, the functional ingredient is at least one antioxidant. As used herein "antioxidant" refers to any substance which inhibits, suppresses, or reduces oxidative damage to cells and biomolecules. Examples of suitable antioxidants for embodiments of this invention include, but are not limited to, vitamins, vitamin cofactors, minerals, hormones, carotenoids, carotenoid terpenoids, non-carotenoid terpenoids, flavonoids, flavonoid polyphenolics (e.g., bioflavonoids), flavonols, flavones, phenols, polyphenols, esters of phenols, esters of polyphenols, nonflavonoid phenolics, isothiocyanates, and combinations thereof. In some embodiments, the antioxidant is vitamin A, vitamin C, vitamin E, ubiquinone, mineral selenium, manganese, melatonin, α-carotene, β-carotene, lycopene, lutein, zeanthin, crypoxanthin, reservatol, eugenol, quercetin, catechin, gossypol, hesperetin, curcumin, ferulic acid, thymol, hydroxytyrosol, tumeric, thyme, olive oil, lipoic acid, glutathinone, gutamine, oxalic acid, tocopherol-derived compounds, butylated hydroxyanisole (BHA), butylated hydroxytoluene (BHT), ethylenediaminetetraacetic acid (EDTA), tert-butylhydroquinone, acetic acid, pectin, tocotrienol, tocopherol, coenzyme Q10, zeaxanthin, astaxanthin, canthaxantin, saponins, limonoids, kaempfedrol, myricetin, isorhamnetin, proanthocyanidins, quercetin, rutin, luteolin, apigenin, tangeritin, hesperetin, naringenin, erodictyol, flavan-3-ols (e.g., anthocyanidins), gallocatechins, epicatechin and its gallate forms, epigallocatechin and its gallate forms (ECGC) theaflavin and its gallate forms, thearubigins, isoflavone, phytoestrogens, genistein, daidzein, glycitein, anythocyanins, cyaniding, delphinidin, malvidin, pelargonidin, peonidin, petunidin, ellagic acid, gallic acid, salicylic acid, rosmarinic acid, cinnamic acid and its derivatives (e.g., ferulic acid), chlorogenic acid, chicoric acid, gallotannins, ellagitannins, anthoxanthins, betacyanins and other plant pigments, silymarin, citric acid, lignan, antinutrients, bilirubin, uric acid, R-□-lipoic acid, N-acetylcysteine, emblicanin, apple extract, apple skin extract (applephenon), rooibos extract red, rooibos extract, green, hawthorn berry extract, red raspberry extract, green coffee antioxidant (GCA), aronia extract 20%, grape seed extract (VinOseed), cocoa extract, hops extract, mangosteen extract, mangosteen hull extract, cranberry extract, pomegranate extract, pomegranate hull extract, pomegranate seed extract, hawthorn berry extract, pomella pomegranate extract, cinnamon bark extract, grape skin extract, bilberry extract, pine bark extract, pycnogenol, elderberry extract, mulberry root extract, wolfberry (gogi) extract, blackberry extract, blueberry extract, blueberry leaf extract, raspberry extract, turmeric extract, citrus bioflavonoids, black currant, ginger, acai powder, green coffee bean extract, green tea extract, and phytic acid, or combinations thereof. In alternate embodiments, the antioxidant is a synthetic antioxidant such as butylated hydroxytolune or butylated hydroxyanisole, for example. Other sources of suitable antioxidants for embodiments of this invention include, but are not limited to, fruits, vegetables, tea, cocoa, chocolate, spices, herbs, rice, organ meats from livestock, yeast, whole grains or cereal grains.

Particular antioxidants belong to the class of phytonutrients called polyphenols (also known as "polyphenolics"), which are a group of chemical substances found in plants, characterized by the presence of more than one phenol group per molecule. A variety of health benefits may be derived from polyphenols, including prevention of cancer, heart disease, and chronic inflammatory disease and improved mental strength and physical strength, for example. Suitable polyphenols for embodiments of this invention include catechins, proanthocyanidins, procyanidins, anthocyanins, quercerin, rutin, reservatrol, isoflavones, curcumin, punicalagin, ellagitannin, hesperidin, naringin, citrus flavonoids, chlorogenic acid, other similar materials and combinations thereof.

In particular embodiments, the antioxidant is a catechin such as, for example, epigallocatechin gallate (EGCG). In another embodiment, the antioxidant is chosen from proanthocyanidins, procyanidins or combinations thereof. In particular embodiments, the antioxidant is an anthocyanin. In still other embodiments, the antioxidant is chosen from quercetin, rutin or combinations thereof. In yet other embodiments, the antioxidant is reservatrol. In still further embodiments, the antioxidant is an isoflavone. In yet further embodiments, the antioxidant is curcumin. In other embodiments, the antioxidant is chosen from punicalagin, ellagitannin or combinations thereof. In still other embodiments, the antioxidant is chlorogenic acid.

In certain embodiments, the functional ingredient is at least one dietary fiber source. Numerous polymeric carbohydrates having significantly different structures in both composition and linkages fall within the definition of dietary fiber. Such compounds are well known to those skilled in the art, non-limiting examples of which include non-starch polysaccharides, lignin, cellulose, methylcellulose, the hemicelluloses, β-glucans, pectins, gums, mucilage, waxes, inulins, oligosaccharides, fructooligosaccharides, cyclodextrins, chitins and combinations thereof. Although dietary fiber generally is derived from plant sources, indigestible animal products such as chitins are also classified as dietary fiber. Chitin is a polysaccharide composed of units of acetylglucosamine joined by β(1-4) linkages, similar to the linkages of cellulose.

In certain embodiments, the functional ingredient is at least one fatty acid. As used herein, "fatty acid" refers to any straight chain monocarboxylic acid and includes saturated fatty acids, unsaturated fatty acids, long chain fatty acids, medium chain fatty acids, short chain fatty acids, fatty acid precursors (including omega-9 fatty acid precursors), and esterified fatty acids. As used herein, "long chain polyunsaturated fatty acid" refers to any polyunsaturated carboxylic acid or organic acid with a long aliphatic tail. As used herein, "omega-3 fatty acid" refers to any polyunsaturated fatty acid having a first double bond as the third carbon-carbon bond from the terminal methyl end of its carbon chain. In particular embodiments, the omega-3 fatty acid may comprise a long chain omega-3 fatty acid. As used herein, "omega-6 fatty acid" any polyunsaturated fatty acid having a first double bond as the sixth carbon-carbon bond from the terminal methyl end of its carbon chain.

Suitable omega-3 fatty acids for use in embodiments of the present invention can be derived from algae, fish, animals, plants, or combinations thereof, for example. Examples of suitable omega-3 fatty acids include, but are not limited to, linolenic acid, alpha-linolenic acid, eicosapentaenoic acid, docosahexaenoic acid, stearidonic acid, eicosatetraenoic acid and combinations thereof. In some embodiments, suitable omega-3 fatty acids can be provided in fish oils, (e.g., menhaden oil, tuna oil, salmon oil, bonito oil, and cod oil), microalgae omega-3 oils or combinations thereof. In particular embodiments, suitable omega-3 fatty acids may be derived from commercially available omega-3 fatty acid oils such as Microalgae DHA oil (from Martek, Columbia, MD), OmegaPure (from Omega Protein, Houston, TX), Marinol C-38 (from Lipid Nutrition, Channahon, IL), Bonito oil and MEG-3 (from Ocean Nutrition, Dartmouth, NS), Evogel (from Symrise, Holzminden, Germany), Marine Oil, from tuna or salmon (from Arista Wilton, CT), OmegaSource 2000, Marine Oil, from menhaden and Marine Oil, from cod (from OmegaSource, RTP, NC).

Suitable omega-6 fatty acids include, but are not limited to, linoleic acid, gamma-linolenic acid, dihommo-gamma-linolenic acid, arachidonic acid, eicosadienoic acid, docosadienoic acid, adrenic acid, docosapentaenoic acid and combinations thereof.

Suitable esterified fatty acids for embodiments of the present invention may include, but are not limited to, monoacylgycerols containing omega-3 and/or omega-6 fatty acids, diacylgycerols containing omega-3 and/or omega-6 fatty acids, or triacylgycerols containing omega-3 and/or omega-6 fatty acids and combinations thereof.

In certain embodiments, the functional ingredient is at least one vitamin. Suitable vitamins include vitamin A, vitamin D, vitamin E, vitamin K, vitamin B1, vitamin B2, vitamin B3, vitamin B5, vitamin B6, vitamin B7, vitamin B9, vitamin B12, and vitamin C.

Various other compounds have been classified as vitamins by some authorities. These compounds may be termed pseudo-vitamins and include, but are not limited to, compounds such as ubiquinone (coenzyme Q10), pangamic acid, dimethylglycine, taestrile, amygdaline, flavanoids, para-aminobenzoic acid, adenine, adenylic acid, and s-methylmethionine. As used herein, the term vitamin includes pseudo-vitamins. In some embodiments, the vitamin is a fat-soluble vitamin chosen from vitamin A, D, E, K and combinations thereof. In other embodiments, the vitamin is a water-soluble vitamin chosen from vitamin B1, vitamin B2, vitamin B3, vitamin B6, vitamin B12, folic acid, biotin, pantothenic acid, vitamin C and combinations thereof.

In certain embodiments, the functional ingredient is glucosamine, optionally further comprising chondroitin sulfate.

In certain embodiments, the functional ingredient is at least one mineral. Minerals, in accordance with the teachings of this invention, comprise inorganic chemical elements required by living organisms. Minerals are comprised of a broad range of compositions (e.g., elements, simple salts, and complex silicates) and also vary broadly in crystalline structure. They may naturally occur in foods and beverages, may be added as a supplement, or may be consumed or administered separately from foods or beverages.

Minerals may be categorized as either bulk minerals, which are required in relatively large amounts, or trace minerals, which are required in relatively small amounts. Bulk minerals generally are required in amounts greater than or equal to about 100 mg per day and trace minerals are those that are required in amounts less than about 100 mg per day.

In one embodiment, the mineral is chosen from bulk minerals, trace minerals or combinations thereof. Non-limiting examples of bulk minerals include calcium, chlorine, magnesium, phosphorous, potassium, sodium, and sulfur. Non-limiting examples of trace minerals include chromium, cobalt, copper, fluorine, iron, manganese, molybdenum, selenium, zinc, and iodine. Although iodine generally is classified as a trace mineral, it is required in larger quantities than other trace minerals and often is categorized as a bulk mineral.

In a particular embodiment, the mineral is a trace mineral, believed to be necessary for human nutrition, non-limiting examples of which include bismuth, boron, lithium, nickel, rubidium, silicon, strontium, tellurium, tin, titanium, tungsten, and vanadium.

The minerals embodied herein may be in any form known to those of ordinary skill in the art. For example, in a particular embodiment the minerals may be in their ionic form, having either a positive or negative charge. In another particular embodiment the minerals may be in their molecular form. For example, sulfur and phosphorous often are found naturally as sulfates, sulfides, and phosphates.

In certain embodiments, the functional ingredient is at least one preservative. In particular embodiments of this invention, the preservative is chosen from antimicrobials, antioxidants, antienzymatics or combinations thereof. Non-limiting examples of antimicrobials include sulfites, propionates, benzoates, sorbates, nitrates, nitrites, bacteriocins, salts, sugars, acetic acid, dimethyl dicarbonate (DMDC), ethanol, and ozone. In one embodiment, the preservative is a sulfite. Sulfites include, but are not limited to, sulfur dioxide, sodium bisulfite, and potassium hydrogen sulfite. In another embodiment, the preservative is a propionate. Propionates include, but are not limited to, propionic acid, calcium propionate, and sodium propionate. In yet another embodiment, the preservative is a benzoate. Benzoates include, but are not limited to, sodium benzoate and benzoic acid. In a still further embodiment, the preservative is a sorbate. Sorbates include, but are not limited to, potassium sorbate, sodium sorbate, calcium sorbate, and sorbic acid. In a yet further embodiment, the preservative is a nitrate and/or a nitrite. Nitrates and nitrites include, but are not limited to, sodium nitrate and sodium nitrite. In another embodiment, the at least one preservative is a bacteriocin, such as, for example, nisin. In a further embodiment, the preservative is ethanol. In still another embodiment, the preservative is ozone. Non-limiting examples of antienzymatics suitable for use as preservatives in particular embodiments of the invention include ascorbic acid, citric acid, and metal chelating agents such as ethylenediaminetetraacetic acid (EDTA).

In certain embodiments, the functional ingredient is at least one hydration agent. In a particular embodiment, the hydration agent is an electrolyte. Non-limiting examples of electrolytes include sodium, potassium, calcium, magnesium, chloride, phosphate, bicarbonate, and combinations thereof. Suitable electrolytes for use in particular embodiments of this invention are also described in U.S. Pat. No. 5,681,569, the disclosure of which is expressly incorporated herein by reference. In one embodiment, the electrolyte is obtained from their corresponding water-soluble salt. Non-limiting examples of salts for use in particular embodiments include chlorides, carbonates, sulfates, acetates, bicarbonates, citrates, phosphates, hydrogen phosphates, tartrates, sorbates, citrates, benzoates, or combinations thereof. In other embodiments, the electrolytes are provided by juice, fruit extracts, vegetable extracts, tea, or teas extracts.

In particular embodiments of this invention, the hydration agent is a carbohydrate to supplement energy stores burned by muscles. Suitable carbohydrates for use in particular embodiments of this invention are described in U.S. Pat. Nos. 4,312,856, 4,853,237, 5,681,569, and 6,989,171, the disclosures of which are expressly incorporated herein by reference. Non-limiting examples of suitable carbohydrates include monosaccharides, disaccharides, oligosaccharides, complex polysaccharides or combinations thereof. Non-limiting examples of suitable types of monosaccharides for use in particular embodiments include trioses, tetroses, pentoses, hexoses, heptoses, octoses, and nonoses. Non-limiting examples of specific types of suitable monosaccharides include glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheltulose, octolose, and sialose. Non-limiting examples of suitable disaccharides include sucrose, lactose, and maltose. Non-limiting examples of suitable oligosaccharides include saccharose, maltotriose, and maltodextrin. In other particular embodiments, the carbohydrates are provided by a corn syrup, a beet sugar, a cane sugar, a juice, or a tea.

In another particular embodiment, the hydration agent is a flavanol that provides cellular rehydration. Flavanols are a class of natural substances present in plants, and generally comprise a 2-phenylbenzopyrone molecular skeleton attached to one or more chemical moieties. Non-limiting examples of suitable flavanols for use in particular embodiments of this invention include catechin, epicatechin, gallocatechin, epigallocatechin, epicatechin gallate, epigallocatechin 3-gallate, theaflavin, theaflavin 3-gallate, theaflavin 3'-gallate, theaflavin 3,3' gallate, thearubigin or combinations thereof. Several common sources of flavanols include tea plants, fruits, vegetables, and flowers. In preferred embodiments, the flavanol is extracted from green tea.

In a particular embodiment, the hydration agent is a glycerol solution to enhance exercise endurance. The ingestion of a glycerol containing solution has been shown to provide beneficial physiological effects, such as expanded blood volume, lower heart rate, and lower rectal temperature.

In certain embodiments, the functional ingredient is chosen from at least one probiotic, prebiotic and combination thereof. The probiotic is a beneficial microorganisms that affects the human body's naturally-occurring gastrointestinal microflora. Examples of probiotics include, but are not limited to, bacteria of the genus Lactobacilli, Bifidobacteria, Streptococci, or combinations thereof, that confer beneficial effects to humans. In particular embodiments of the invention, the at least one probiotic is chosen from the genus Lactobacilli. According to other particular embodiments of this invention, the probiotic is chosen from the genus Bifidobacteria. According to still other particular embodiments of this invention, the probiotic is chosen from the genus *Streptococcus.*

Probiotics that may be used in accordance with this invention are well-known to those of skill in the art. Non-limiting examples of foodstuffs comprising probiotics include yogurt, sauerkraut, kefir, kimchi, fermented vegetables, and other foodstuffs containing a microbial element that beneficially affects the host animal by improving the intestinal microbalance.

Prebiotics, in accordance with the teachings of this invention, include, without limitation, mucopolysaccharides, oligosaccharides, polysaccharides, amino acids, vitamins, nutrient precursors, proteins and combinations thereof. According to a particular embodiment of this invention, the prebiotic is chosen from dietary fibers, including, without limitation, polysaccharides and oligosaccharides. Non-limiting examples of oligosaccharides that are categorized as prebiotics in accordance with particular embodiments of this invention include fructooligosaccharides, inulins, isomalto-oligosaccharides, lactilol, lactosucrose, lactulose, pyrodextrins, soy oligosaccharides, transgalacto-oligosaccharides, and xylo-oligosaccharides. In other embodiments, the prebiotic is an amino acid. Although a number of known prebiotics break down to provide carbohydrates for probiotics, some probiotics also require amino acids for nourishment.

Prebiotics are found naturally in a variety of foods including, without limitation, bananas, berries, asparagus, garlic, wheat, oats, barley (and other whole grains), flaxseed, tomatoes, Jerusalem artichoke, onions and chicory, greens (e.g., dandelion greens, spinach, collard greens, chard, kale, mustard greens, turnip greens), and legumes (e.g., lentils, kidney beans, chickpeas, navy beans, white beans, black beans).

In certain embodiments, the functional ingredient is at least one weight management agent.

As used herein, "a weight management agent" includes an appetite suppressant and/or a thermogenesis agent. As used herein, the phrases "appetite suppressant", "appetite satiation compositions", "satiety agents", and "satiety ingredients" are synonymous. The phrase "appetite suppressant" describes macronutrients, herbal extracts, exogenous hormones, anorectics, anorexigenics, pharmaceutical drugs, and combinations thereof, that when delivered in an effective amount, suppress, inhibit, reduce, or otherwise curtail a person's appetite. The phrase "thermogenesis agent" describes macronutrients, herbal extracts, exogenous hormones, anorectics, anorexigenics, pharmaceutical drugs, and combinations thereof, that when delivered in an effective amount, activate or otherwise enhance a person's thermogenesis or metabolism.

Suitable weight management agents include macronutrient selected from the group consisting of proteins, carbohydrates, dietary fats, and combinations thereof. Consumption of proteins, carbohydrates, and dietary fats stimulates the release of peptides with appetite-suppressing effects. For example, consumption of proteins and dietary fats stimulates the release of the gut hormone cholecytokinin (CCK), while consumption of carbohydrates and dietary fats stimulates release of Glucagon-like peptide 1 (GLP-1).

Suitable macronutrient weight management agents also include carbohydrates. Carbohydrates generally comprise sugars, starches, cellulose and gums that the body converts into glucose for energy. Carbohydrates often are classified into two categories, digestible carbohydrates (e.g., monosaccharides, disaccharides, and starch) and non-digestible carbohydrates (e.g., dietary fiber). Studies have shown that non-digestible carbohydrates and complex polymeric carbohydrates having reduced absorption and digestibility in the small intestine stimulate physiologic responses that inhibit food intake. Accordingly, the carbohydrates embodied herein desirably comprise non-digestible carbohydrates or carbohydrates with reduced digestibility. Non-limiting examples of such carbohydrates include polydextrose; inulin; monosaccharide-derived polyols such as erythritol, mannitol, xylitol, and sorbitol; disaccharide-derived alcohols such as isomalt, lactitol, and maltitol; and hydrogenated starch hydrolysates. Carbohydrates are described in more detail herein below.

In another particular embodiment weight management agent is a dietary fat. Dietary fats are lipids comprising combinations of saturated and unsaturated fatty acids. Polyunsaturated fatty acids have been shown to have a greater satiating power than mono-unsaturated fatty acids.

Accordingly, the dietary fats embodied herein desirably comprise poly-unsaturated fatty acids, non-limiting examples of which include triacylglycerols.

In a particular embodiment, the weight management agent is an herbal extract. Extracts from numerous types of plants have been identified as possessing appetite suppressant properties. Non-limiting examples of plants whose extracts have appetite suppressant properties include plants of the genus *Hoodia, Trichocaulon, Caralluma, Stapelia, Orbea, Asclepias, and Camelia*. Other embodiments include extracts derived from *Gymnema sylvestre*, Kola Nut, Citrus Auran tium, Yerba Mate, *Griffonia simplicifolia*, Guarana, myrrh, guggul Lipid, and black current seed oil.

The herbal extracts may be prepared from any type of plant material or plant biomass. Non-limiting examples of plant material and biomass include the stems, roots, leaves, dried powder obtained from the plant material, and sap or dried sap. The herbal extracts generally are prepared by extracting sap from the plant and then spray-drying the sap. Alternatively, solvent extraction procedures may be employed. Following the initial extraction, it may be desirable to further fractionate the initial extract (e.g., by column chromatography) in order to obtain an herbal extract with enhanced activity. Such techniques are well known to those of ordinary skill in the art.

In a particular embodiment, the herbal extract is derived from a plant of the genus Hoodia, species of which include *H. alstonii, H. currorii, H. dregei, H. flava, H. gordonii, H. jutatae, H. mossamedensis, H. officinalis, H. parviflorai, H. pedicellata, H. pilifera, H. ruschii*, and *H. triebneri*. Hoodia plants are stem succulents native to southern Africa. A sterol glycoside of Hoodia, known as P57, is believed to be responsible for the appetite-suppressant effect of the Hoodia species. In another particular embodiment, the herbal extract is derived from a plant of the genus *Caralluma*, species of which include *C. indica, C. fimbriata, C. attenuate, C. tuberculata, C. edulis, C. adscendens, C. stalagmifera, C. umbellate, C. penicillata, C. russeliana, C. retrospicens, C. Arabica, and C. lasiantha. Carralluma* plants belong to the same Subfamily as Hoodia, Asclepiadaceae. *Caralluma* are small, erect and fleshy plants native to India having medicinal properties, such as appetite suppression, that generally are attributed to glycosides belonging to the pregnane group of glycosides, non-limiting examples of which include caratuberside A, caratuberside B, bouceroside I, bouceroside II, bouceroside III, bouceroside IV, bouceroside V, bouceroside VI, bouceroside VII, bouceroside VIII, bouceroside IX, and bouceroside X. In another particular embodiment, the at least one herbal extract is derived from a plant of the genus Trichocaulon. Trichocaulon plants are succulents that generally are native to southern Africa, similar to Hoodia, and include the species *T. piliferum* and *T. officinale*. In another particular embodiment, the herbal extract is derived from a plant of the genus *Stapelia* or *Orbea*, species of which include *S. gigantean* and *O. variegate*, respectively. Both *Stapelia* and *Orbea* plants belong to the same Subfamily as Hoodia, Asclepiadaceae. Not wishing to be bound by any theory, it is believed that the compounds exhibiting appetite suppressant activity are saponins, such as pregnane glycosides, which include stavarosides A, B, C, D, E, F, G, H, I, J, and K. In another particular embodiment, the herbal extract is derived from a plant of the genus *Asclepias. Asclepias* plants also belong to the Asclepiadaceae family of plants. Non-limiting examples of *Asclepias* plants include *A. incarnate, A. curassayica, A. syriaca*, and *A. tuberose*. Not wishing to be bound by any theory, it is believed that the extracts comprise steroidal compounds, such as pregnane glycosides and pregnane aglycone, having appetite suppressant effects.

In a particular embodiment, the weight management agent is an exogenous hormone having a weight management effect. Non-limiting examples of such hormones include CCK, peptide YY, ghrelin, bombesin and gastrin-releasing peptide (GRP), enterostatin, apolipoprotein A-IV, GLP-1, amylin, somastatin, and leptin.

In another embodiment, the weight management agent is a pharmaceutical drug. Non-limiting examples include phentenime, diethylpropion, phendimetrazine, sibutramine, rimonabant, oxyntomodulin, floxetine hydrochloride, ephedrine, phenethylamine, or other stimulants.

In certain embodiments, the functional ingredient is at least one osteoporosis management agent. In certain embodiments, the osteoporosis management agent is at least one calcium source. According to a particular embodiment, the calcium source is any compound containing calcium, including salt complexes, solubilized species, and other forms of calcium. Non-limiting examples of calcium sources include amino acid chelated calcium, calcium carbonate, calcium oxide, calcium hydroxide, calcium sulfate, calcium chloride, calcium phosphate, calcium hydrogen phosphate, calcium dihydrogen phosphate, calcium citrate, calcium malate, calcium citrate malate, calcium gluconate, calcium tartrate, calcium lactate, solubilized species thereof, and combinations thereof.

According to a particular embodiment, the osteoporosis management agent is a magnesium source. The magnesium source is any compound containing magnesium, including salt complexes, solubilized species, and other forms of magnesium. Non-limiting examples of magnesium sources include magnesium chloride, magnesium citrate, magnesium gluceptate, magnesium gluconate, magnesium lactate, magnesium hydroxide, magnesium picolate, magnesium sulfate, solubilized species thereof, and mixtures thereof. In another particular embodiment, the magnesium source comprises an amino acid chelated or creatine chelated magnesium.

In other embodiments, the osteoporosis agent is chosen from vitamins D, C, K, their precursors and/or beta-carotene and combinations thereof.

Numerous plants and plant extracts also have been identified as being effective in the prevention and treatment of osteoporosis. Non-limiting examples of suitable plants and plant extracts as osteoporosis management agents include species of the genus *Taraxacum* and *Amelanchier*, as disclosed in U.S. Patent Publication No. 2005/0106215, and species of the genus *Lindera, Artemisia, Acorus, Carthamus, Carum, Cnidium, Curcuma, Cyperus, Juniperus, Prunus, Iris, Cichorium, Dodonaea, Epimedium, Erigonoum, Soya, Mentha, Ocimum, thymus, Tanacetum, Plantago, Spearmint, Bixa, Vitis, Rosemarinus, Rhus*, and *Anethum*, as disclosed in U.S. Patent Publication No. 2005/0079232.

In certain embodiments, the functional ingredient is at least one phytoestrogen. Phytoestrogens are compounds found in plants which can typically be delivered into human bodies by ingestion of the plants or the plant parts having the phytoestrogens. As used herein, "phytoestrogen" refers to any substance which, when introduced into a body causes an estrogen-like effect of any degree. For example, a phytoestrogen may bind to estrogen receptors within the body and have a small estrogen-like effect. Examples of suitable phytoestrogens for embodiments of this invention include, but are not limited to, isoflavones, stilbenes, lignans, resorcyclic acid lactones, coumestans, coumestrol, equol, and combinations thereof. Sources of suitable phytoestrogens include, but are not limited to, whole grains, cereals, fibers, fruits, vegetables, black cohosh, agave root, black currant, black haw, chasteberries, cramp bark, dong quai root, devil's club root, false unicorn root, ginseng root, groundsel herb, licorice, liferoot herb, motherwort herb, peony root, raspberry leaves, rose family plants, sage leaves, sarsaparilla root, saw palmetto berried, wild yam root, yarrow blossoms, legumes, soybeans, soy products (e.g., miso, soy flour, soymilk, soy nuts, soy protein isolate, tempen, or tofu) chick peas, nuts, lentils, seeds, clover, red clover, dandelion leaves, dandelion roots, fenugreek seeds, green tea, hops, red wine, flaxseed, garlic, onions, linseed, borage, butterfly weed, caraway, chaste tree, vitex, dates, dill, fennel seed, gotu kola, milk thistle, pennyroyal, pomegranates, southernwood, soya flour, tansy, and root of the kudzu vine (pueraria root) and the like, and combinations thereof.

Isoflavones belong to the group of phytonutrients called polyphenols. In general, polyphenols (also known as "polyphenolics"), are a group of chemical substances found in plants, characterized by the presence of more than one phenol group per molecule.

Suitable phytoestrogen isoflavones in accordance with embodiments of this invention include genistein, daidzein, glycitein, biochanin A, formononetin, their respective naturally occurring glycosides and glycoside conjugates, matairesinol, secoisolariciresinol, enterolactone, enterodiol, textured vegetable protein, and combinations thereof.

Suitable sources of isoflavones for embodiments of this invention include, but are not limited to, soy beans, soy products, legumes, alfalfa sprouts, chickpeas, peanuts, and red clover.

In certain embodiments, the functional ingredient is at least one long chain primary aliphatic saturated alcohol. Long-chain primary aliphatic saturated alcohols are a diverse group of organic compounds. The term alcohol refers to the fact these compounds feature a hydroxyl group (—OH) bound to a carbon atom. Non-limiting examples of particular long-chain primary aliphatic saturated alcohols for use in particular embodiments of the invention include the 8 carbon atom 1-octanol, the 9 carbon 1-nonanol, the 10 carbon atom 1-decanol, the 12 carbon atom 1-dodecanol, the 14 carbon atom 1-tetradecanol, the 16 carbon atom 1-hexadecanol, the 18 carbon atom 1-octadecanol, the 20 carbon atom 1-eicosanol, the 22 carbon 1-docosanol, the 24 carbon 1-tetracosanol, the 26 carbon 1-hexacosanol, the 27 carbon 1-heptacosanol, the 28 carbon 1-octanosol, the 29 carbon 1-nonacosanol, the 30 carbon 1-triacontanol, the 32 carbon 1-dotriacontanol, and the 34 carbon 1-tetracontanol.

In a particularly desirable embodiment of the invention, the long-chain primary aliphatic saturated alcohols are policosanol. Policosanol is the term for a mixture of long-chain primary aliphatic saturated alcohols composed primarily of 28 carbon 1-octanosol and 30 carbon 1-triacontanol, as well as other alcohols in lower concentrations such as 22 carbon 1-docosanol, 24 carbon 1-tetracosanol, 26 carbon 1-hexacosanol, 27 carbon 1-heptacosanol, 29 carbon 1-nonacosanol, 32 carbon 1-dotriacontanol, and 34 carbon 1-tetracontanol.

In certain embodiments, the functional ingredient is at least one phytosterol, phytostanol or combination thereof. As used herein, the phrases "stanol", "plant stanol" and "phytostanol" are synonymous. Plant sterols and stanols are present naturally in small quantities in many fruits, vegetables, nuts, seeds, cereals, legumes, vegetable oils, bark of the trees and other plant sources. Sterols are a subgroup of steroids with a hydroxyl group at C-3. Generally, phytosterols have a double bond within the steroid nucleus, like cholesterol; however, phytosterols also may comprise a substituted side chain (R) at C-24, such as an ethyl or methyl group, or an additional double bond. The structures of phytosterols are well known to those of skill in the art.

At least 44 naturally-occurring phytosterols have been discovered, and generally are derived from plants, such as corn, soy, wheat, and wood oils; however, they also may be produced synthetically to form compositions identical to those in nature or having properties similar to those of naturally-occurring phytosterols. According to particular embodiments of this invention, non-limiting examples of phytosterols well known to those or ordinary skill in the art include 4-desmethyl sterol s (e.g., β-sitosterol, campesterol, stigmasterol, brassica sterol, 22-dehydrobrassicasterol, and Δ5-avenasterol), 4-monomethyl sterols, and 4,4-dimethyl sterols (triterpene alcohols) (e.g., cycloartenol, 24-methylenecycloartanol, and cyclobranol).

As used herein, the phrases "stanol", "plant stanol" and "phytostanol" are synonymous. Phytostanols are saturated sterol alcohols present in only trace amounts in nature and also may be synthetically produced, such as by hydrogenation of phytosterols. According to particular embodiments of this invention, non-limiting examples of phytostanols include β-sitostanol, campestanol, cycloartanol, and saturated forms of other triterpene alcohols.

Both phytosterols and phytostanols, as used herein, include the various isomers such as the α and β isomers (e.g., α-sitosterol and β-sitostanol, which comprise one of the most effective phytosterols and phytostanols, respectively, for lowering serum cholesterol in mammals).

The phytosterols and phytostanols of the present invention also may be in their ester form. Suitable methods for deriving the esters of phytosterols and phytostanols are well known to those of ordinary skill in the art, and are disclosed in U.S. Pat. Nos. 6,589,588, 6,635,774, 6,800,317, and U.S. Patent Publication Number 2003/0045473, the disclosures of which are incorporated herein by reference in their entirety. Non-limiting examples of suitable phytosterol and phytostanol esters include sitosterol acetate, sitosterol oleate, stigmasterol oleate, and their corresponding phytostanol esters. The phytosterols and phytostanols of the present invention also may include their derivatives.

Generally, the amount of functional ingredient in the composition varies widely depending on the particular composition and the desired functional ingredient. Those of ordinary skill in the art will readily ascertain the appropriate amount of functional ingredient for each composition.

In one embodiment, a method for preparing a composition comprises combining at least one mogroside of the present invention and at least one sweetener and/or additive and/or functional ingredient.

VI. Consumables

The present invention also provides a consumable comprising at least one mogroside of the present invention, or a composition comprising at least one mogroside of the present invention. In a particular embodiment, the at least one mogroside is isolated and purified.

The mogroside(s) of the present invention, or a composition comprising the same, can be admixed with any known edible or oral composition, referred to herein as a "consumable".

Consumables, as used herein, mean substances which are contacted with the mouth of man or animal, including substances which are taken into and subsequently ejected from the mouth and substances which are drunk, eaten, swallowed or otherwise ingested, and are safe for human or animal consumption when used in a generally acceptable range.

Exemplary consumables include pharmaceutical compositions, edible gel mixes and compositions, dental compositions, foodstuffs (confections, condiments, chewing gum, cereal compositions baked goods dairy products, and tabletop sweetener compositions) beverages and beverage products.

For example, a beverage is a consumable. The beverage may be sweetened or unsweetened. The mogroside(s) of the present invention, or a composition comprising the same, may be added to a beverage or beverage matrix to sweeten the beverage or enhance its existing sweetness or flavor.

In a particular embodiment, a consumable comprises at least one mogroside of the present invention in a concentration greater than about 1 ppm, such as, for example, from about 1 ppm to about 1,000 ppm, from about 25 ppm to about 1,000 ppm, from about 50 ppm to about 1,000 ppm, from about 75 ppm to about 1,000 ppm, from about 100 ppm to about 1,000 ppm, from about 200 ppm to about 1,000 ppm, from about 300 ppm to about 1,000 ppm, from about 400 ppm to about 1,000 ppm, from about 500 ppm to about 1,000 ppm or from about 50 ppm to about 600 ppm.

The consumable can optionally include additives, additional sweeteners, functional ingredients and combinations thereof, as described herein. Any of the additive, additional sweetener and functional ingredients described above can be present in the consumable.

In one embodiment, the composition a consumable. In one embodiment, the consumable is a beverage or beverage product. A beverage or beverage product comprises at least one mogroside of the present invention or a composition comprising at least one mogroside of the present invention.

"Beverage product", as used herein, is a ready-to-drink beverage, a beverage concentrate, a beverage syrup, or a powdered beverage. Suitable ready-to-drink beverages include carbonated and non-carbonated beverages. Carbonated beverages include, but are not limited to, frozen carbonated beverages, enhanced sparkling beverages, cola, fruit-flavored sparkling beverages (e.g. lemon-lime, orange, grape, strawberry and pineapple), ginger-ale, soft drinks and root beer. Non-carbonated beverages include, but are not limited to, fruit juice, fruit-flavored juice, juice drinks, nectars, vegetable juice, vegetable-flavored juice, sports drinks, energy drinks, enhanced water drinks, enhanced water with vitamins, near water drinks (e.g., water with natural or synthetic flavorants), coconut water, tea type drinks (e.g. black tea, green tea, red tea, oolong tea), coffee, cocoa drink, beverage containing milk components (milk beverages, coffee containing milk components, café au lait, milk tea, fruit milk beverages), beverages containing cereal extracts, drinkable yogurt, protein drinks and smoothies.

Beverage concentrates and beverage syrups are prepared with an initial volume of liquid matrix (e.g. water) and the desired beverage ingredients. Full strength beverages are then prepared by adding further volumes of water. Powdered beverages are prepared by dry-mixing all of the beverage ingredients in the absence of a liquid matrix. Full strength beverages are then prepared by adding the full volume of water.

Beverages comprise a matrix, i.e. the basic ingredient in which the ingredients—including the compositions of the present invention—are dissolved. In one embodiment, a beverage comprises water of beverage quality as the matrix, such as, for example deionized water, distilled water, reverse osmosis water, carbon-treated water, purified water, demineralized water and combinations thereof, can be used. Additional suitable matrices include, but are not limited to phosphoric acid, phosphate buffer, citric acid, citrate buffer and carbon-treated water.

The beverage or beverage product can further include at least one additional sweetener and/or functional ingredient and/or additive described herein.

It is contemplated that the pH of the composition, such as, for example, a beverage, does not materially or adversely affect the taste of the sweetener. A non-limiting example of the pH range of the beverage may be from about 1.8 to about 10. A further example includes a pH range from about 2 to about 5. In a particular embodiment, the pH of beverage can be from about 2.5 to about 4.2. On of skill in the art will understand that the pH of the beverage can vary based on the type of beverage. Dairy beverages, for example, can have pHs greater than 4.2.

The titratable acidity of a beverage may, for example, range from about 0.01 to about 1.0% by weight of beverage.

In one embodiment, the sparkling beverage product has an acidity from about 0.01 to about 1.0% by weight of the beverage, such as, for example, from about 0.05% to about 0.25% by weight of beverage.

The carbonation of a sparkling beverage product has 0 to about 2% (w/w) of carbon dioxide or its equivalent, for example, from about 0.1 to about 1.0% (w/w).

The beverage can be caffeinated or non-caffeinated.

The temperature of a beverage may, for example, range from about 4° C. to about 100° C., such as, for example, from about 4° C. to about 25° C.

The beverage can be a full-calorie beverage that has up to about 120 calories per 8 oz. serving.

The beverage can be a mid-calorie beverage that has up to about 60 calories per 8 oz. serving.

The beverage can be a low-calorie beverage that has up to about 40 calories per 8 oz. serving.

The beverage can be a zero-calorie that has less than about 5 calories per 8 oz. serving.

In a particular embodiment, the composition is a cola beverage. The cola beverage can be a low-, mid- or zero-calorie beverage.

In a particular embodiment, the beverage is a diet beverage. In a more particular embodiment, the beverage is a diet carbonated beverage.

In a particular embodiment, the beverage of the present invention is a flavored water beverage.

The concentration of the mogroside of the present invention in the beverage may be above, at or below the threshold sweetness or flavor recognition concentration of the mogroside of the present invention.

In one embodiment, a mogroside of the present invention is present in the beverage in a concentration greater than about 1 ppm, such as, for example, from about 1 ppm to about 1,000 ppm, from about 25 ppm to about 1,000 ppm, from about 50 ppm to about 1,000 ppm, from about 75 ppm to about 1,000 ppm, from about 100 ppm to about 1,000 ppm, from about 200 ppm to about 1,000 ppm, from about 300 ppm to about 1,000 ppm, from about 400 ppm to about 1,000 ppm or from about 500 ppm to about 1,000 ppm.

In a more particular embodiment, a mogroside of the present invention is present in the beverage in a concentration from about 25 ppm to about 600 ppm, such as, for example, from about 25 ppm to about 500 ppm, from about 25 ppm to about 400 ppm, from about 25 ppm to about 300 ppm, from about 25 ppm to about 200 ppm, from about 25 ppm to about 100 ppm, from about 50 ppm to about 600 ppm, from about 50 ppm to about 500 ppm, from about 50 ppm to about 400 ppm, from about 50 ppm to about 300 ppm, from about 50 ppm to about 200 ppm, from about 50 ppm to about 100 ppm, from about 100 ppm to about 600 ppm, from about 100 ppm to about 500 ppm, from about 100 ppm to about 400 ppm, from about 100 ppm to about 300 ppm, from about 100 ppm to about 200 ppm, from about 200 ppm to about 600 ppm, from about 200 ppm to about 500 ppm, from about 200 ppm to about 400 ppm, from about 200 ppm to about 300 ppm, from about 300 ppm to about 600 ppm, from about 300 ppm to about 500 ppm, from about 300 ppm to about 400 ppm, from about 400 ppm to about 600 ppm, from about 400 ppm to about 500 ppm or from about 500 ppm to about 600 ppm.

In one embodiment, the beverage has a sweetness of 3 degrees Brix or greater, e.g. 4 degrees Brix or greater, 5 degrees Brix or greater, 6 degrees Brix or greater, 7 degrees Brix or greater, 8 degrees Brix or greater, 9 degrees Brix or greater or 10 degrees Brix or greater.

In another embodiment, the mogroside of the present invention is present in the beverage in an amount effective to provide 3 degrees Brix or greater, e.g. 4 degrees Brix or greater, 5 degrees Brix or greater, 6 degrees Brix or greater, 7 degrees Brix or greater, 8 degrees Brix or greater, 9 degrees Brix or greater or 10 degrees Brix or greater.

In still another embodiment, a sweetener composition of the present invention is present in the beverage in an amount effective to provide 3 degrees Brix or greater, e.g. 4 degrees Brix or greater, 5 degrees Brix or greater, 6 degrees Brix or greater, 7 degrees Brix or greater, 8 degrees Brix or greater, 9 degrees Brix or greater or 10 degrees Brix or greater.

VII. Methods of Use

The compounds and compositions of the present invention can be used to impart sweetness or to enhance the flavor or sweetness of consumables. In particular embodiments, the mogroside(s) of the present invention can be used to sweeten a consumable and/or to enhance the flavor of a consumable. Consumables containing at least one mogroside of the present invention have taste attributes that are more like a sucrose-sweetened consumable compared to a consumable without the at least one mogroside of the present invention.

In one aspect, the present invention is a method of preparing a sweetened consumable comprising (i) providing a consumable and (ii) adding at least one mogroside of the present invention to the consumable to provide a sweetened consumable.

In a particular embodiment, a method of preparing a sweetened consumable comprises (i) providing an unsweetened consumable and (ii) adding at least one mogroside of the present invention to the unsweetened consumable to provide a sweetened consumable.

In a particular embodiment, the present invention is a method of preparing a sweetened beverage comprising (i) providing a beverage and (ii) adding at least one mogroside of the present invention to the beverage to provide a sweetened beverage.

In a particular embodiment, the present invention is a method of preparing a sweetened beverage comprising (i) providing an unsweetened beverage and (ii) adding at least one mogroside of the present invention to the unsweetened beverage to provide a sweetened beverage.

In the above methods, the mogroside(s) of the present invention may be provided as such, i.e., in the form of a compound, or in form of a composition. When provided as a composition, the amount of mogroside in the composition is effective to provide a concentration of the mogroside that is above, at or below its flavor or sweetness recognition threshold when the composition is added to the consumable (e.g., the beverage). When the mogroside(s) of the present invention is not provided as a composition, it may be added to the consumable at a concentration that is above, at or below its flavor or sweetness recognition threshold.

In one embodiment, the present invention is a method for enhancing the sweetness of a consumable comprising (i) providing a consumable comprising at least one sweetener in a sweetening amount and (ii) adding at least one mogroside of the present invention, or a composition comprising the same, to the consumable to provide a consumable with enhanced sweetness, wherein the mogroside of the present invention is added to the consumable at a concentration at or below its sweetness recognition threshold. In a particular embodiment, a mogroside of the present invention is added to the consumable at a concentration below its sweetness recognition threshold.

In a particular embodiment, the present invention is a method for enhancing the sweetness of a beverage comprising (i) providing a beverage comprising at least one sweetener in a sweetening amount and (ii) adding at least one mogroside of the present invention, or a composition comprising the same, to the beverage to provide a beverage with enhanced sweetness, wherein the mogroside is added to the beverage at a concentration at or below its sweetness recognition threshold. In a particular embodiment, the mogroside of the present invention is added to the consumable at a concentration below its sweetness recognition concentration threshold.

In another embodiment, the present invention is a method for enhancing the flavor of a consumable comprising (i) providing a consumable comprising at least one flavor ingredient and (ii) adding at least one mogroside of the present invention, or a composition comprising the same, to the consumable to provide a consumable with enhanced flavor, wherein the mogroside of the present invention is added to the consumable at a concentration at or below its flavor recognition threshold. In a particular embodiment, the mogroside of the present invention is added to the consumable at a concentration below its flavor recognition threshold.

In a particular embodiment, a method for enhancing the flavor of a beverage is provided that comprises (i) providing a beverage comprising at least one flavor ingredient and (ii) adding at least one mogroside of the present invention, or a composition comprising the same, to the beverage to provide a beverage with enhanced flavor, wherein the mogroside is added to the beverage at a concentration at or below the flavor recognition threshold of the mogroside. In a particular embodiment, the mogroside of the present invention is added to the consumable at a concentration below its flavor recognition threshold.

In one embodiment, a method of enhancing the sweetness of a consumable comprises (i) providing a consumable comprising at least one sweetener and (ii) adding at least one mogroside of the present invention to the composition to provide a composition with enhanced sweetness.

In another embodiment, a method of enhancing the sweetness of a consumable comprises (i) providing a consumable matrix and (ii) adding at least one sweetener and at least one mogroside of the present invention to the consumable matrix to provide a consumable with enhanced sweetness. The at least one sweetener and at least one mogroside of the present invention can be added together, i.e. in the form of a composition, or separately.

As used herein, the term "consumable matrix" refers to a composition containing all typical ingredients except the sweetener or sweetener composition.

In a particular embodiment, the SE of the consumable comprising the at least one mogroside of the present invention and at least one sweetener is enhanced by at least about 1.2-fold compared to the SE of the consumable in the absence of the at least one mogroside of the present invention, such as, for example, at least about 1.3-fold, at least about 1.4-fold, at least about 1.5-fold, at least about 1.6-fold, at least about 1.7-fold, at least about 1.8-fold, at least about 1.9-fold and at least about 2.0-fold.

In another embodiment, addition of the at least one mogroside of the present invention to the consumable or consumable matrix increases the degrees Brix by at least 1 degree Brix compared to the Brix of the consumable without the mogroside of the present invention, such as, for example, at least 2 degrees Brix, at least 3 degrees Brix or at least 4 degrees Brix.

In another aspect, a method of making a consumable taste more like a sucrose-sweetened consumable comprises (i) providing a consumable comprising at least one sweetener in a sweetening amount and (ii) adding at least one mogroside of the present invention in an amount effective to modulate one or more taste attributes of the sweetener to make the consumable taste more like a sucrose-sweetened consumable compared to the consumable in the absence of the at least one mogroside of the present invention.

In another embodiment, a method of making a consumable taste more like a sucrose-sweetened consumable comprises (i) providing a consumable matrix and (ii) adding at least one sweetener in a sweetening amount and at least one mogroside of the present invention to the consumable matrix to provide a consumable that tastes more like a sucrose-sweetened consumable, wherein the at least one mogroside of the present invention is present in an amount effective to modulate one or more taste attributes of the sweetener to make the consumable taste more like a sucrose-sweetened consumable compared to the consumable in the absence of the at least one mogroside of the present invention. The at least one sweetener and at least one mogroside of the present invention can be added together, i.e. in the form of a composition, or separately.

Methods or preparing compositions with enhanced sweetness are also provided.

In one aspect, a method of preparing a composition comprises (i) providing a composition comprising at least one sweetener and (ii) adding at least one mogroside of the present invention to the composition to provide a composition.

In one aspect, the present invention is a method of preparing a sweetened consumable comprising (i) providing a consumable and (ii) adding at least one mogroside of the present invention to the consumable in a sweetening amount to provide a sweetened consumable.

In a particular embodiment, a method of preparing a sweetened consumable comprises (i) providing an unsweetened consumable and (ii) adding at least one mogroside of the present invention to the unsweetened consumable in a sweetened amount to provide a sweetened consumable.

In a particular embodiment, the present invention is a method of preparing a sweetened beverage comprising (i) providing a beverage and (ii) adding at least one mogroside of the present invention to the beverage in a sweetening amount to provide a sweetened beverage.

In a particular embodiment, the present invention is a method of preparing a sweetened beverage comprising (i) providing an unsweetened beverage and (ii) adding at least one mogroside of the present invention to the unsweetened beverage in a sweetening amount to provide a sweetened beverage.

VIII. Methods of Purification

The present invention also extends to methods of purifying a mogroside of the present invention.

In one embodiment, the present invention is a method for purifying a mogroside of the present invention comprising (i) passing a solution comprising a source material comprising a mogroside of the present invention through a HPLC column and (ii) eluting fractions comprising a mogroside of the present invention to provide a purified mogroside composition comprising a mogroside of the present invention. The HPLC column can be any suitable HPLC preparative or semi-preparative scale column.

As used herein, the term "preparative HPLC" refers to an HPLC system capable of producing high (500 or more) microgram, milligram, or gram sized product fractions. The term "preparative" includes both preparative and semi-preparative columns, but is not intended to include analytical columns, which provide fractions in the nanogram to low microgram range.

As used herein, an "HPLC compatible detector" is a detector suitable for use in an HPLC system which is capable of providing a detectable signal upon elution of a compound peak. For example, a detector capable of generating a signal when a compound elutes from the compound is an HPLC compatible detector. Where component absorbance varies widely, it may be necessary to utilize more than one detector. A detector capable of detecting a desired component is not an "incompatible" detector due to its inability to detect a non-desired peak.

An HPLC device typically includes at least the following components: a column, packed with a suitable stationary phase, a mobile phase, a pump for forcing the mobile phase through the column under pressure, and a detector for detecting the presence of compounds eluting off of the column. The devices can optionally include a means for providing for gradient elution, although such is not necessary using the methods described herein. Routine methods and apparatus for carrying out HPLC separations are well known in the art.

Suitable stationary phases are those in which the compound of interest elutes. Preferred columns can be, and are not limited to, normal phase columns (neutral, acidic or basic), reverse phase columns (of any length alkyl chain), a synthetic crosslinked polymer columns (e.g., styrene and divinylbenzene), size exclusion columns, ion exchange columns, bioaffinity columns, and any combination thereof. The particle size of the stationary phase is within the range from a few μm to several 100 μm.

Suitable detection devices include, but are not limited to, mass spectrometers, UV detectors, IR detectors and light scattering detectors. The methods described herein use any combination of these detectors. The most preferable embodiment uses mass spectrometers and UV detectors.

"Source material", as used herein, refers to the material being purified by the present method. The source material contains a mogroside of the present invention in a purity less than the purity provided by the present purification method. The source material can be liquid or solid. Exemplary source materials include, but are not limited to, mixtures of mogrosides and Luo Han Guo extract (commercial or prepared).

As understood by persons skilled in the art, any solid source materials must be brought into solution prior to carrying out the HPLC method.

In one embodiment, a representative analytical HPLC protocol is correlated to a preparative or semi-preparative HPLC protocol used to purify a compound.

In another embodiment, appropriate conditions for purifying a mogroside of the present invention can be worked out by route scouting a representative sample for a given analytical HPLC column, solvent system and flow rate. In yet another embodiment, a correlated preparative or semi-preparative HPLC method can be applied to purify a mogroside of the present invention with modifications to the purification parameters or without having to change the purification parameters.

In some embodiments, the eluent (mobile phase) is selected from the group consisting of water, acetonitrile, methanol, 2-propanol, ethyl acetate, dimethylformamide, dimethylsulfide, pyridine, triethylamine, formic acid, trifluoroacetic acid, acetic acid, an aqueous solution containing ammonium acetate, heptafluorobutyric acid, and any combination thereof.

In one embodiment, the HPLC method is isocratic. In another embodiment, the HPLC method is a gradient. In still another embodiment, the HPLC method is step-wise.

In one embodiment, impurities are eluted off of the HPLC column after eluting one or more fractions containing a mogroside of the present invention. In another embodiment, impurities are eluted off of the HPLC column before eluting one or more fractions containing a mogroside of the present invention.

The method can further include removal of solvent from the eluted solution, i.e. drying. In one embodiment, the method further comprises partial removal of solvents from the eluted solution to provide a concentrate comprising a mogroside of the present invention. In another embodiment, the method further comprises removing substantially all the solvent from the eluted solutions to provide substantially dry composition comprising a mogroside of the present invention.

Removal of solvent can be performed by any known means to one of skill in the art including, but not limited to, evaporation, distillation, lyophilization, vacuum drying and spray drying.

The resulting purified fractions comprising a mogroside of the present invention can be further purified by other methods to increase purity. Suitable methods include, but are not limited to, crystallization, chromatography, extraction and distillation. Such methods are well-known to persons skilled in the art.

The source material can be one fraction, or multiple fractions, containing a mogroside of the present invention collected from at least one previous method or HPLC protocol. In one embodiment, multiple fractions from the same, previous methods or HPLC protocols are pooled and optionally, solvents are removed, prior to re-subjecting the source material to another method. In other embodiments, fractions from different, previous methods or HPLC protocol are pooled, and optionally, solvents are removed, prior to re-subjecting the source material to another method.

In one embodiment, the source material re-subjected to additional method(s) comprises liquid fractions obtained from one or more previous (and optionally, different) methods mixed with substantially dry material obtained via drying of fractions obtained from one or more previous (and optionally, different) methods. In another embodiment, the source material re-subjected to additional method(s) comprises substantially dry material obtained via drying of fractions obtained from one or more previous (and optionally, different) methods, where said source material is brought into solution prior to passing the solution through the next HPLC column.

The second and subsequent methods may have different HPLC protocols (e.g. solvent systems, columns, methods) and different steps following elution (e.g. partial removal of solvent, complete removal of solvent, elution of impurities, use of crystallization or extraction).

The material isolated can be subjected to further methods 2, 3, 4 or more times, each time providing a higher level of purity of purified mogroside of the present invention.

In one embodiment, the method provides a purified mogroside composition comprising a mogroside of the present invention in a purity of at least about 80% by weight or greater, such as, for example, at least about 85% by weight, at least about 90% by weight, at least about 95% by weight or at least about 97% or greater. In another embodiment, purification provides a pure mogroside of the present invention, i.e., >99% by weight on a dry basis.

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

EXAMPLES

Example 1: Mogroside V Bioconversion

Figure 1B:
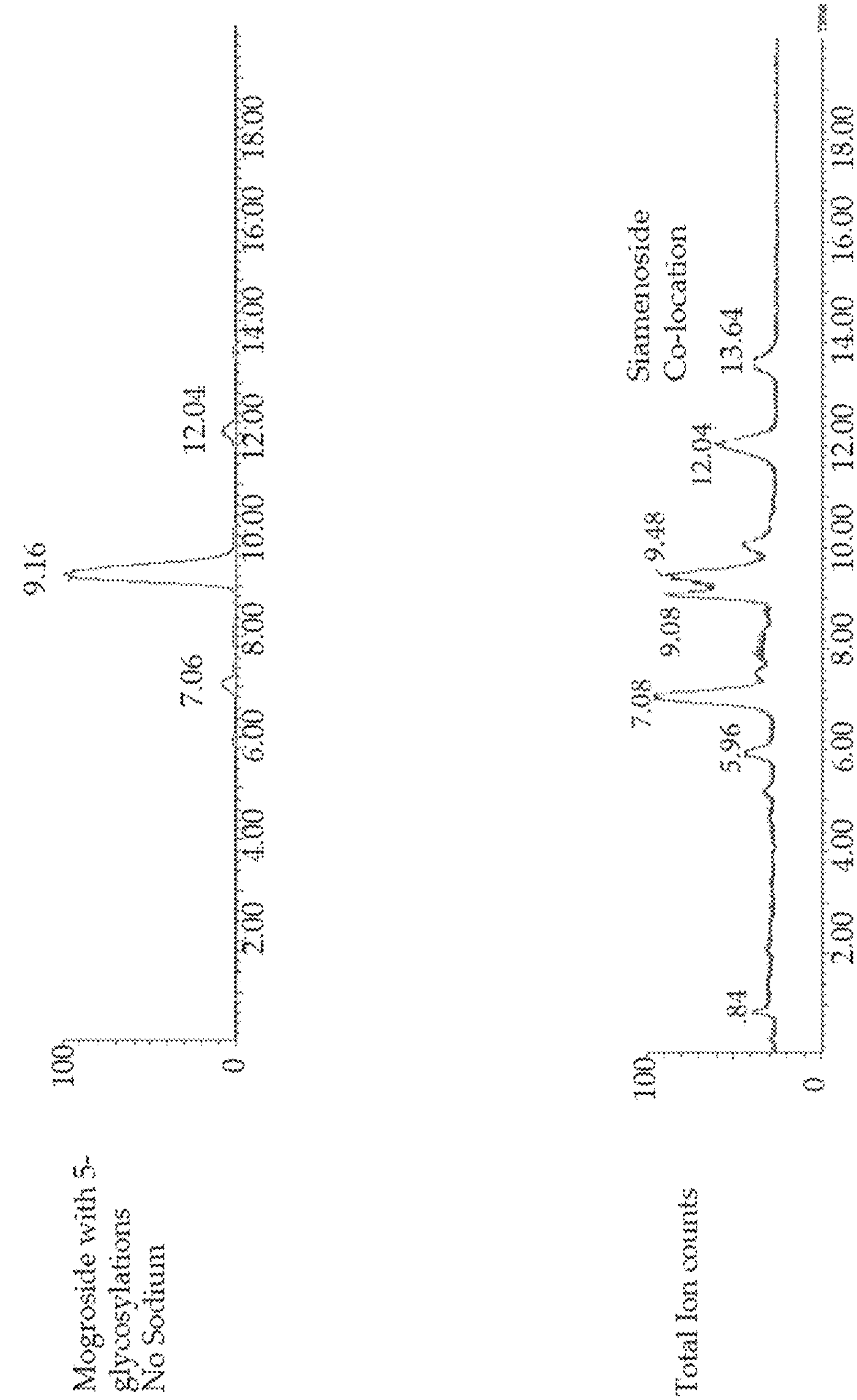

LC-MS was performed on the MV 90 (90% Mogroside V) substrate (Hunan Huacheng Biotech Inc.) Two significant peaks are observed in the LC-MS extracted for the mass of a xylose containing mogroside with 5-glycosylations +/−sodium ("xylose containing mogroside 1" and "xylose containing mogroside 2"). The results are shown in FIG. 1.

Using a DSM Maxilact enzyme in the bioconversion reaction, the following reactions are expected to occur.

Scheme 1
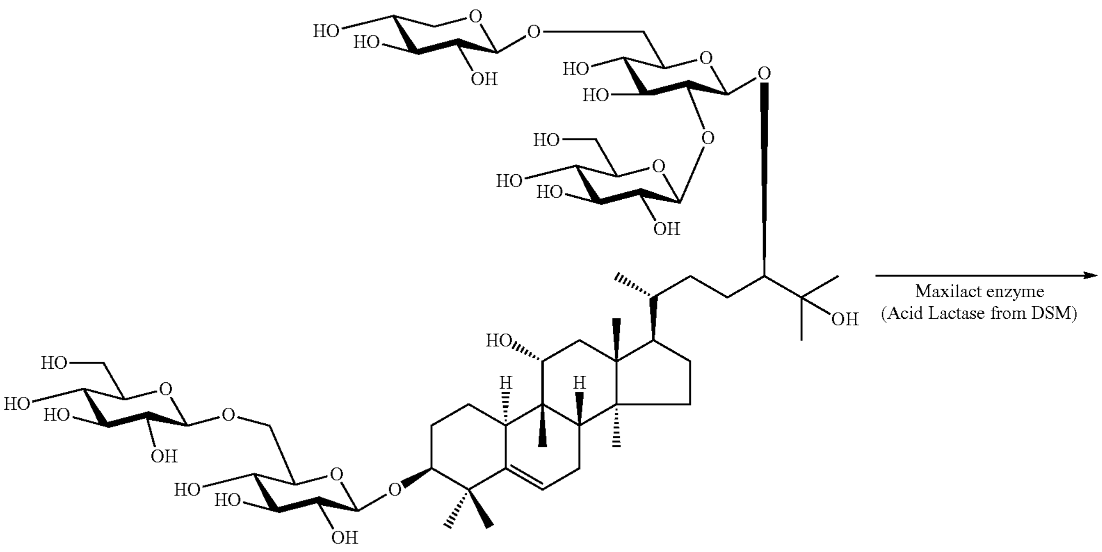
Mogroside V-like
Xylose-containing
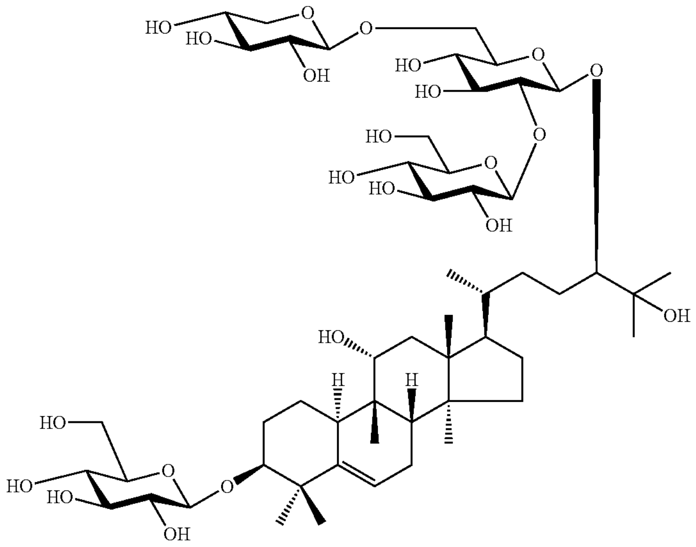
Mogroside IV-like
Xylose-containing In one embodiment, a reaction is provided where iso-mogroside V-like xylose-containing compound is converted to a mogroside IV-like xylose-containing compound.

Scheme 2

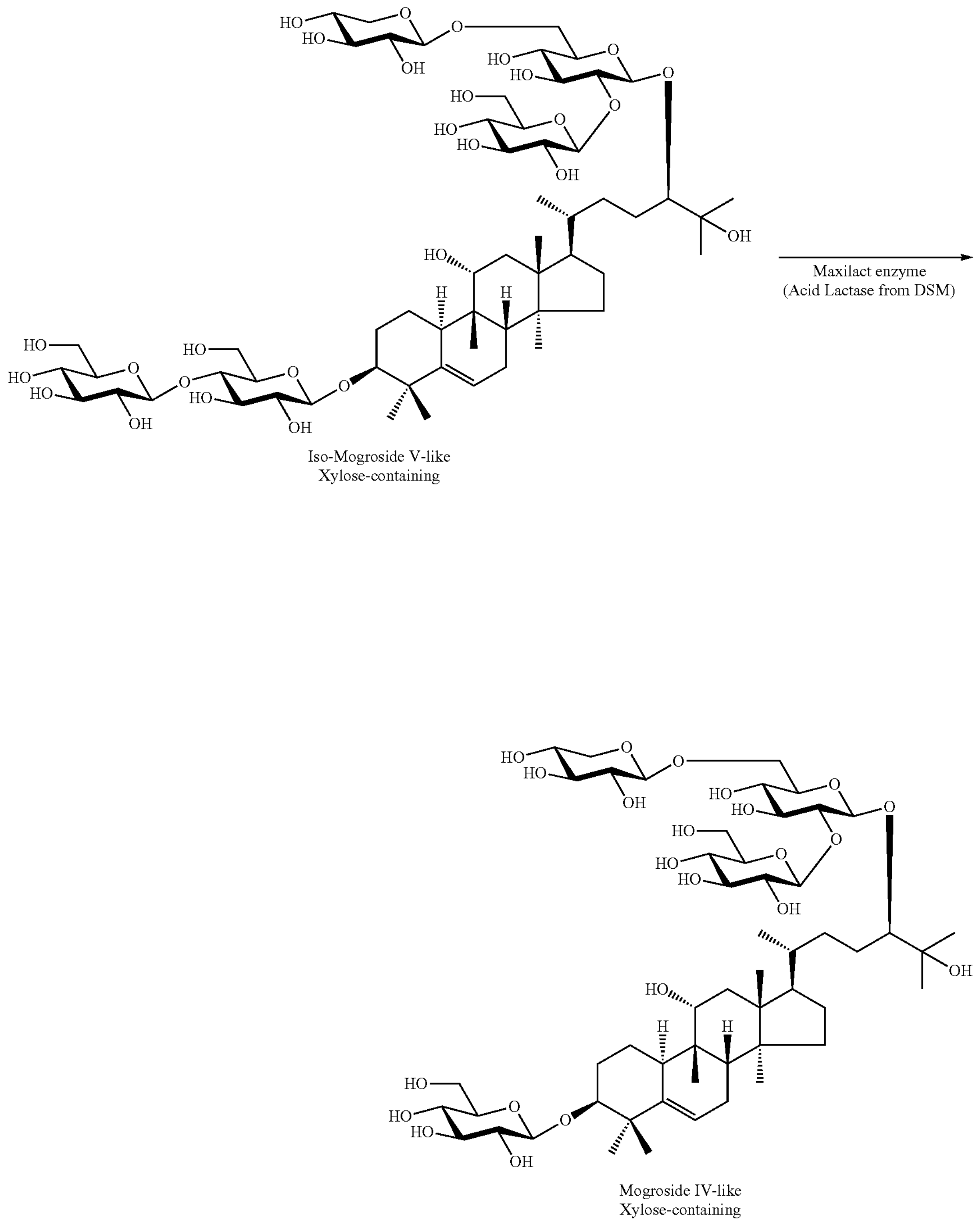

Iso-Mogroside V-like Xylose-containing

Mogroside IV-like Xylose-containing

One or both of these may be converted to the xylose-containing mogrosides with 4 glycosylations.

Based on knowledge of the structure of mogrosides containing 5-glucosylations (i.e. glucose only mogrosides), the likely xylose-containing mogrosides with 5 glycosyl units resemble Mogroside V and Iso-mogroside V.

Example 2: Mogroside Diversification

To prepare mogroside compounds using pathways of Mogroside V bioconversion, various enzymes were screened for use in adding non-glucose monosaccharide to C24 glycosyl group of MogIIIE.

Scheme 3

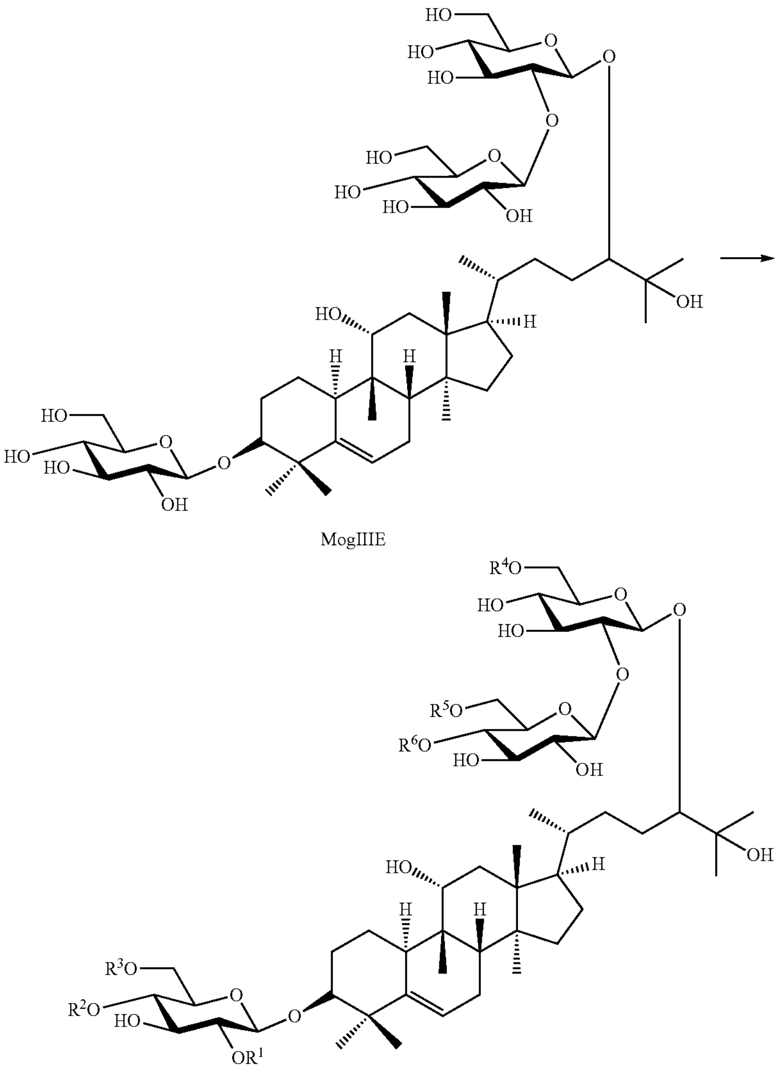

MogIIIE

Novel Mogroside derivatives

R = Rhamnosyl, Fructosyl, Xylosyl, Deoxyglucosyl, Galactosyl

Materials and Instruments:

Glycotransferase and transglycosylating glycosidase were selected that were capable of adding α/β non-glucose sugars to glucose positions (not only to C6 position, but also to C3, C4 position). Enzymes useful for the conversion reactions include but are not limited to α-Rhamnosidase 78A (Megazyme, E-RHAMS), β-Fructofuranosidase (Invertase) (Megazyme, E-INVRT), α-Galactosidase (Megazyme, E-AGALPS) and α-xylosidase (Megazyme, E-AXSEC).

Reaction Mixture:

50 μL reaction (40° C. for 40 hrs):

| | |
|---|---|
| Enzyme | 1 μL |
| 1M sugar | 4 μL |
| 100 mM MogIIIE | 10 μL |
| 2x buffer, pH varies | 25 μL |
| H2O | 10 μL |

Set up pH ladders to assess changes to bioconversion yield:

Acetate buffer 3.6;

Acetate buffer 4.6;

Acetate buffer 5.6;

Phosphate buffer 6.6;

Phosphate buffer 7.0

We applied above two tables to prepare the buffers with different pH (4.6, 5.6, 6.6).

Purification Process

The reaction mixture was purified by C18 column on HPLC system.

1. Rhamnose 25 mL reaction (40° C. for 60 hrs):

| | |
|---|---|
| α-Rhamnosidase | 0.5 mL |
| 500 mM Rhamnose in 2x buffer, pH 5.6 | 12.5 mL |
| 130 mM MogIIIE | 11 mL |

At the 30 hrs, another 0.5 mL α-Rhamnosidase was added.

After 60 hrs, the reaction was boiled and filtered, and subjected to HPLC purification.

Figure 2:
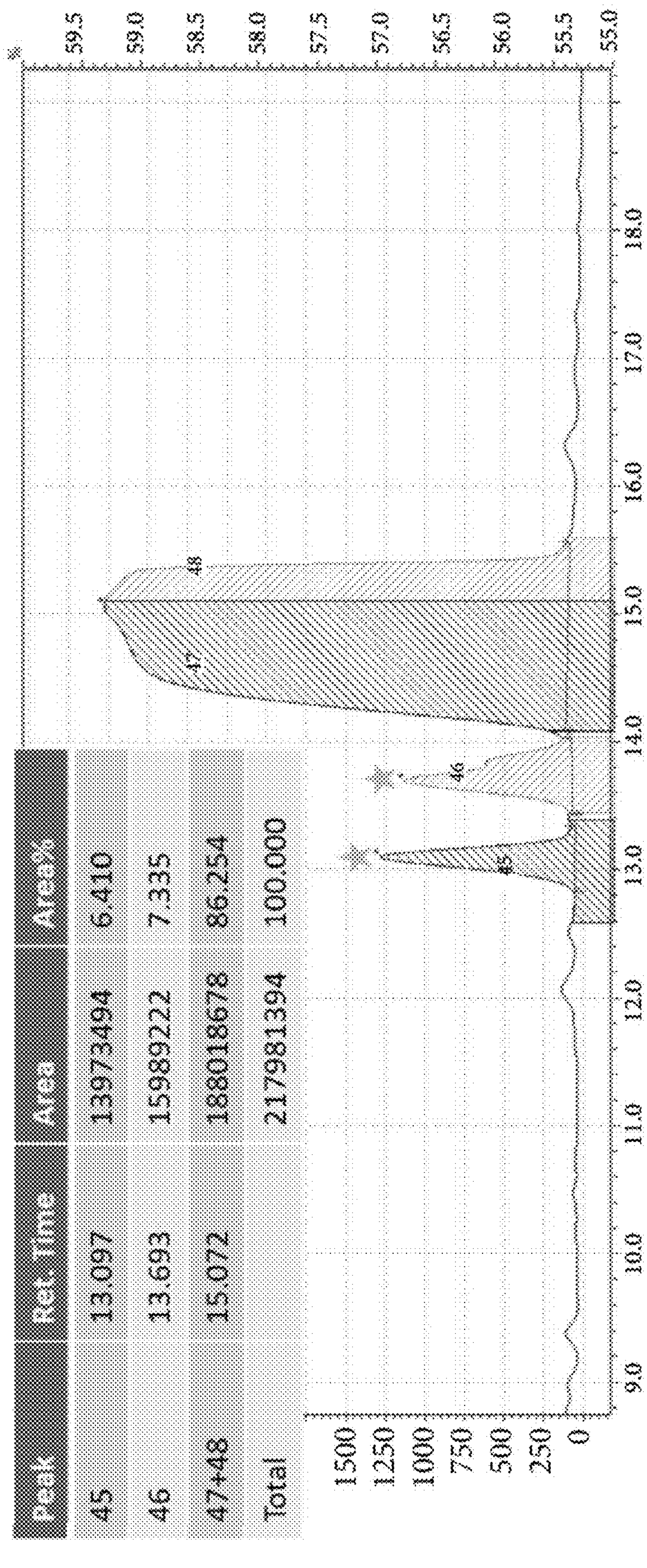
FIG. 2 shows the HPLC trace of the reaction of MogIIIE and rhamnose (Example 2).

This is shown in FIG. 2.

After C18 HPLC purification (10-40% acetonitrile), ~24 mg of peak 45 was collected, peak 46 was two compounds that could not be separated. 47+48 was the substrate MogIIIE Peak 45 was subjected to NMR analysis and determined to be CC-00500.

The reaction at pH 4.6-5.6 had comparatively high productivity.

Figure 3A:
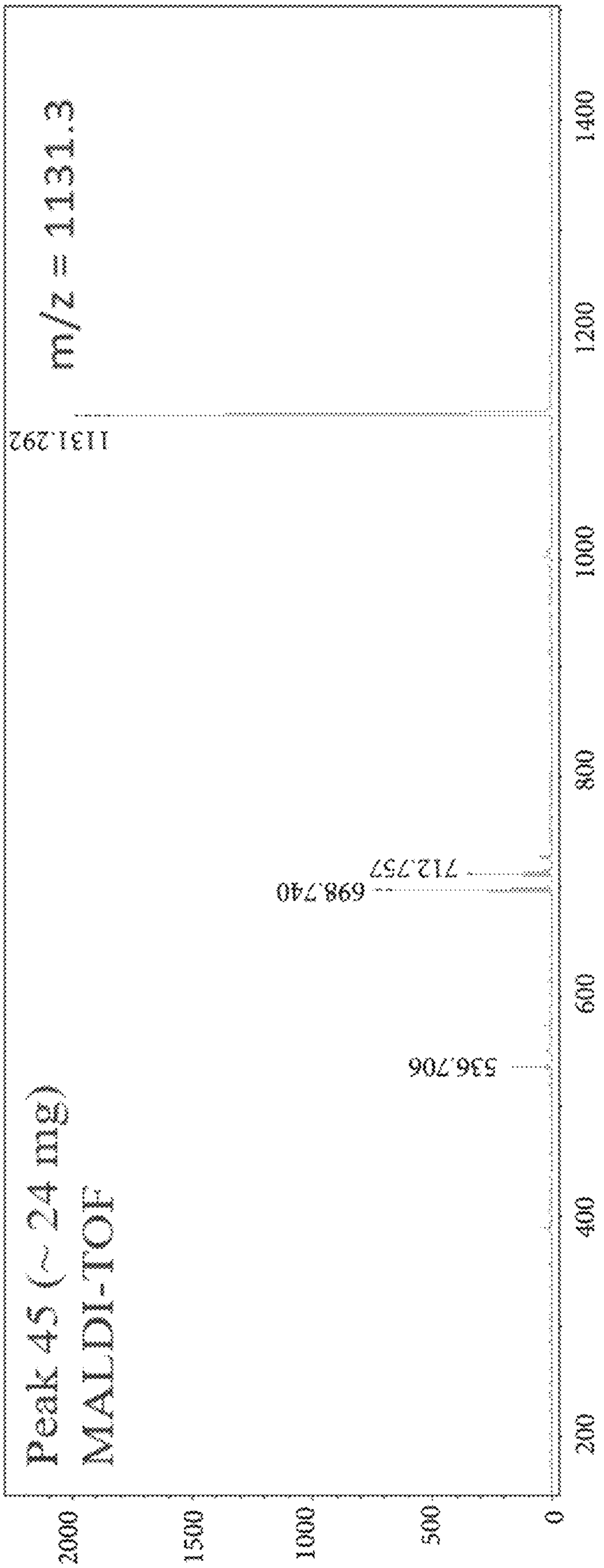
FIG. 3 shows the Maldi mass spectrum of Peaks 45 (FIG. 3A) and 46 (FIG. 3B) isolated from the reaction of MogIIIE and rhamnose (Example 2).
Figure 3B:
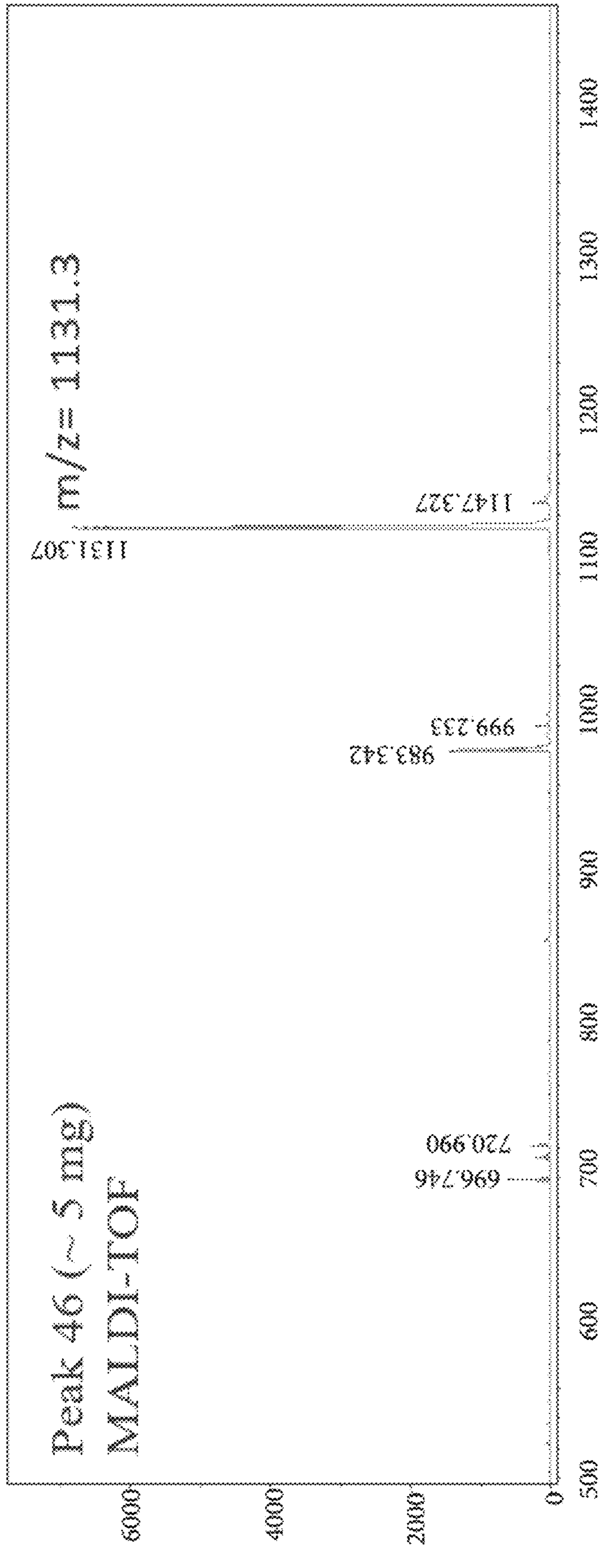

Isolated HPLC peaks were subjected to mass spectroscopy analysis is shown in FIG. 3.

Both isolated HPLC peaks showed an increase in mass from 985 to 1131, as was expected for addition of 1 rhamnose to the mogroside IIIE substrate.

2. Galactose 25 mL reaction (40° C. for 60 hrs):

| | |
|---|---|
| α-Galactosidase | 0.5 mL |
| 500 mM Rhamnose in 2× buffer, pH 4.6 | 12.5 mL |
| 130 mM MogIIIE | 11 mL |

At the 30 hrs, another 0.5 mL α-Galactosidase was added.

After 60 hrs, the reaction was boiled and filtered, then subject to HPLC purification.

Figure 4:
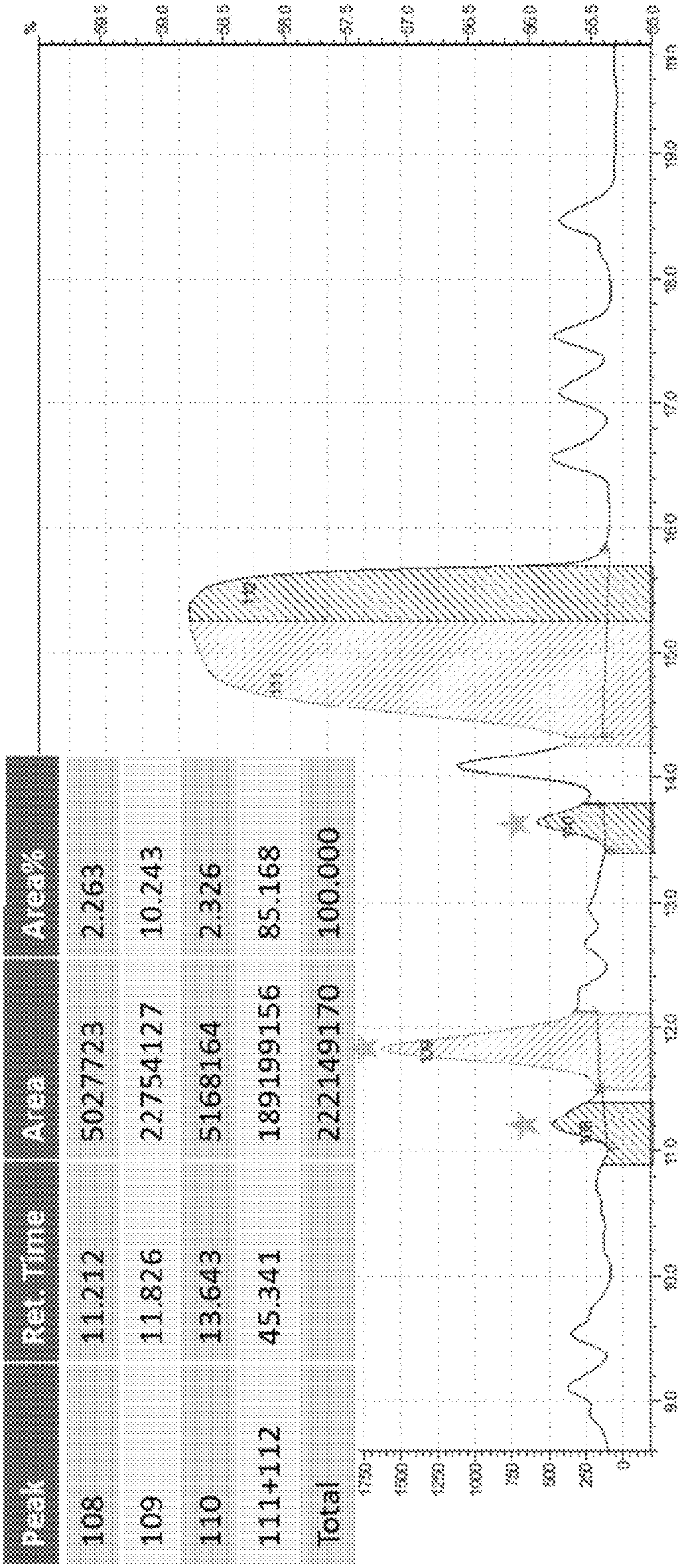
FIG. 4 shows the HPLC trace of the reaction of MogIIIE and galactose (Example 2).

This is shown in FIG. 4.

After C18 HPLC purification (10-40% acetonitrile), ~4 mg of peak 108 was collected, ~28 mg of peak 109 was collected, peak 110 contained a large amount of substrate MogIIIE. 111+112 was the substrate MogIIIE Peaks 108 and 109 were subjected to NMR analysis and Peak 108 was identified as CC-00489.

Figure 5A:
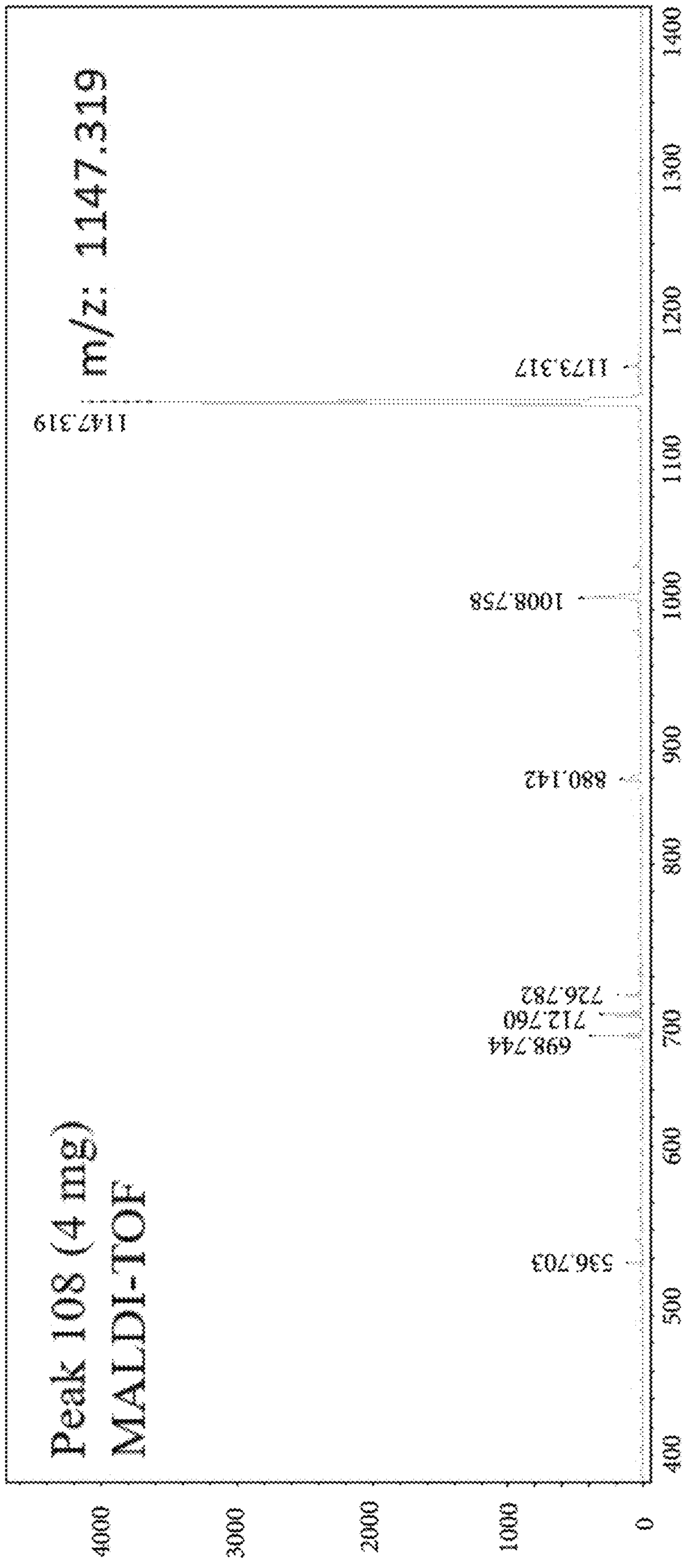
FIG. 5 shows the Maldi mass spectrum of Peaks 108 (FIG. 5A) and 109 (FIG. 5B) isolated from the reaction of MogIIIE and galactose (Example 2).
Figure 5B:
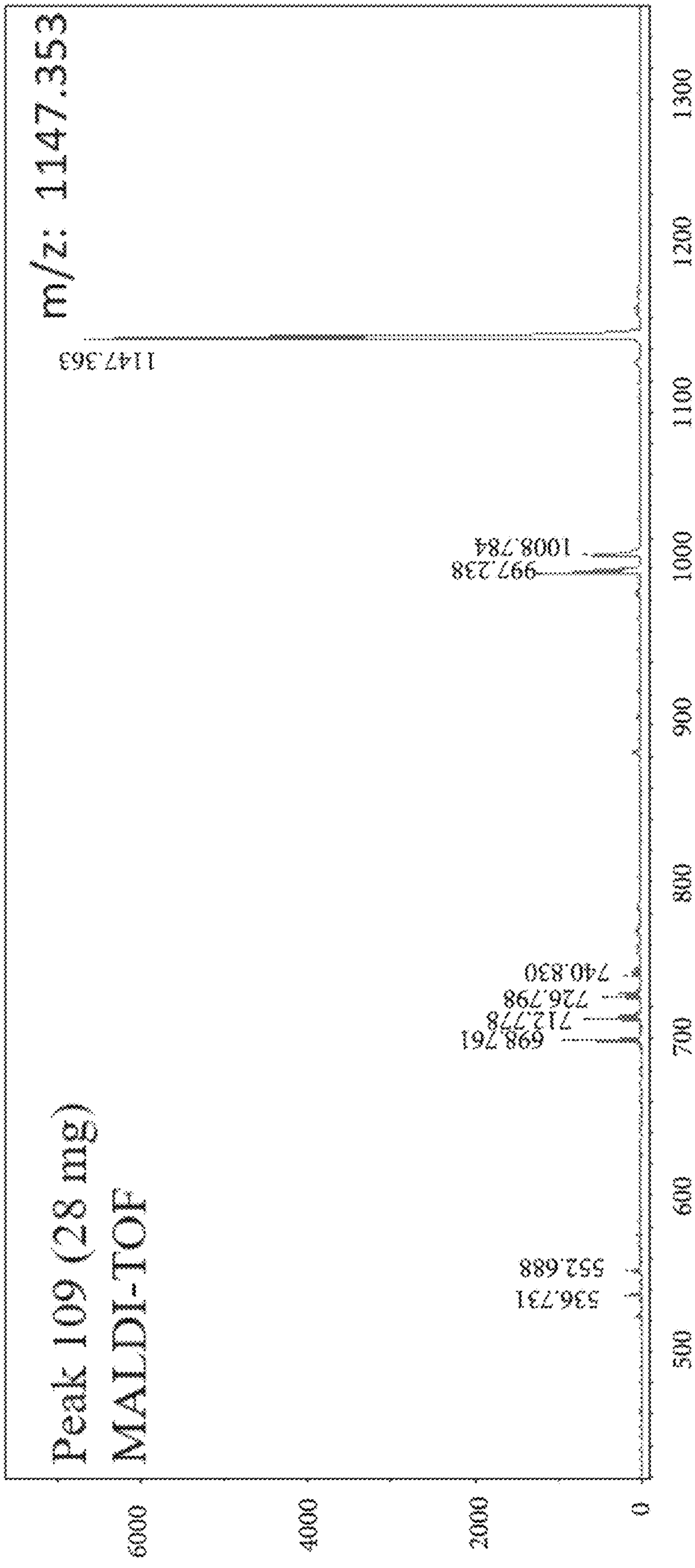

Reaction at pH 3.6-4.6 has comparatively high productivity. Isolated HPLC peaks were subjected to mass spectroscopy analysis is shown in FIG. 5. Both isolated HPLC peaks showed an increase in mass from 985 to 1147, as was expected for addition of 1 rhamnose to the mogroside IIIE substrate 3. Xylose 25 mL reaction (40° C. for 60 hrs):

| | |
|---|---|
| α-Galactosidase | 0.5 mL |
| 500 mM Xylose in 2× buffer, pH 4.6 | 12.5 mL |
| 130 mM MogIIIE | 11 mL |

At the 30 hrs, another 0.5 mL α-Galactosidase was added.

Figure 6:
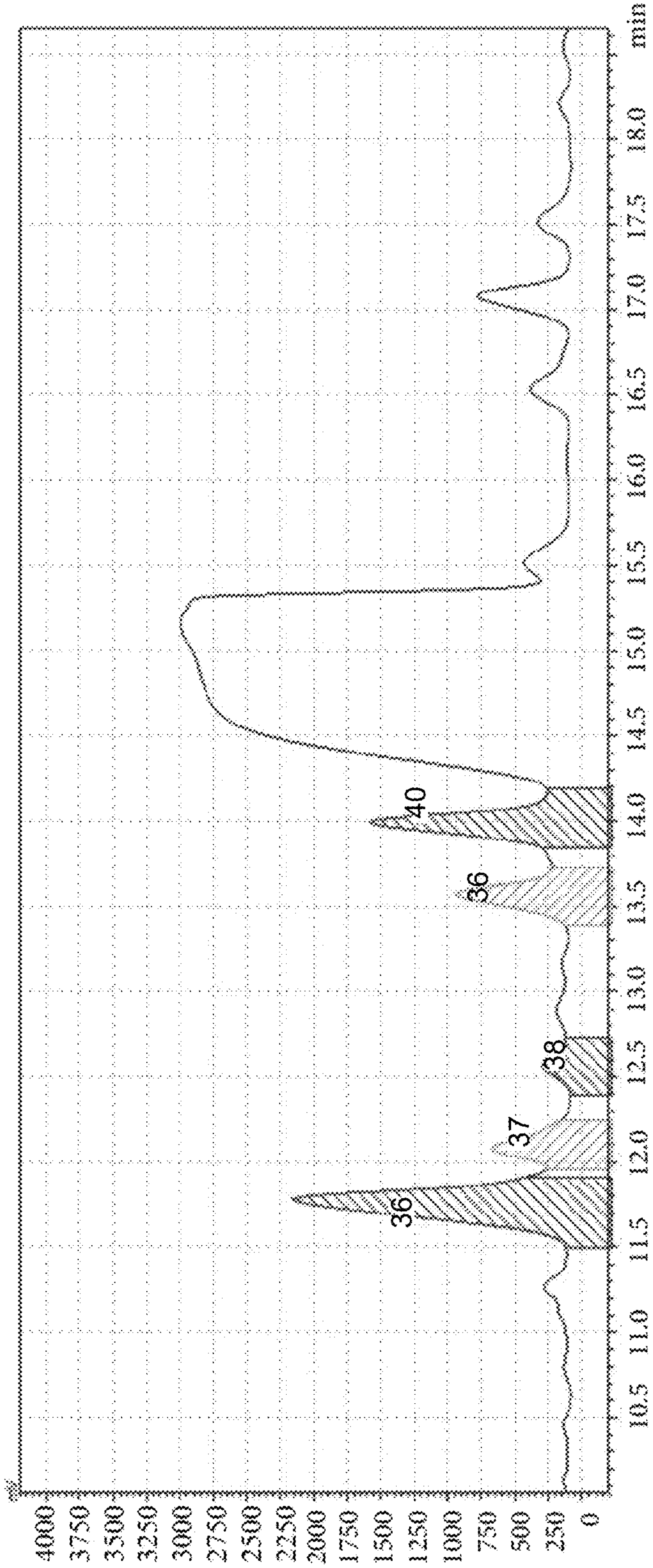
FIG. 6 shows the MS trace of the reaction of MogIIIE and xylose (Example 2).

After 60 hrs, the reaction was boiled and filtered, then subject to HPLC purification. The reaction at pH 4.6 had comparatively high productivity. This is shown in FIG. 6.

Figure 7:
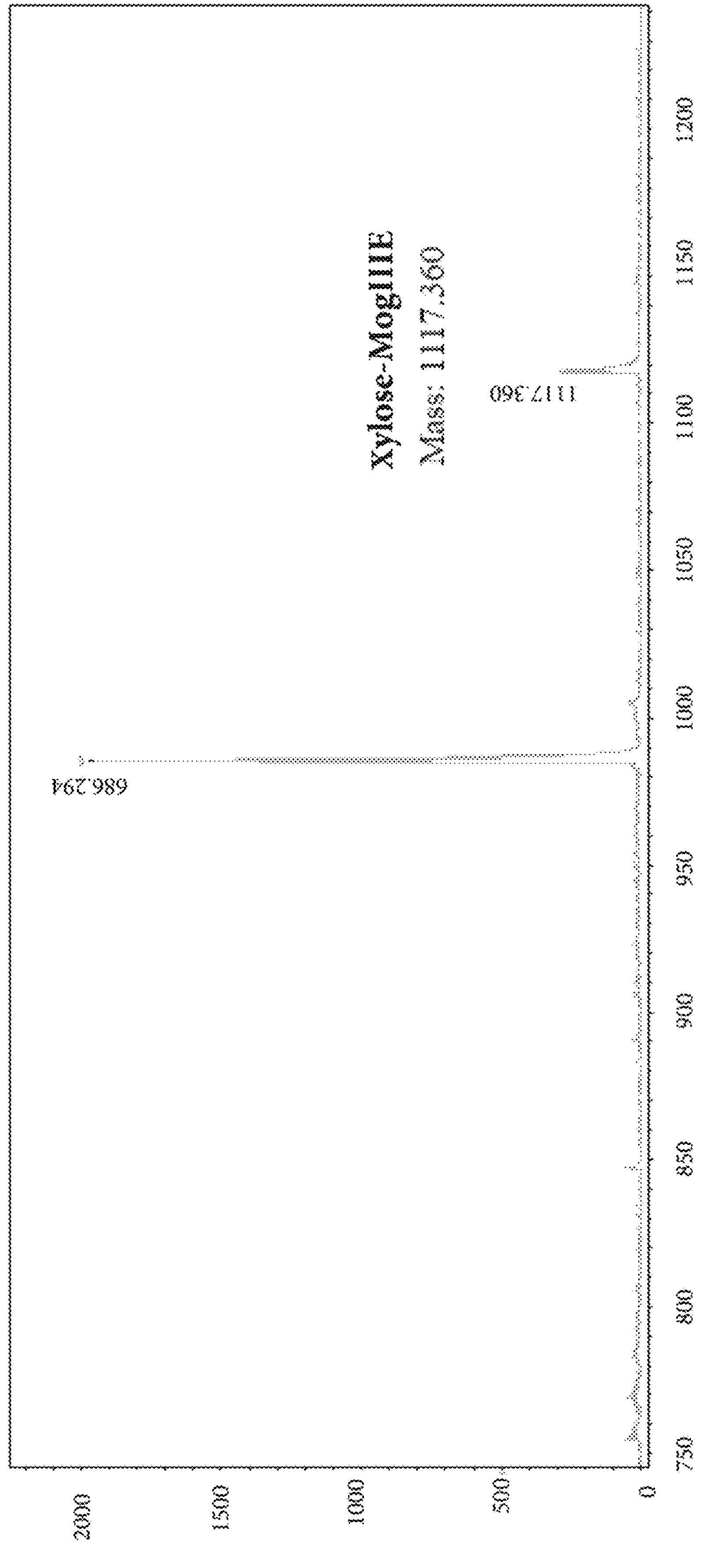
FIG. 7 shows the Maldi mass spectrum of Peak 39 isolated from the reaction of MogIIIE and xylose (Example 2).

After C18 HPLC purification (10-40% acetonitrile), peaks 36, 37, 38, 39, and 40 were collected. The mass spectroscopy analysis of peak 39 showed a minor peak with m/z of 1117 suggesting xylose had been add the mogroside IIIE, as is shown in FIG. 7.

Conclusions:

By MALDI-TOF analysis, the productivities of adding galactose, rhamnose or xylose are comparatively high.

Example 3: Sweetness Evaluation of Cc-00489

The sweetness of mogrol-3-O[β-D-glucopyranoside]-24-O-{[β-D-xylopyranosyl-(1→6)]-[β-D-glucopyranosyl-(1→2)]-β-D-glucopyranoside} (CC-00489) was determined compared to a sucrose reference.

DETAILED DESCRIPTION

1. Reference: 8%. 9%, and 10% sucrose in DI water.
2. Sweetness of the sample was measured compared to sucrose reference.
3. Test method: Sip & Spit
4. Other temporal profile: Bitterness, astringent, sweet linger, bitter aftertaste
5. Tested level of CC-00489 was 400 ppm.
6. Batch number of CC-00489 was IN-SDV-D-196-2.

Sample Preparation

TABLE 1

| 400 ppm of CC-00489 in DI water | |
|---|---|
| Ingredient | Amount |
| CC-00489 | 2.5 mg |
| DI Water | 6.25 g |

TABLE 2

| Sucrose in DI water | | | |
|---|---|---|---|
| Ingredient | 8% Sucrose | 9% Sucrose | 10% Sucrose |
| Sucrose | 8 g | 9 g | 10 g |
| DI Water | 92 g | 91 g | 90 g |

Ingredients were added to DI water while stirring until solids were visibly dissolved and the sample was poured into a glass bottle or vial and stored at 4° C.

Taste Evaluation

Taste tests were carried out with two panelists. Bottles/vials were removed from the refrigerator. About 25 ml of sucrose solution was poured into 4 oz-plastic cups and 3 mL of sweetener solution was poured into 2 oz-plastic cups. Panelists were given mineral water to rinse their mouth before tasting and between tasting different samples. Unsalted crackers were also given to panelist to eat followed by rinsing the mouth with mineral water before tasting the next sample.

Initially, panelists were asked to check the sweetness of three sucrose solution in DI water (Table 2).

A sample of Compound A in DI water (Table 1) was given to panelists. Panelists were asked to measure the sweetness of samples compared to sucrose reference (Table 2) and describe any taste profile, such as bitterness, astringent, and bitter aftertaste. Panelists were instructed to sip, evaluate the sweetness, and then spit the sample in cups provided for that purpose.

One panelist assessed the sweetness of the sample of Compound A as 9-10 sucrose equivalence (SE) with weak astringency and good mouthfeel. The other panelist assessed the sweetness of the sample as close to 10 SE.

Example 4: Purification with C18 Resin

Mogrosides of interest (e.g. CC-00520) were isolated following bioconversion of MV 90 (90% Mogroside V) substrate (Hunan Huacheng Biotech Inc.) to Siamenoside I using a beta-galactosidase enzyme (e.g. *Aspergillus oryzae* beta-galactosidase (AoBG) such as Maxilact A4).

340 g of MV 90 was dissolved in 1 L of potassium phosphate buffer (100 mM, pH 6.5) and diluted with 1 L of water (total 2 L with a final buffer concentration of 50 mM). This was then filtered through a 0.2 μm sterile filter unit.

6 L of recently concentrated Maxilact A4 (3.5× concentrated) was diluted with 6 L of buffer (potassium phosphate 100 mM, pH 6.5) and the pH of the diluted enzyme was adjusted to ~6.0. 1% of filter aid (Celite; w/v) was added and the suspension mixed for ~15 minutes. The suspension was then filtered over a tub equipped with a coarse frit. The filtrate was passed through a series of capsule filters (5 μm and 0.2 μm) before final filtration in to sterile filtration units. The final volume of filtered enzyme was ~11 L.

11 L of sterile filtered enzyme and 2 L of sterile Mog. V solution was independently transferred to the fermenter. The pH was adjusted to 6.2 and the reaction temperature was adjusted to 50° C. and the reaction initiated.

After the bioconversion reactions, the mogroside of the present invention was separated from the enzyme and salts. In order to separate the protein from the mogroside, the reaction mixture was mixed with sodium hydroxide, increasing the pH to 12.4. Ethanol was added, making a 20% ethanolic solution. The mixture was filtered through a 10 kDa Koch Romicon membrane, with a 1.7 barg inlet pressure, and atmospheric at the outlet. The pH of the permeate was lowered to 5.5 using acetic acid and cooled overnight. The next day the solution was refiltered through a 10 kDa Koch Romicon membrane.

The water, ethanol and salts were removed using a nanofiltration membrane Koch SR3D with a 200 Da cutoff. The solution was diafiltered until the ethanol concentration was less than 3 percent, and was concentrated to 20-30 L. The concentrated mogrosides were mixed with water/Ammonia Acetate solution, making the solution up to ~110 L.

The mixture was passed through a Biotage SNAP KP-C18-HS 400 g guard cartridge. The resulting solution was mixed and aliquoted into a 5 L HDPE jerry cans.

Chromatography

There are six stages for the chromatography separation:

1) Column equilibration, to prepare for loading.
2) Column loading. The charge is followed by the small amount of Equilibration solution to distribute the mogrosides across the bed.
3) removal of the Mogroside V, and the other early eluting compounds. The first ~120 L was sampled and sent to waste. The next ~27 kg was collected, with the targeted purity occurring in the last fractions.
4) removal of the Siamenoside I, two large 18 kg fractions, followed by 4×4.5 kg fractions. The last fractions missed purity specification.
5) straight XNS grade ethanol (95%). The first 18 kg for the collection was Mog IIIe fraction.
6) straight XNS grade ethanol to clean the column.

The composition of the eluants are shown in Table 14.

TABLE 14

| Column Eluent Mix | | | | |
|---|---|---|---|---|
| | RO, 5 mMol $NH_4Ac$ [w/w %] | Ethanol [w/w %] | Mass [kg] | Stage |
| Equilibria | 97.6 | 2.4 | 36.57 | Preparation |
| Load | 97.6 | 2.4 | 4.7 | Loading |
| Eluent pre Sia Collection | 77.4 | 22.6 | 120 + 27 | Mog V |
| Eluent during Sia Collection | 74.8 | 25.2 | 54 | Siamenoside |
| Ethanol Cleanup | 5.0 | 95.0 | 18 | Mog IIIE |
| | 5.0 | 95.0 | 10 | Waste |

Diafiltration

Fraction(s) containing the mogroside of the present invention were processed further. Fractions containing the mogroside of the present invention were identified by, e.g. HPLC-MS techniques and typically eluted with Siamenoside I. Ethanol and ammonia acetate were removed. Combined fractions were diafiltered and RO water was added to the solution to keep the ethanol concentration below 15%. The ammonia, acetate, ethanol and water were removed.

Secondary HPLC chromatography was performed on, e.g. another C18 column, to further purify the mogroside of the present invention. Fractions were freeze dried for analysis and storage.

Example 5: Synthesis of Cc-00491

3-O-β-D-Glucopyranosyl mogrol 24-O-β-D-glucopyranosyl-(1→2)-α-L-rhamnopyranosyl-(1→6)-β-D-glucopyranoside (Scheme 1). To a solution of 6 (562.5 mg, 0.24 mmol) in dry THF (10 mL) and dry MeOH (10 mL) was added dropwise 0.5 M solution of NaOMe in MeOH (0.24 mL, 0.12 mmol) at room temperature under $N_2$ atmosphere. The mixture was stirred at the same temperature for 18 h, neutralized with a 10% AcOH aqueous solution and concentrated under reduced pressure. The residual white solid was purified by preparative HPLC (Phenomenex Luna C18 column, 250×30 mm, 10 μm particles, $H_2O$→$CH_3CN$ gradient, 40 mL/min, $t_R$=12.5 min). Fractions with retention time between 11-15 min were collected and combined based on HPLC and LCMS analysis. The product was re-dissolved in water and dried in lyophilizer to give 7 (172 mg, 64%) as a white powder. mp=179-182° C. $R_f$=0.56 (silica gel, $CH_2Cl_2$/MeOH/$H_2O$=5:4:1). $^1H$ NMR (500 MHz, pyridine-$d_5$) δ 7.53 (d, J=5.0 Hz, 1H), 7.51 (d, J=3.0 Hz, 1H), 7.44 (d, J=3.0 Hz, 1H), 7.30 (d, J=3.8 Hz, 1H), 7.19-7.12 (m, 2H), 7.11-6.99 (m, 2H), 6.65-6.53 (m, 2H), 6.46 (d, J=6.2 Hz, 1H), 6.22-6.13 (m, 1H), 5.66 (d, J=5.8 Hz, 1H), 5.47 (d, J=6.4 Hz, 1H), 5.46 (d, J=1.1 Hz, 1H), 5.43 (t, J=5.9 Hz, 1H), 5.36 (d, J=7.8 Hz, 1H), 5.16 (s, 1H), 5.04 (d, J=7.8 Hz, 1H), 4.91 (d, J=7.8 Hz, 1H), 4.70-4.65 (m, 1H), 4.64 (d, J=9.7 Hz, 1H), 4.60-4.48 (m, 3H), 4.46-4.32 (m, 3H), 4.31-4.21 (m, 5H), 4.20-4.01 (m, 6H), 4.01-3.92 (m, 4H), 3.92-3.86 (m, 1H), 3.68 (s, 1H), 3.02-2.88 (m, 1H), 2.86-2.72 (m, 1H), 2.52-2.39 (m, 1H), 2.36-2.22 (m, 1H), 2.20-1.94 (m, 6H), 1.90-1.78 (m, 3H), 1.78-1.70 (m, 1H), 1.69-1.60 (m, 2H), 1.65 (d, J=6.2 Hz, 3H), 1.59-1.48 (m, 1H), 1.57 (s, 3H), 1.52 (s, 3H), 1.48-1.38 (m, 1H), 1.44 (s, 3H), 1.33 (s, 3H), 1.20-1.11 (m, 1H), 1.14 (s, 3H), 1.10-1.00 (m, 1H), 1.08 (d, J=6.4 Hz, 3H), 0.90 (s, 3H), 0.89 (s, 3H). $^{13}C$ NMR (125 MHz, pyridine-$d_5$) δ 144.5, 118.8, 107.8, 106.6, 103.1, 102.7, 89.2, 88.3, 84.1, 79.1, 78.7, 78.7, 78.5, 78.2, 76.9, 76.5, 75.9, 74.5, 73.1, 72.7, 72.7, 72.5, 72.1, 71.8, 70.1, 68.6, 63.8, 63.4, 51.2, 47.8, 43.9, 42.7, 41.5, 40.5, 37.2, 37.1, 34.9, 34.1, 29.9, 29.3, 28.9, 28.0, 27.3, 27.2, 26.7, 26.7, 26.3, 24.9, 19.7, 19.5, 19.1, 17.4. ESI-MS (negative mode) m/z: $[M-H]^-$ 1108.

Scheme 1.
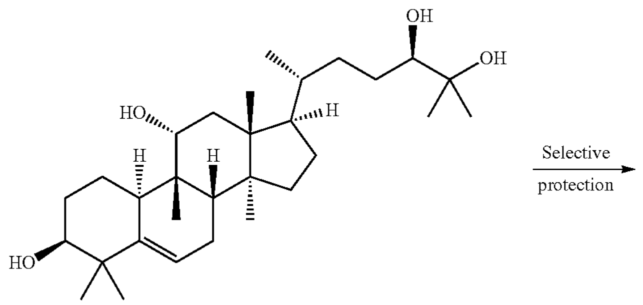
1 Mogrol
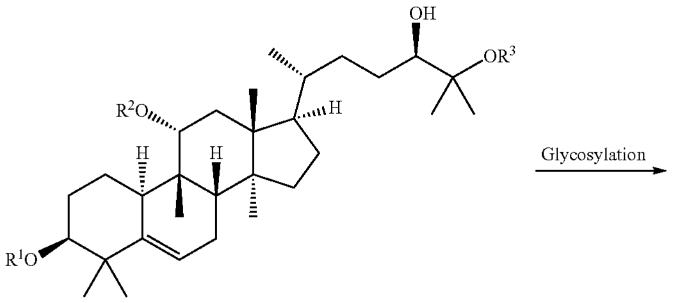
2
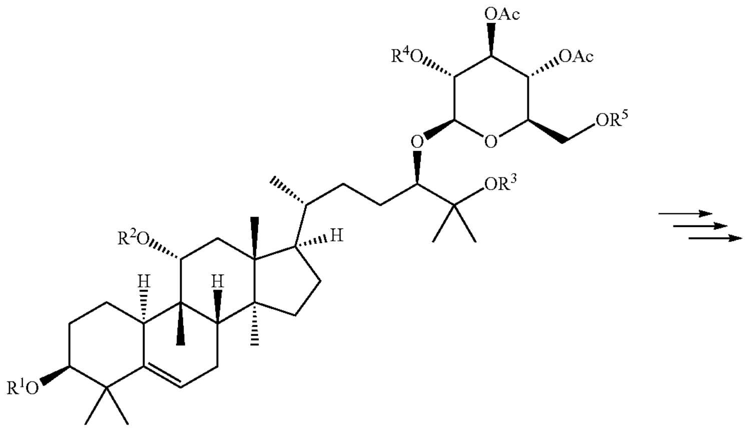
3
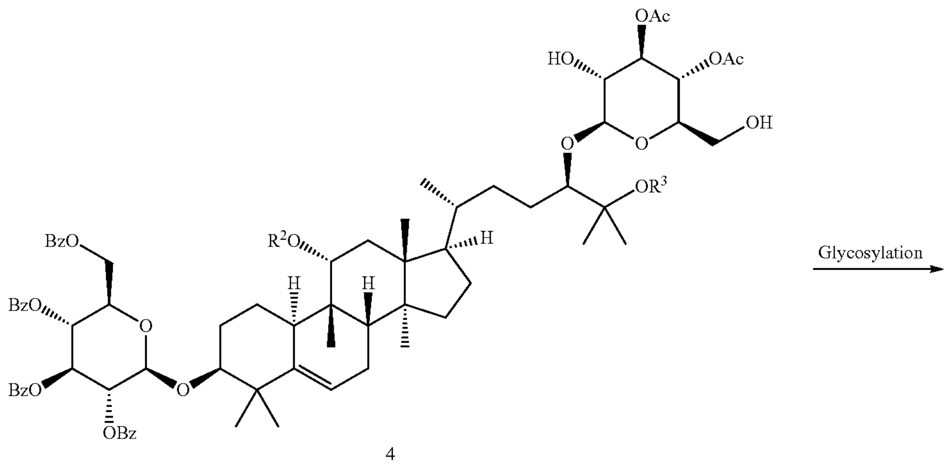
4

-continued
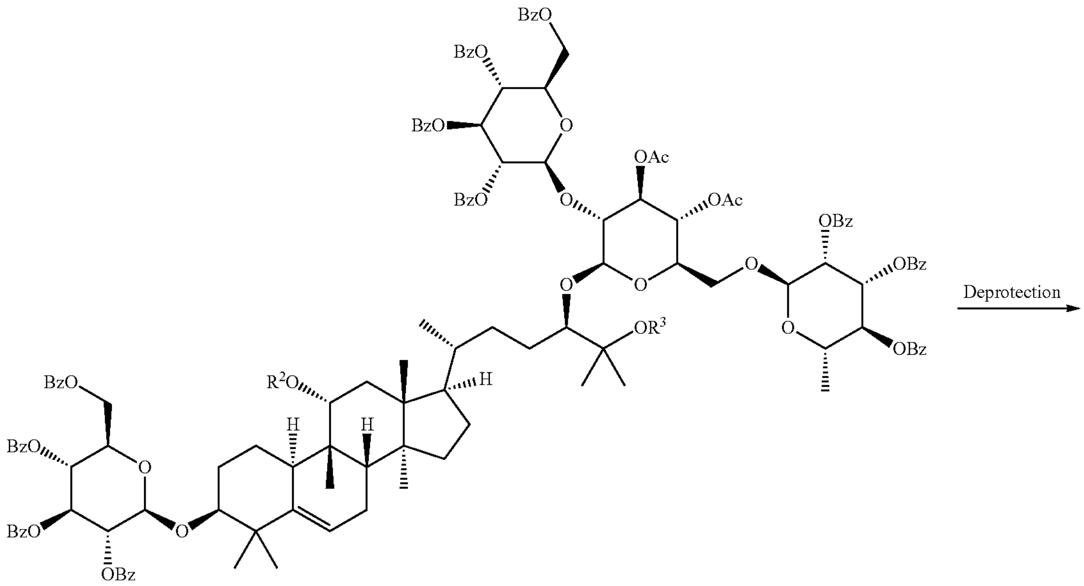
5
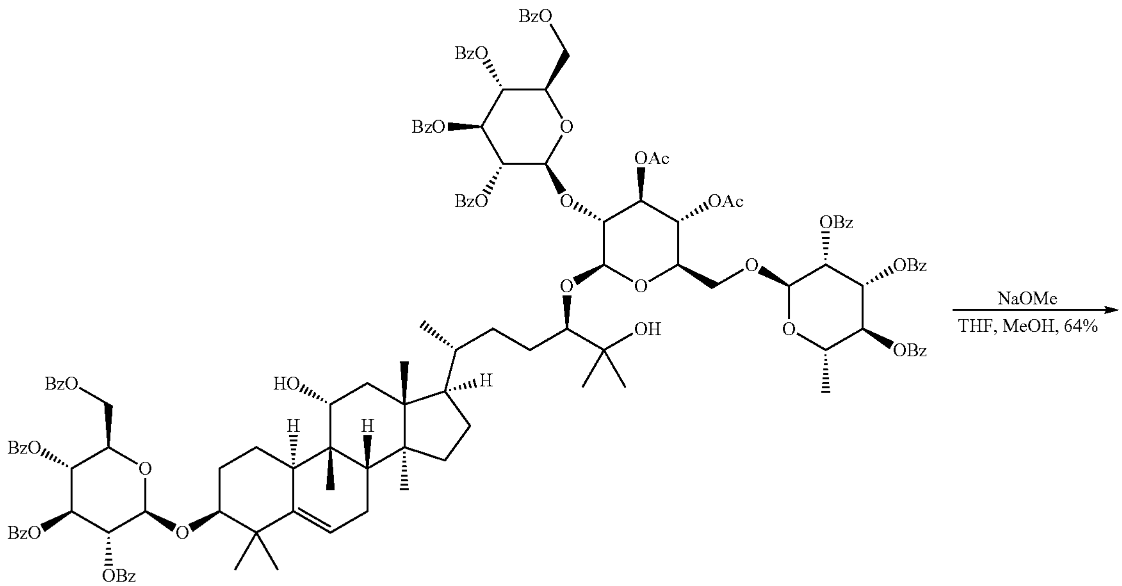
6

-continued

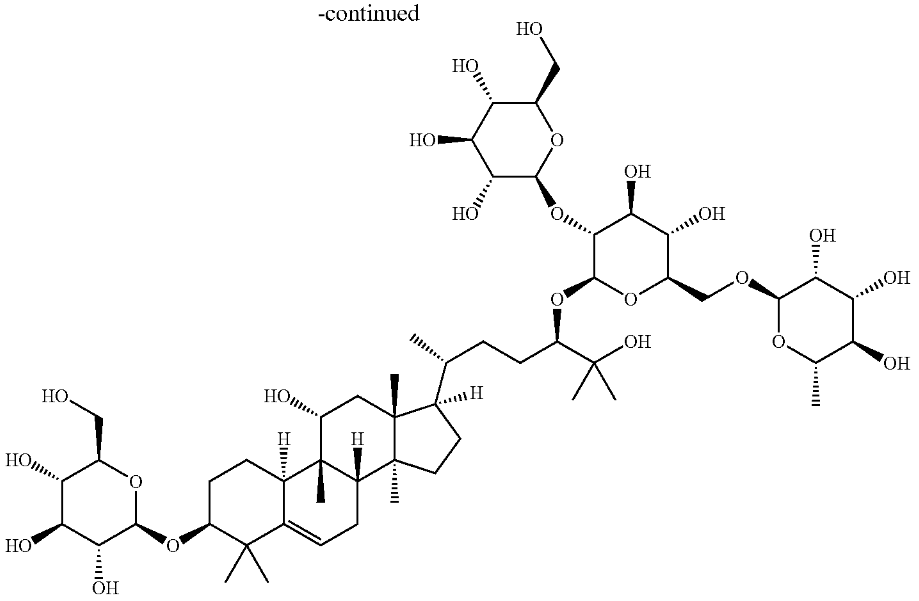

7

Example 6: Purification and Characterization of Cc-00507

Materials: The material used for the isolation of CC-00507 (Lot #IN-RAS-A-53-3) was Luo Han Guo extract (batch #LHGE-180125) purchased from Huacheng Bio.

HPLC Analysis: HPLC analyses were performed on an Agilent 1200 system coupled with variable wavelength detector (VWD) detector. Samples from processing and final purity evaluation were performed using the method conditions described in Table 1.

TABLE 1

| Analytical HPLC conditions for final purity evaluation | | |
|---|---|---|
| Column: | Phenomenex hydro RP 80A (250 × 4.6 mm, 4 μm) | |
| Column Temperature | 55° C. | |
| Sample Temperature | Ambient | |
| Mobile Phase A | 0.285 g of ammonium acetate + 0.1145 g of acetic acid in water | |
| Mobile Phase B | Acetonitrile | |
| Flow Rate | 0.5 mL/min | |
| Injection Volume | 20 μL | |
| Detection @ UV | 215 nm | |
| Runtime | 27.5 min | |
| Gradient | | |
| Time (min) | % A | % B |
| 0 | 75 | 25 |
| 15 | 55.2 | 44.8 |
| 18 | 40 | 60 |
| 20 | 20 | 80 |
| 22 | 10 | 90 |
| 23 | 10 | 90 |
| 23.5 | 75 | 25 |
| 27.5 | 75 | 25 |

Preparative HPLC Analysis: Preparative HPLC analyses were performed on an Agilent preparative HPLC coupled with a UV-Vis detector.

Primary Processing: Approximately 109 g of Luo Han Guo extract (batch #LHGE-180125) was processed using the preparative HPLC method described in Table 2. The target fraction retention time was 20.00-23.00 minutes (Peak ID: LHGE-180125-P4). This material was pooled and lyophilized. The final yield of Peak ID: LHGE-180125-P4 (Lot #IN-RAS-A-24-4) was ~12.2 g.

TABLE 2

| Preparative HPLC method conditions for primary processing of # LHGE-180125. | | |
|---|---|---|
| Column: | XBridge BEH Prep OBD amide (250 x 30 mm, 5 μm) | |
| Mobile Phase A and B | A: Water and B: Acetonitrile | |
| Flow Rate | 30 mL/min | |
| Injection Volume | 1000 uL | |
| Detection @ UV | 210 nm | |
| Runtime | 30 min | |
| Diluent | Water:Acetonitrile(80:20; % v/v) | |
| Sample preparation | 3.5 g in 8.0 mL of diluent (After adding diluent to the sample, solution was filtered through 0.45 um filter) | |
| Gradient elution | | |
| Time (min) | % A | % B |
| 0 | 20 | 80 |
| 21 | 30 | 70 |
| 25 | 30 | 70 |
| 26 | 20 | 80 |
| 30 | 20 | 80 |
| Time Region for collected Target fraction | RT 20.00 to 23.00 min (Peak ID: LHGE-180125-P4; Lot#IN-RAS-A-24-4) | |

Secondary Processing: Approximately 12.2 g of #LHGE-180125-P4 was processed using the preparative HPLC method described in Table 3. The target fraction had a retention time of 8.60-9.50 minutes (Peak ID: LHGE-180125-P4-D. This material was pooled and lyophilized. The final yield of Peak ID: LHGE-180125-P4-D (Lot #IN-VVP-K-194-4) was ~60 mg.

TABLE 3

| Preparative HPLC method conditions for processing of #LHGE-180125-P4 | |
|---|---|
| Column: | Kinetex EVO C18 100 A° (250 × 21.2 mm, 5 μm) |
| Mobile Phase A and B | A: Water and B: Acetonitrile |
| Flow Rate | 19.0 mL/min |
| Injection Volume | 250 uL |
| Detection @ UV | 210 nm |
| Runtime | 15.0 min |
| Diluent | Water:Acetonitrile(80:20; % v/v) |
| Sample preparation | 0.5 g in 5.0 mL of diluent (After adding diluent to the sample, solution was filtered through 0.45 um filter) |

| Gradient elution | | |
|---|---|---|
| Time (min) | % A | % B |
| 0 | 77 | 23 |
| 11 | 71.5 | 28.5 |
| 11.1 | 10 | 90 |
| 12 | 10 | 90 |
| 12.1 | 77 | 23 |
| 14 | 77 | 23 |

| | |
|---|---|
| Time Region for collected Target fraction | RT 8.60 to 9.50 min (Peak ID: LHGE-180125-P4-D; Lot#IN-VVP-K-194-4) |

Tertiary Processing: Approximately 60 mg of #LHGE-180125-P4-D was processed using the preparative HPLC method described in Table 4. The target fraction had a retention time of 7.20-7.60 minutes (Peak ID: LHGE-180125-P4-D3. The material was pooled and lyophilized for isolation. The final yield of Peak ID: LHGE-180125-P4-D3 (Lot #IN-RAS-A-53-3) was 4.4 mg with purity 90.6% (area %).

TABLE 4

| Preparative HPLC method conditions for processing of #LHGE-180125-P4-D | |
|---|---|
| Column: | Kinetex EVO C18 100 A° (250 × 21.2 mm, 5 μm) |
| Mobile Phase A and B | A: Water and B: Acetonitrile |
| Flow Rate | 19.0 mL/min |
| Injection Volume | 250 uL |
| Detection @ UV | 205 nm |
| Runtime | 12.0 min |
| Diluent | Water:Acetonitrile(80:20; % v/v) |
| Sample preparation | 60 mg in 4.0 mL of diluent (After adding diluent to the sample, solution was filtered through 0.45 um filter) |

| Gradient elution | | |
|---|---|---|
| Time (min) | % A | % B |
| 0 | 80 | 20 |
| 12 | 70 | 30 |

| | |
|---|---|
| Time Region for collected Target fraction | RT 7.20 to 7.60 min (Peak ID: LHGE-180125-P4-D3; Lot#IN-RAS-A-53-3) |

MS and MS/MS. MS and MS/MS data were generated with a Waters QT of Micro mass spectrometer equipped with an electrospray ionization source. The sample was analyzed by negative ESI. The sample (~0.2 mg) was diluted with 50:50 ACN:$H_2O$ to a concentration of ~0.2 mg/mL and introduced via direct infusion.

Mass Spectrometry. The ESI-TOF mass spectrum acquired by infusing a sample of CC-00507 showed a $[M-H]^-$ ion at m/z 1255.6326. The mass of the $[M-H]^-$ ion was in good agreement with the molecular formula $C_{59}H_{100}O_{28}$ (calcd for $C_{59}H_{99}O_{28}$: 1255.6323, error: 0.2 ppm) expected. The MS data confirmed that CC-00507 has a nominal mass of 1256 Daltons with the molecular formula, $C_{59}H_{100}O_{28}$. The ion observed at m/z 1353.6130 is most likely due to $[M-H+H_3PO_4]^-$.

The MS/MS spectrum of CC-00507, selecting the $[M-H]^-$ ion at m/z 1255.5 for fragmentation, indicated loss of xylose unit at m/z 1123.5382 followed by sequential loss of four glucose units at m/z 961.4853, 799.4445, 637.3991 and 475.3554. Following the loss of xylose unit from the structure, an alternative fragmentation pathway is also observed in the spectrum which would correspond to loss of water molecule from the central triterpene core followed by sequential loss of sugar units at m/z 1105.5109, 943.4888, 781.4421 and 619.3909.

NMR. The sample was prepared by dissolving the available material in 130 μL of $CD_3OD$ and NMR data were acquired. The $^1H$, $^1H$-$^1H$ COSY, $^1H$-$^{13}C$ HSQC-DEPT and 1D TOCSY NMR data were acquired on a Bruker Avance 500 MHz NMR instrument equipped with a 2.5 mm inverse probe. Due to little sample concentration, additional NMR data such as $^{13}C$, $^1H$-$^{13}C$ HMBC and $^1H$-$^1H$ ROESY were acquired at the Rensselaer Polytechnic Institute using their Bruker Avance 600 MHz instrument with a 5 mm cryo-probe. The $^1H$ NMR spectrum was referenced to the $CHD_2OD$ resonance at $\delta_H$ 3.30 and $^{13}C$ NMR spectrum was referenced to the $CD_3OD$ resonance at $\delta_C$ 49.0.

TABLE 5

$^1H$ and $^{13}C$ NMR (500 and 125 MHz, $CD_3OD$), assignments of the CC-00507 aglycone.

| Position | $^{13}C$ | $^1H$ |
|---|---|---|
| 1 | 27.2 | 1.48 m |
| | | 2.22 m |
| 2 | 29.7 | 1.89 m |
| | | 1.93 m |
| 3 | 88.2 | 3.46 m |
| 4 | 42.9 | — |
| 5 | 145.1 | — |
| 6 | 119.6 | 5.48 brd (5.5) |
| 7 | 25.1 | 1.81 m |
| | | 2.38 m |
| 8 | 44.7 | 1.66 m |
| 9 | 40.9 | — |
| 10 | 37.3 | 2.49 brd (11.6) |
| 11 | 79.4 | 3.85 m |
| 12 | 41.1 | 1.81 m |
| | | 1.86 m |
| 13 | 48.3 | — |
| 14 | 50.6 | — |
| 15 | 35.4 | 1.13 m |
| | | 1.20 m |
| 16 | 29.3 | 1.32 m |
| | | 1.97 m |
| 17 | 51.8 | 1.62 m |
| 18 | 17.1 | 0.91 s |
| 19 | 26.2[¥] | 1.10 s[A] |
| 20 | 37.7 | 1.43 m |
| 21 | 19.1 | 0.95 brd (6.4) |
| 22 | 34.0 | 1.40 m |
| | | 1.65 m |
| 23 | 30.1 | 1.34 m |
| | | 1.54 m |
| 24 | 93.2 | 3.36 m |
| 25 | 73.9 | — |
| 26 | 26.7[†] | 1.10 s[†, A] |
| 27 | 24.1[†] | 1.13 s[†] |
| 28 | 28.0 | 1.08 s |

TABLE 5-continued

| $^1$H and $^{13}$C NMR (500 and 125 MHz, $CD_3OD$), assignments of the CC-00507 aglycone. | | |
|---|---|---|
| Position | $^{13}$C | $^1$H |
| 29 | 26.2¥ | 1.18 s |
| 30 | 20.0 | 0.88 s |

†Assignments can be interchanged.

¥Two carbon resonances at 26.2 ppm (26.20 and 26.24 ppm), hence chemical shifts could not be unequivocally assigned.

λPartially overlapped methyl resonances at 1.10 ppm (2D NMR data confirmed that H-19 observed at 1.104 ppm and H-26 observed at 1.097 ppm).

TABLE 6

| $^1$H and $^{13}$C NMR (500 and 125 MHz, $CD_3OD$), assignments of the CC-00507 C-3 glycoside. | | |
|---|---|---|
| Position | $^{13}$C | $^1$H |
| $Glc_{IV}$-1 | 106.4 | 4.28 d (7.7) |
| $Glc_{IV}$-2 | 75.6 | 3.19 m |
| $Glc_{IV}$-3 | 77.7-78.1§ | ~3.30 m |
| $Glc_{IV}$-4 | 71.5-71.6λ | ~3.30 m |
| $Glc_{IV}$-5 | 77.3 | 3.40 m |
| $Glc_{IV}$-6 | 69.7 | 3.80 m, 4.05 m |
| $Glc_{V}$-1 | 104.8 | 4.42 d (8.0) |
| $Glc_{V}$-2 | 75.2€ | 3.18 m |
| $Glc_{V}$-3 | 77.7-78.1§ | 3.35 m |
| $Glc_{V}$-4 | 71.5-71.6λ | 3.28 m |
| $Glc_{V}$-5 | 77.7-78.1§ | ~3.26 m |
| $Glc_{V}$-6 | 62.7¥ | 3.65 m, 3.85 m |

§Six carbon resonances in the range of 77.7-78.1 ppm (77.68, 77.93, 78.00 and 78.14 ppm; two additional carbons overlap in this region), hence chemical shifts could not be unequivocally assigned.

λFour carbon resonances in the range of 71.5-71.6 ppm (71.48, 71.58, 71.61 and 71.64 ppm), hence chemical shifts could not be unequivocally assigned.

€Two carbon resonances overlap at 75.2 ppm, hence chemical shifts could not be unequivocally assigned.

¥Two carbon resonances overlap at 62.7 ppm, hence chemical shifts could not be unequivocally assigned.

TABLE 7

| $^1$H and $^{13}$C NMR (500 and 125 MHz, $CD_3OD$), assignments of the CC-00507 C-24 glycoside. | | |
|---|---|---|
| Position | $^{13}$C | $^1$H |
| $Glc_{I}$-1 | 104.1 | 4.40 d 8.2) |
| $Glc_{I}$-2 | 82.7 | 3.48 m |
| $Glc_{I}$-3 | 78.5 | 3.57 m |
| $Glc_{I}$-4 | 71.5-71.6λ | 3.33 m |
| $Glc_{I}$-5 | 76.4 | 3.49 m |
| $Glc_{I}$-6 | 70.1 | 3.61 m, 4.23 m |
| Xyl-1 | 106.0 | 4.62 d (7.5) |
| Xyl-2 | 75.8 | 3.25 m |
| Xyl-3 | 77.7-78.1§ | 3.32 m |
| Xyl-4 | 71.2 | 3.49 m |
| Xyl-5 | 67.2 | 3.15 m, 3.84 m |
| $Glc_{II}$-1 | 104.4 | 4.27 d (7.7) |
| $Glc_{II}$-2 | 75.2€ | 3.20 m |
| $Glc_{II}$-3 | 77.7-78.1§ | 3.35 m |
| $Glc_{II}$-4 | 71.5-71.6λ | ~3.27 m |
| $Glc_{II}$-5 | 77.7-78.1§ | ~3.27 m |
| $Glc_{II}$-6 | 62.7¥ | 3.64 m, 3.84 m |

λFour carbon resonances in the range of 71.5-71.6 ppm (71.48, 71.58, 71.61 and 71.64 ppm), hence chemical shifts could not be unequivocally assigned.

§Six carbon resonances in the range of 77.7-78.1 ppm (77.68, 77.93, 78.00 and 78.14 ppm; two additional carbons overlap in this region), hence chemical shifts could not be unequivocally assigned.

€Two carbon resonances overlap at 75.2 ppm, hence chemical shifts could not be unequivocally assigned.

¥Two carbon resonances overlap at 62.7 ppm, hence chemical shifts could not be unequivocally assigned.

Spectroscopic (NMR) and spectrometric (MS) analysis of CC-00507 allowed full assignment of its structure identified as mogrol-3-O-[{β-D-glucopyranosyl-(1→6)}-β-D-glucopyranoside]-24-O-[{β-D-xylopyranosyl-(1→2)}-{β-D-glucopyranosyl-(1→6)}-β-D-glucopyranoside]. This compound bears four glucose units and one xylose unit. The xylose unit is linked to $Glc_I$ by forming 1→2 sugar linkage.

Example 7: Preparation and Characterization of CC-00518

CC-00518 was isolated from the reaction product of the bioconversion of Mogroside $III_E$ with α-D-Xylosyl fluoride and α-xylosidase (Megazyme, E-AXSEC). The bioconversion had the following reaction conditions: 10 mM α-xylosyl fluoride, 10 mM MogIIIE, 0.01% BSA, 6 Units α-xylosidase, in 50 mM phosphate buffer (pH 7.0) at 37° C. for about 30 min. CC-00518 was purified using multiple rounds of preparative HPLC to provide about 25 mg with a purity of 99% (area %). A series of 1D and 2D experiments ($^1$H, $^{13}$C, $^1$H-$^1$H COSY, $^1$H-$^{13}$C HSQC-DEPT, $^1$H-$^{13}$C HSQC-TOCSY, and $^1$H-$^{13}$C HMBC) to elucidate the structure as mogrol-3-O-[α-D-xylopyranosyl-(1→6)-β-D-glucopyranoside]-24-O-[α-D-xylopyranosyl-(1→6)β-D-glucopyranoside]. Spectral data indicated the presence of a central triterpene core and four sugar units in the structure: three glucose and one xylose. The linkages between the sugar units and their attachment to the central triterpene core were determined based on COSY, TOCSY, and HSQC-DEPT data. The glucose units exist as the 13 anomers while the xylose unit ($^3$J=3.7 Hz) exists in the α configuration.

TABLE 1

| $^1$H NMR (500.13 MHz, $CD_3OD$) and $^{13}$C NMR (125 MHz) assignments of CC-00518. | | | |
|---|---|---|---|
| Sugar | Position | $^1$H Chemical Shift | $^{13}$C Chemical Shift |
| | 1 | 2.20, 1.53 | 27.2 |
| | 2 | 1.93 | |
| | 3 | 3.43 | 88.8 |
| | 4 | | 42.8 |
| | 5 | | 144.8 |
| | 6 | 5.49 | 119.7 |
| | 7 | 2.39 (dd), 1.82 (dd) | 25.1 |
| | 8 | 1.67 | 44.7 |
| | 9 | | 40.9 |
| | 10 | 2.49 | 37.3 |
| | 11 | 3.85 | 79.4 |
| | 12 | 1.85, 1.82 | 40.9 |
| | 13 | | 48.2 |
| | 14 | | 50.6 |
| | 15 | 1.21, 1.15 | 35.4 |
| | 16 | 2.00, 1.33 | 29.3 |
| | 17 | 1.63 | 51.6 |
| | 18 | 0.92 | 17.1 |
| | 20 | 1.47 | 37.5 |
| | 21 | 0.98 (d) | 19.3 |
| | 22 | 1.51, 1.49 | 34.5 |
| | 23 | 1.64 | 29.3 |
| | 24 | 3.48 | 89.4 |
| | 25 | | 73.7 |
| | 26 | 1.15 (s) | |
| | 27 | 1.18 (s) | |
| | 28 | 1.07 (s) | 27.9 |
| | 29 | 1.20 (s) | 26.3 |
| | 30 | 0.88 (s) | 19.9 |
| Glc I | 1 | 4.29 (d), $^3$J = 7.8 Hz | 106.3 |
| | 2 | 3.22 (t) | 75.6 |
| | 3 | 3.32 (t) | 78.4 |
| | 4 | 3.37 (t) | 71.6 |
| | 5 | 3.43 (m) | 76.3 |
| | 6 | 3.87, 3.63 | 67.8 |
| Glc II | 1 | 4.48 (d), $^3$J = 7.4 Hz | 102.8 |
| | 2 | 3.52 (t) | 82.4 |
| | 3 | 3.55 (t) | 78.4 |
| | 4 | 3.32 (t) | 71.3 |
| | 5 | 3.27 (m) | 78.2 |
| | 6 | 3.85, 3.64 | 62.6 |
| Glc III | 1 | 4.66 (d), $^3$J = 7.8 Hz | 105.1 |
| | 2 | 3.28 (t) | 75.7 |
| | 3 | 3.37 (t) | 78.0 |
| | 4 | 3.24 (t) | 72.1 |

TABLE 1-continued

| $^1H$ NMR (500.13 MHz, $CD_3OD$) and $^{13}C$ NMR (125 MHz) assignments of CC-00518. | | | |
|---|---|---|---|
| Sugar | Position | $^1H$ Chemical Shift | $^{13}C$ Chemical Shift |
| | 5 | 3.27 (m) | 78.1 |
| | 6 | 3.86, 3.66 | |
| Xyl I | 1 | 4.78 (d), $^3J$ = 3.7 Hz | 100.4 |
| | 2 | 3.33 | 73.9 |
| | 3 | 3.59 | 75.2 |
| | 4 | 3.47 | 71.6 |
| | 5 | 3.56, 3.52 | 63.0 |

Example 8: Preparation, Purification and Characterization of CC-00520

CC-00520 was isolated as a minor mogroside from the conversion of Mogroside V to Siamenoside I, e.g. Example 4. The compound an also be found in and isolated from Monk fruit extract.

Materials: The material used for the isolation of Lot #IN-VVP-K-172 (CC-00520) was a R11 purified sample and Lot #AMR100489-23-F2.

The material used for the isolation of Lot #IN-RAS-A-119-3 (CC-00520) was Monk Fruit extract sample, Lot #LHGE-180125.

HPLC Analysis: HPLC analyses were performed on an Agilent 1200 system coupled with Variable wave length (VWD) detector. Samples from multiple process and final purity evaluation were performed using the method conditions described in Table 1 and Table 2.

TABLE 1

| Analytical HPLC conditions for fraction analysis in multiple processes and final purity evaluation | | | |
|---|---|---|---|
| Column | Phenomenex Hydro RP 80A (250 × 4.6 mm, 4 μm) | | |
| Column Temperature | 55° C. | | |
| Sample Temperature | Ambient | | |
| Mobile Phase A | 0.2845 g of Ammonium acetate + 0.1145 g of Acetic acid in water | | |
| Mobile Phase B | Acetonitrile | | |
| Flow Rate | 0.5 mL/min | | |
| Injection Volume | 10 μL | | |
| Sample concentration | 0.5 mg/mL | | |
| Detection @ UV | 210 nm | | |
| Runtime | 27.5 min | | |
| Gradient | Time (min) | % A | % B |
| | 0 | 75 | 25 |
| | 15 | 55.2 | 44.8 |
| | 18 | 40 | 60 |
| | 20 | 20 | 80 |
| | 22 | 5 | 95 |
| | 23 | 5 | 95 |
| | 23.5 | 75 | 25 |
| | 27.5 | 75 | 25 |

TABLE 2

| Analytical HPLC conditions for fraction analysis in multiple processes and final purity evaluation | |
|---|---|
| Column | Phenomenex Luna Omega (150 × 4.6 mm, 5 μm) |
| Column Temperature | 55° C. |
| Sample Temperature | Ambient |
| Mobile Phase A | 10 mM Ammonium formate in water |
| Mobile Phase B | Acetonitrile |

TABLE 2-continued

| Analytical HPLC conditions for fraction analysis in multiple processes and final purity evaluation | | | |
|---|---|---|---|
| Flow Rate | 1.0 mL/min | | |
| Injection Volume | 10 μL | | |
| Detection @ UV | 215 nm | | |
| Runtime | 53 min | | |
| Gradient | Time (min) | % A | % B |
| | 0 | 85 | 15 |
| | 28.5 | 75 | 25 |
| | 30 | 71 | 29 |
| | 36.5 | 70 | 30 |
| | 38 | 66 | 34 |
| | 44 | 66 | 34 |
| | 46.5 | 48 | 52 |
| | 47 | 48 | 52 |
| | 48 | 30 | 70 |
| | 50 | 30 | 70 |
| | 50.1 | 85 | 15 |
| | 53 | 85 | 15 |

Primary Processing: Approximately 68 g of Lot #AMR100489-23-F2 was processed using the primary preparative HPLC method described in Table 3. Fraction of Peak ID: AMR100489-23-F2-P2 (Lot #IN-SDV-D-168-2) (Time region for collected fraction RT 13.0 to 13.8 min) was pooled and lyophilized. The final yield of Peak ID: AMR100489-23-F2-P2 (Lot #IN-SDV-D-168-2) was 1.4 g.

TABLE 3

| Preparative HPLC method conditions for primary processing of Lot#AMR100489-23-F2 | | |
|---|---|---|
| Column | YMC Trait C18 (150 × 30.0 mm, 5 μm) | |
| Column Temperature | Ambient | |
| Mobile Phase A | Water | |
| Mobile Phase B | Acetonitrile | |
| Flow Rate | 30.0 mL/min | |
| Detection @ UV | 215 nm | |
| Runtime | 28.0 min | |
| Diluent | Water:Acetonitrile (80:20; % v/v) | |
| Sample preparation | Approximately 1 g dissolved in 10 mL of diluent | |
| Injection Volume/Loading | 4.5 mL (~450 mg) | |
| Elution | Gradient | |
| Gradient | Time (min) | % B |
| | 0 | 20 |
| | 20 | 30 |
| | 22 | 90 |
| | 24 | 90 |
| | 25 | 20 |
| | 28 | 20 |
| Time region for collected Target fraction | RT 13.0 to 13.8 min (Peak ID: AMR10049-23-F2-P2; Lot# IN-SDV-D-168-2) | |

Approximately 109 g of Lot #LHGE-180125 was processed using the primary preparative HPLC method described in Table 4. Fraction of Peak ID: LHGE-180125-P6 (Lot #IN-RAS-A-24-6) (Time region for collected fraction RT 25.5 to 29.0 min) was pooled and lyophilized. The final yield of Peak ID: LHGE-180125-P6 (Lot #IN-RAS-A-24-6) was 5.5 g.

TABLE 4

| Preparative HPLC method conditions for primary processing of Lot #LHGE-180125 | | |
|---|---|---|
| Column | XBridge BEH Prep OBD Amide (250 × 30 mm, 5 μm) | |
| Mobile Phase A | Water | |
| Mobile Phase B | Acetonitrile | |
| Column and Sampler Temperatures | Ambient | |
| Run time | 30 min | |
| Flow | 30 mL/min | |
| Diluent | Water/Acetonitrile-(80/20; % v/v) | |
| Detection @ UV | 210 nm | |
| Sample preparation | 3.5 g dissolved in 8 mL | |
| Inj. Volume/Loading | 1 mL/~430 mg | |
| Elution | Gradient | |
| Gradient | Time (min) | % B |
| | 0 | 80 |
| | 21 | 70 |
| | 25 | 70 |
| | 26 | 80 |
| | 30 | 80 |
| Time region for collected Target fraction | 25.5 to 29.0 min (Peak ID: LHGE-180125-P6; Lot# IN-RAS-A-24-6 | |

Secondary Processing: Approximately 1.4 g of Peak ID: AMR100489-23-F2-P2 (Lot #IN-SDV-D-168-2) was processed using preparative HPLC method conditions described in Table 5. Fraction of peak ID: AMR100489-23-F2-P2-G (Time region for collected fraction RT 26.0 to 27.0 min) collected from the secondary processing of #AMR100489-23-F2-P2 was pooled up and lyophilized for isolation as described in Section 3.8. The final yield of Peak ID: AMR100489-23-F2-P2-G (Lot #IN-VVP-K-138-7) was 34 mg with 89.0% (area %) purity.

TABLE 5

| Preparative method conditions for secondary processing of peak ID; AMR100489-23-F2-P2 (Lot#IN-SDV-D-168-2) | | |
|---|---|---|
| Column | XBridge BEH PrepOBD amide (250 × 30 mm, 5 μm) | |
| Column Temperature | Ambient | |
| Mobile Phase A | Water | |
| Mobile Phase B | Acetonitrile | |
| Flow Rate | 30.0 mL/min | |
| Detection @ UV | 215 nm | |
| Run time | 26.0 min | |
| Diluent | Water:Acetonitrile (80:20; % v/v) | |
| Sample Preparation | Dissolved 200 mg of sample in 3 mL of the diluent | |
| Inj. Volume/Loading | 700 μL (~40 mg) | |
| Gradient | Time | % B |
| | 0 | 78 |
| | 16 | 70 |
| | 21 | 70 |
| | 22 | 78 |
| | 26 | 78 |
| Time region for collected Target fraction | RT 26.0 to 27.0 min (Peak ID: AMR10049-23-F2-P2-G; Lot# IN-VVP-K-137-8) | |

Approximately 5.5 g of Peak ID: LHGE-180125-P6 (Lot #IN-RAS-A-24-6) was processed using preparative HPLC method conditions described in Table 6. Fraction of peak ID: LHGE-180125-P6-B (Time region for collected fraction RT 5.0 to 5.50 min) was pooled and lyophilized. The final yield of Peak ID: LHGE-180125-P6-B (Lot #IN-RAS-A-87-2) was 800 mg.

TABLE 6

| Preparative method conditions for secondary processing of peak ID; LHGE-180125-P6 (Lot#IN-RAS-A-24-6) | | |
|---|---|---|
| Column | Phenomenex EVO, (250 × 21.2 mm, 5 μm) | |
| Column Temperature | Ambient | |
| Mobile Phase A | Water | |
| Mobile Phase B | Acetonitrile | |
| Flow Rate | 20 mL/min | |
| Detection @ UV | 210 nm | |
| Run time | 14 min | |
| Diluent | Water:Acetonitrile (80:20; % v/v) | |
| Sample preparation | ~500 mg dissolved in 7 mL | |
| Inj. Volume/Loading | 250-500 μL/~20-40 mg | |
| Elution | Gradient | |
| Gradient | Time (min) | % B |
| | 0 | 20 |
| | 10.0 | 50 |
| | 11.0 | 70 |
| | 12.0 | 80 |
| | 12.5 | 20 |
| | 14 | 20 |
| Time region for collected Target fraction | RT 5.0 to 5.5 min (Peak ID: LHGE-180125-P6-B; Lot# IN-RAS-A-87-2) | |

Tertiary Processing: Approximately 34 mg of Peak ID: AMR100489-23-F2-P2-G (Lot #IN-VVP-K-138-7) was further processed using preparative HPLC method conditions described in Table 7. The target fraction had a retention time from 6.3 to 6.9 min. The target fraction was pooled and lyophilized. The final yield of high pure Peak ID: AMR100489-23-F2-P2-G (Lot #IN-VVP-K-172) was 13 mg with 95.5% (area %) purity.

TABLE 7

| Preparative method conditions for Tertiary processing of peak ID; AMR100489-23-F2-P2-G (Lot#IN-VVP-K-137-8) | | |
|---|---|---|
| Column | Phenomenex Hydro RP (250 × 21.2 mm, 4 μm) | |
| Column Temperature | Ambient | |
| Mobile Phase A | Water | |
| Mobile Phase B | Acetonitrile | |
| Flow rate | 19.0 mL/min | |
| Detection @ UV | 210 nm | |
| Run time | 16 min | |
| Diluent | Water/Acetonitrile- (80:20; % v/v) | |
| Sample Preparation | Approximately 10 mg in 1 mL of diluent | |
| Inj. Volume/Loading | 200 μL/2 mg | |
| Gradient | Time | % B |
| | 0 | 20 |
| | 12 | 50 |
| | 12.5 | 95 |
| | 13.5 | 95 |
| | 14 | 20 |
| | 16 | 20 |
| Time region for collected Target fraction | RT 6.3 to 6.9 min Peak ID: AMR100489-23-F2-P2-G; Lot# IN-VVP-K-172 | |

Approximately 800 of Peak ID: LHGE-180125-P6-B (Lot #IN-RAS-A-87-2) was processed using preparative HPLC method conditions described in Table 8. The target fraction had a retention time of 23.0 to 25.0 min. The target fraction was pooled and lyophilized. The final yield of Peak ID: LHGE-180125-P6-B7 (Lot #IN-RAS-A-106-7) was 15 mg.

TABLE 8

| Preparative method conditions for Tertiary of peak ID; LHGE-180125-P6-B (Lot#IN-RAS-A-87-2) | |
|---|---|
| Column | Phenomenex Omega 150 × 30 mm, 5 μm |
| Mobile Phase A | Water |
| Mobile Phase B | Acetonitrile |
| Column Temperature | Ambient |
| Flow | 30 mL/min |
| Detection @ UV | 210 nm |
| Run time | 33 min |
| Diluent | Water:Acetonitrile (80:20; % v/v) |
| Sample preparation | ~100 mg dissolved in 2 mL |
| Inj. Volume/Loading | 250 μL/~12 mg |
| Elution | Gradient |

| Gradient | Time | % B |
|---|---|---|
| | 0 | 15 |
| | 25 | 25 |
| | 30 | 29 |
| | 31 | 30 |
| | 31.1 | 15 |
| | 33 | 15 |
| Time region for collected Target fraction | RT 23.0 to 25.0 min (Peak ID: LHGE-180125-P6-B-7; Lot# IN-RAS-A-106-7) | |

Quaternary Processing: Approximately 15 mg of Peak ID: LHGE-180125-P6-B-7 (Lot #IN-RAS-A-106-7) was processed using preparative HPLC method conditions described in Table 9. The target fraction (LHGE-180125-P6-B7-C) had a retention time from 22.0 to 22.8 min. The target fraction was pooled and lyophilized. The final yield of Peak ID: LHGE-180125-P6-B7-C (Lot #IN-RAS-A-119-3) was 0.9 mg with 81.3% (area %) purity.

The collected fractions from the preparative processing were pooled up and lyophilized using Labconco Lyophilizer, (collector temperature maintained at −44° C. under vacuum).

TABLE 9

| Preparative method conditions for Quaternary of peak ID; LHGE-180125-P6-B-7 (Lot#IN-RAS-A-106-7) | |
|---|---|
| Column | XBridge BEH Prep OBD Amide (250 × 30 mm, 5 μm) |
| Column Temperature | Ambient |
| Mobile Phase A | Water |
| Mobile Phase B | Acetonitrile |
| Flow | 30 mL/min |
| Detection @ UV | 200 nm |
| Run time | 32 min |
| Diluent | Water:Acetonitrile (80:20, % v/v) |
| Sample preparation | ~10 mg dissolved in 1.0 mL (For P6-B7) |
| Inj. Volume/Loading | 250 μL |
| Elution | Gradient |

| Gradient | Time | % B |
|---|---|---|
| | 0 | 80 |
| | 25 | 70 |
| | 28 | 70 |
| | 29 | 80 |
| | 32 | 80 |
| Time region for collected Target fraction | RT 22.0 to 22.8 min (Peak ID: LHGE-180125-P6-B-7-C; Lot# IN-RAS-A-119-3) | |

MS and MS/MS. MS and MS/MS data were generated with a Waters QTof Micro mass spectrometer equipped with an electrospray ionization source. The sample was analyzed by negative ESI. The sample (~0.2 mg) was diluted with 50:50 ACN:$H_2O$ to a concentration of ~0.2 mg/mL and introduced via direct infusion.

The ESI-TOF mass spectrum acquired by infusing a sample of CC-00520 showed a $[M-H]^-$ ion at m/z 1417.6843. The mass of the $[M-H]^-$ ion was in good agreement with the molecular formula $C_{65}H_{110}O_{33}$ (calcd for $C_{65}H_{109}O_{33}$: 1417.6851, error: −0.6 ppm) expected.

NMR Spectroscopy. A series of NMR experiments including $^1H$ NMR, $^{13}C$ NMR, $^1H$-$^1H$ COSY, HSQC-DEPT, HMBC, ROESY, and 1D TOCSY were acquired to allow assignment of CC-00520.

TABLE 10

$^1H$ and $^{13}C$ NMR (500 and 125 MHz, $CD_3OD$), assignments of the CC-00520 aglycone.

| Position | $^{13}C$ | $^1H$ |
|---|---|---|
| 1 | 27.2 | 1.48 m |
| | | 2.21 m |
| 2 | 29.6 | 1.87 m |
| | | 1.94 m |
| 3 | 88.5 | 3.41 m |
| 4 | 42.9 | — |
| 5 | 145.0 | — |
| 6 | 119.6 | 5.48 brd (5.9) |
| 7 | 25.1 | 1.80 m |
| | | 2.38 m |
| 8 | 44.7 | 1.66 m |
| 9 | 40.9 | — |
| 10 | 37.2 | 2.48 brd (12.2) |
| 11 | 79.4 | 3.84 m |
| 12 | 41.1 | 1.81 m |
| | | 1.86 m |
| 13 | 48.3 | — |
| 14 | 50.6 | — |
| 15 | 35.4 | 1.13 m |
| | | 1.21 m |
| 16 | 29.4 | 1.32 m |
| | | 1.98 m |
| 17 | 51.8 | 1.61 m |
| 18 | 17.1 | 0.91 s |
| 19 | 26.2 or 26.3 | 1.10 s |
| 20 | 37.5 | 1.45 m |
| 21 | 19.3 | 0.97 d (6.2) |
| 22 | 34.1 | 1.47 m |
| | | 1.56 m |
| 23 | 29.9 | 1.39 m |
| | | 1.54 m |
| 24 | 93.2 | 3.39 m |
| 25 | 73.9 | — |
| 26 | 26.8† | 1.11 s† |
| 27 | 24.2† | 1.14 s† |
| 28 | 27.9 | 1.07 s |
| 29 | 26.2 or 26.3 | 1.17 s |
| 30 | 20.0 | 0.88 s |

†Assignments can be interchanged.

TABLE 2

$^1H$ and $^{13}C$ NMR (500 and 125 MHz, $CD_3OD$), assignments of the CC-00520 C-3 glycoside.

| Position | $^{13}C$ | $^1H$ |
|---|---|---|
| $Glc_{IV}$-1 | 106.4 | 4.30 d (7.9) |
| $Glc_{IV}$-2 | 75.1-75.3$^{\lambda}$ | 3.26 m |
| $Glc_{IV}$-3 | 76.3 | 3.43 m |
| $Glc_{IV}$-4 | 80.6 | 3.65 m |
| $Glc_{IV}$-5 | 75.1-75.3$^{\lambda}$ | 3.49 m |
| $Glc_{IV}$-6 | 68.9 | 3.92 dd (11.4, 3.6), 4.16 br d (8.8) |
| Xyl-1 | 105.2 | 4.48 d (7.8) |
| Xyl-2 | 74.9 | 3.17 m |
| Xyl-3 | 77.7-78.1§ | 3.33 m |
| Xyl-4 | 71.1 | 3.49 m |

TABLE 2-continued $^1H$ and $^{13}C$ NMR (500 and 125 MHz, $CD_3OD$), assignments of the CC-00520 C-3 glycoside.

| Position | $^{13}C$ | $^1H$ |
|---|---|---|
| Xyl-5 | 67.0 | 3.29 m, 3.86 |
| $Glc_V$-1 | 104.9 | 4.44 d (7.7) |
| $Glc_V$-2 | 75.1-75.3$^{\lambda}$ | 3.22 m |
| $Glc_V$-3 | 77.7-78.1$^{\S}$ | 3.35 m |
| $Glc_V$-4 | 71.6$^{\dagger}$ | 3.29 m |
| $Glc_V$-5 | 77.7-78.1$^{\S}$ | 3.27 m |
| $Glc_V$-6 | 62.7$^{\P}$ | 3.66 m, 3.85 m |

$^{\lambda}$Four carbon resonances in the range of 75.1-75.3 ppm (75.09, 75.17, 75.29 and 75.32 ppm), hence chemical shifts could not be unequivocally assigned.
$^{\S}$Seven carbon resonances in the range of 77.7-78.1 ppm (77.67, 77.88, 77.91, 78.06 and 78.14 ppm; two additional carbon resonances overlap in this region), hence chemical shifts could not be unequivocally assigned.
$^{\dagger}$Three carbon resonances in 71.6 ppm (71.55 and 71.60 ppm; two carbons overlapped at 71.60 ppm), hence chemical shifts could not be unequivocally assigned.
$^{\P}$Two carbon resonances at 62.7 ppm (62.71 and 62.73 ppm), hence chemical shifts could not be unequivocally assigned.

CC-00520 was identified as mogrol-3-O-{[β-D-xylopyranosyl-(1→4)]-[β-D-glucopyranosyl-(1→6)]-β-D-glucopyranoside}-24-O-{[β-D-glucopyranosyl-(1→2)]-[β-D-glucopyranosyl-(1→6)-β-D-glucopyranoside}. CC-00520 is related to Mogroside V but differs from it by an additional xylose unit attached to GlcIV by forming a 1→4 sugar linkage.

Example 9: Purification and Characterization of Cc-00539

CC-00539 (Mogrol-3-O-{[β-D-glucopyranosyl-(1→6)]-β-D-glucopyranoside}-24-O-{[α-L-rhamnopyranosyl-(1→2)]-[β-D-glucopyranosyl-(1→6)]-β-D-glucopyranoside}) was isolated from monk fruit (Luo Han Guo) extract containing 90% Mogroside V. The isolation of this compound involved multiple processing methods by preparative HPLC method to give 12 mg (70% purity) of CC-00539. NMR data indicated that the sample contained about 70% CC-00539 and about 30% Mogroside V. $^1H$, $^{13}C$, $^1H$-$^1H$ COSY, $^1H$-$^{13}C$ HSQC-DEPT and $^1H$-$^{13}C$ HMBC data indicated the presence of a central triterpene core and five sugar units in the structure. Complete structure was determined based on $^1H$, $^{13}C$, $^1H$-$^1H$ COSY, 1D-TOCSY, $^1H$-$^{13}C$ HSQC-DEPT and $^1H$-$^{13}C$ HMBC data. In the $^1H$ NMR, in addition to eight methyl protons observed for the central triterpene core, an additional methyl group observed at $\delta_H$ 1.21 (d, J=6.2 Hz) indicated the presence of a rhamnose unit in the structure. 1D and 2D NMR data indicated that the remaining four sugar units were glucose. 1D-TOCSY data for an anomeric proton at $\delta_H$ 5.31 using different mixing times (20-140 msec) confirmed that the methyl proton at $\delta_H$ 1.21 belonged to the same spin system and thus the anomeric proton at $\delta_H$ 5.31 was assigned to rhamnose H-1. The anomeric proton of rhamnose observed at $\delta_H$ 5.31 showed an HMBC correlation to $Glc_I$ C-2 ($\delta_C$ 77.4). The reciprocal HMBC correlation from $Glc_I$ H-2 ($\delta_H$ 3.49) to the anomeric carbon of rhamnose (Sc 102.0) was also observed indicating a 1→2 linkage between rhamnose and $Glc_I$. In the $^1H$ NMR spectrum which was acquired using 500 MHz NMR instrument equipped with a 2.5 mm inverse probe, rhamnose anomeric proton was observed as a broad singlet which indicated α-configuration for rhamnose. Prior to acquiring $^{13}C$ NMR spectrum, when $^1H$ NMR spectrum was acquired using 500 MHz NMR instrument equipped with a 5 mm broad band probe, the spectrum was better resolved and the rhamnose anomeric proton was observed as a broad doublet with coupling value of 1.1 Hz which confirmed the presence of α-configuration for rhamnose. The key $^1H$-$^1H$ COSY and $^1H$-$^{13}C$ HMBC correlations was utilized to confirm the sugar linkages in the structure.

Mass spectral analysis of CC-00539, by Electrospray Ionization Time-of-Flight (ESI-TOF) mass spectrometry in the negative polarity mode showed $[M-H]^-$ ion at m/z 1269.6537. The mass of the $[M-H]^-$ ion was in good agreement with the molecular formula $C_{60}H_{102}O_{28}$ (calcd for $C_{60}H_{100}O_{28}$: 1269.6479, error: 4.6 ppm) expected.

Example 10: Preparation, Purification and Characterization of CC-00540

CC-00540 was isolated from the reaction product of the bioconversion of Mogroside IIE with α-D-Xylosyl fluoride and α-xylosidase. CC-00540 was purified using multiple rounds of preparative HPLC method to provide about 3.7 mg with a purity of 95.4% (HPLC area %). A series of ID and 2D experiments was acquired on this sample: $^1H$, $^{13}C$, $^1H$-$^1H$ COSY, $^1H$-$^{13}C$ HSQC-DEPT, $^1H$-$^{13}C$ HSQC-TOCSY, and $^1H$-$^{13}C$ HMBC to elucidate the structure as mogrol-3-O-[α-D-xylopyranosyl-(1→6)β-D-glucopyranoside]-24-O-[α-D-xylopyranosyl-(1→6)-β-D-glucopyranoside]. Spectral data indicated the presence of a central triterpene core and four sugar units in the structure: two glucose units and two xylose units. The linkages between the sugar units and their attachment to the central triterpene core were determined based on COSY, TOCSY, and HSQC-DEPT data. Two glucose units exist as the β anomers while the two xylose units ($^3J$=3.1 Hz) exist in the α configuration.

TABLE 1

$^1H$ NMR (500.13 MHz, $CD_3OD$) and $^{13}C$ NMR (125 MHz) assignments of CC-00540

| Sugar | Position | $^1H$ Chemical Shift | $^{13}C$ Chemical Shift |
|---|---|---|---|
| | 1 | 2.20, 1.52 | 27.2 |
| | 2 | 1.93 | 29.3 |
| | 3 | 3.43 | 88.8 |
| | 4 | | 42.8 |
| | 5 | | 144.8 |
| | 6 | 5.49 | 119.7 |
| | 7 | 2.39 (dd), 1.81 (dd) | 25.1 |
| | 8 | 1.67 | 44.7 |
| | 9 | | 41.0 |
| | 10 | 2.48 | 37.3 |
| | 11 | 3.85 | 79.3 |
| | 12 | 1.83 | 41.0 |
| | 13 | | 48.2 |
| | 14 | | 50.5 |
| | 15 | 1.20, 1.14 | 35.4 |
| | 16 | 1.98, 1.36 | 29.1 |
| | 17 | 1.63 | 51.8 |
| | 18 | 0.92 | 17.1 |
| | 19 | 1.11 (s) | 26.2 |
| | 20 | 1.49 | 37.4 |
| | 21 | 0.97 (d) | 19.1 |
| | 22 | 1.50 | 34.1 |
| | 23 | 1.58, 1.47 | 29.8 |
| | 24 | 3.41 | 91.7 |
| | 25 | | 73.8 |
| | 26 | 1.15 (s) | 26.6 |
| | 27 | 1.16 (s) | 24.6 |
| | 28 | 1.06 (s) | 27.8 |
| | 29 | 1.20 (s) | 26.3 |
| | 30 | 0.87 (s) | 19.8 |
| Glc I | 1 | 4.32 (d), $^3J$ = 7.8 Hz | 105.6 |
| | 2 | 3.25 (t) | 75.2 |
| | 3 | 3.37 (t) | 78.1 |
| | 4 | 3.26 (t) | 72.3 |
| | 5 | 3.53 (m) | 75.8 |
| | 6 | 3.80, 3.74 | 68.0 |

TABLE 1-continued

| $^1H$ NMR (500.13 MHz, $CD_3OD$) and $^{13}C$ NMR (125 MHz) assignments of CC-00540 | | | |
|---|---|---|---|
| Sugar | Position | $^1H$ Chemical Shift | $^{13}C$ Chemical Shift |
| Glc IV | 1 | 4.29 (d), $^3J$ = 7.8 Hz | 106.3 |
| | 2 | 3.21 (t) | 75.6 |
| | 3 | 3.33 (t) | 78.4 |
| | 4 | 3.37 (t) | 71.6 |
| | 5 | 3.44 (m) | 76.2 |
| | 6 | 3.87, 3.63 | 67.8 |
| Xyl I | 1 | 4.78 (d), $^3J$ = 3.1 Hz | 100.4 |
| | 2 | 3.33 (t) | 73.9 |
| | 3 | 3.66 (t) | 75.2 |
| | 4 | 3.45 (t) | 71.8 |
| | 5 | ~3.52 | 63.1 |
| Xyl II | 1 | 4.78 (d), $^3J$ = 3.1 Hz | 100.0 |
| | 2 | 3.33 (t) | 73.9 |
| | 3 | 3.59 (t) | 75.2 |
| | 4 | 3.44 (t) | 71.6 |
| | 5 | ~3.52 | 63.0 |

Example 11: Preparation, Purification and Characterization of CC-00541

CC-00541 was isolated from the reaction product of the bioconversion of Mogroside IIE with α-D-Xylosyl fluoride and α-xylosidase. CC-00541 was purified using multiple rounds of preparative HPLC to provide about 11.1 mg with purity of 83.8% (HPLC area %) along with CC-00540 as minor compound. A series of 1D and 2D experiments was acquired on this sample: $^1H$, $^{13}C$ $^1H$-$^1H$ COSY, $^1H$-$^{13}C$ HSQC-DEPT, $^1H$-$^{13}C$ HSQC-TOCSY, and $^1H$-$^{13}C$ HMBC to elucidate the structure as mogrol-3-O-[β-D-glucopyranoside]-24-O[α-D-xylopyranosyl-(1→6)-β-D-glucopyranoside]. Spectral data indicated the presence of a central triterpene core and three sugar units in the structure: two glucose units and one xylose unit. The linkages between the sugar units and their attachment to the central triterpene core were determined based on COSY, TOCSY, and HSQC-DEPT data. Two glucose units exist as the β anomers while the remaining xylose unit ($^3J$=3.6 Hz) exists in the α configuration.

TABLE 1

| $^1H$ NMR (500.13 MHz, $CD_3OD$) and $^{13}C$ NMR (125 MHz) assignments of CC-00541 | | | |
|---|---|---|---|
| Sugar | Position | $^1H$ Chemical Shift | $^{13}C$ Chemical Shift |
| | 1 | 2.22, 1.51 | 27.2 |
| | 2 | 1.95 | 29.6 |
| | 3 | 3.42 | 88.6 |
| | 4 | | 42.9 |
| | 5 | | 144.9 |
| | 6 | 5.50 | 119.7 |
| | 7 | 2.40 (dd), 1.82 (dd) | 25.1 |
| | 8 | 1.67 | 44.7 |
| | 9 | | 40.9 |
| | 10 | 2.48 | 37.3 |
| | 11 | 3.85 | 79.4 |
| | 12 | 1.84 | 41.1 |
| | 13 | | 48.2 |
| | 14 | | 50.5 |
| | 15 | 1.20, 1.14 | 35.4 |
| | 16 | 1.99, 1.36 | 29.1 |
| | 17 | 1.64 | 51.7 |
| | 18 | 0.92 | 17.1 |
| | 19 | 1.11 (s) | 26.2 |
| | 20 | 1.48 | 37.4 |
| | 21 | 0.97 (d) | 19.1 |

TABLE 1-continued

| $^1H$ NMR (500.13 MHz, $CD_3OD$) and $^{13}C$ NMR (125 MHz) assignments of CC-00541 | | | |
|---|---|---|---|
| Sugar | Position | $^1H$ Chemical Shift | $^{13}C$ Chemical Shift |
| | 22 | 1.51 | 34.1 |
| | 23 | 1.59, 1.48 | 29.8 |
| | 24 | 3.41 | 91.7 |
| | 25 | | 73.8 |
| | 26 | 1.15 (s) | 26.6 |
| | 27 | 1.16 (s) | 24.6 |
| | 28 | 1.07 (s) | 27.8 |
| | 29 | 1.19 (s) | 26.3 |
| | 30 | 0.87 (s) | 19.8 |
| Glc I | 1 | 4.32 (d), $^3J$ = 7.9 Hz | 105.6 |
| | 2 | 3.25 (t) | 75.2 |
| | 3 | 3.37 (t) | 78.1 |
| | 4 | 3.26 (t) | 72.3 |
| | 5 | 3.53 (m) | 75.8 |
| | 6 | 3.80, 3.74 | 68.0 |
| Glc IV | 1 | 4.28 (d), $^3J$ = 7.7 Hz | 106.6 |
| | 2 | 3.19 (t) | 75.6 |
| | 3 | 3.32 (t) | 78.3 |
| | 4 | 3.28 (t) | 71.7 |
| | 5 | 3.21 (m) | 77.7 |
| | 6 | 3.82, 3.66 | 62.8 |
| Xyl | 1 | 4.78 (d), $^3J$ = 3.6 Hz | 100.0 |
| | 2 | 3.33 (t) | 73.9 |
| | 3 | 3.66 (t) | 75.2 |
| | 4 | 3.45 (t) | 71.8 |
| | 5 | 3.53, 3.52 | 63.1 |

Example 12: Preparation, Purification and Characterization of CC-00542

CC-0542 was isolated from the reaction product of the bioconversion of Mogroside IIE with α-D-Xylosyl fluoride and α-xylosidase. CC-00542 was purified using multiple rounds of preparative HPLC to provide about 6.8 mg with a purity of 84% (HPLC area %). A series of 1D and 2D experiments was acquired on this sample: $^1H$, $^{13}C$, $^1H$-$^1H$ COSY, $^1H$-$^{13}C$ HSQC-DEPT, $^1H$-$^{13}C$ TOCSY, and $^1H$-$^{13}C$ HMBC to elucidate the structure as mogrol-3-O-[α-D-xylopyranosyl-(1→6)β-D-glucopyranoside]-24-O-β-D-glucopyranoside. Spectral data indicated the presence of a central triterpene core and three sugar units: two glucose units and one xylose unit. The linkages between the sugar units and their attachment to the central triterpene core were determined based on COSY, TOCSY, and HSQC-DEPT data. Two glucose units exist as the β anomers while the remaining xylose unit ($^3J$=3.6 Hz) exists in the α configuration.

TABLE 1

| $^1H$ NMR (500.13 MHz, $CD_3OD$) and $^{13}C$ NMR (125 MHz) assignments of CC-00542 | | | |
|---|---|---|---|
| Sugar | Position | $^1H$ Chemical Shift | $^{13}C$ Chemical Shift |
| | 1 | 2.20, 1.53 | 27.2 |
| | 2 | 1.92 | 29.3 |
| | 3 | 3.43 | 88.8 |
| | 4 | | 42.8 |
| | 5 | | 144.8 |
| | 6 | 5.49 | 119.7 |
| | 7 | 2.40 (dd), 1.81 (dd) | 25.1 |
| | 8 | 1.67 | 44.7 |
| | 9 | | 41.0 |
| | 10 | 2.48 | 37.3 |
| | 11 | 3.85 | 79.4 |
| | 12 | 1.82 | 40.9 |

TABLE 1-continued $^1$H NMR (500.13 MHz, $CD_3OD$) and $^{13}$C NMR (125 MHz) assignments of CC-00542

| Sugar | Position | $^1$H Chemical Shift | $^{13}$C Chemical Shift |
|---|---|---|---|
| | 13 | | 48.2 |
| | 14 | | 50.5 |
| | 15 | 1.19, 1.14 | 35.4 |
| | 16 | 1.99, 1.35 | 29.1 |
| | 17 | 1.64 | 51.7 |
| | 18 | 0.92 | 17.1 |
| | 19 | 1.11 (s) | 26.2 |
| | 20 | 1.48 | 37.5 |
| | 21 | 0.97 (d) | 19.1 |
| | 22 | 1.49 | 34.2 |
| | 23 | 1.60, 1.49 | 29.7 |
| | 24 | 3.45 | 89.7 |
| | 25 | | 73.6 |
| | 26 | 1.15 (s) | 26.6 |
| | 27 | 1.16 (s) | 24.7 |
| | 28 | 1.07 (s) | 27.8 |
| | 29 | 1.20 (s) | 26.3 |
| | 30 | 0.87 (s) | 19.8 |
| Glc I | 1 | 4.34 (d), $^3$J = 7.8 Hz | 104.9 |
| | 2 | 3.22 (t) | 75.3 |

TABLE 1-continued $^1$H NMR (500.13 MHz, $CD_3OD$) and $^{13}$C NMR (125 MHz) assignments of CC-00542

| Sugar | Position | $^1$H Chemical Shift | $^{13}$C Chemical Shift |
|---|---|---|---|
| | 3 | 3.35 (t) | 78.0 |
| | 4 | 3.28 (t) | 71.6 |
| | 5 | 3.27 (m) | |
| | 6 | 3.85, 3.65 | 62.6 |
| Glc IV | 1 | 4.29 (d), $^3$J = 7.8 Hz | 106.3 |
| | 2 | 3.21 (t) | 75.6 |
| | 3 | 3.32 (t) | 78.4 |
| | 4 | 3.37 (t) | 71.6 |
| | 5 | 3.43 (m) | 76.3 |
| | 6 | 3.87, 3.63 | 67.8 |
| Xyl VI | 1 | 4.84 (d), $^3$J = 3.7 Hz | 100.4 |
| | 2 | 3.33 (t) | 73.9 |
| | 3 | 3.59 (t) | 75.2 |
| | 4 | 3.46 (t) | 71.6 |
| | 5 | 3.57, 3.51 | 63.0 |

Example 13: Preparation, Purification and Characterization of CC-00550

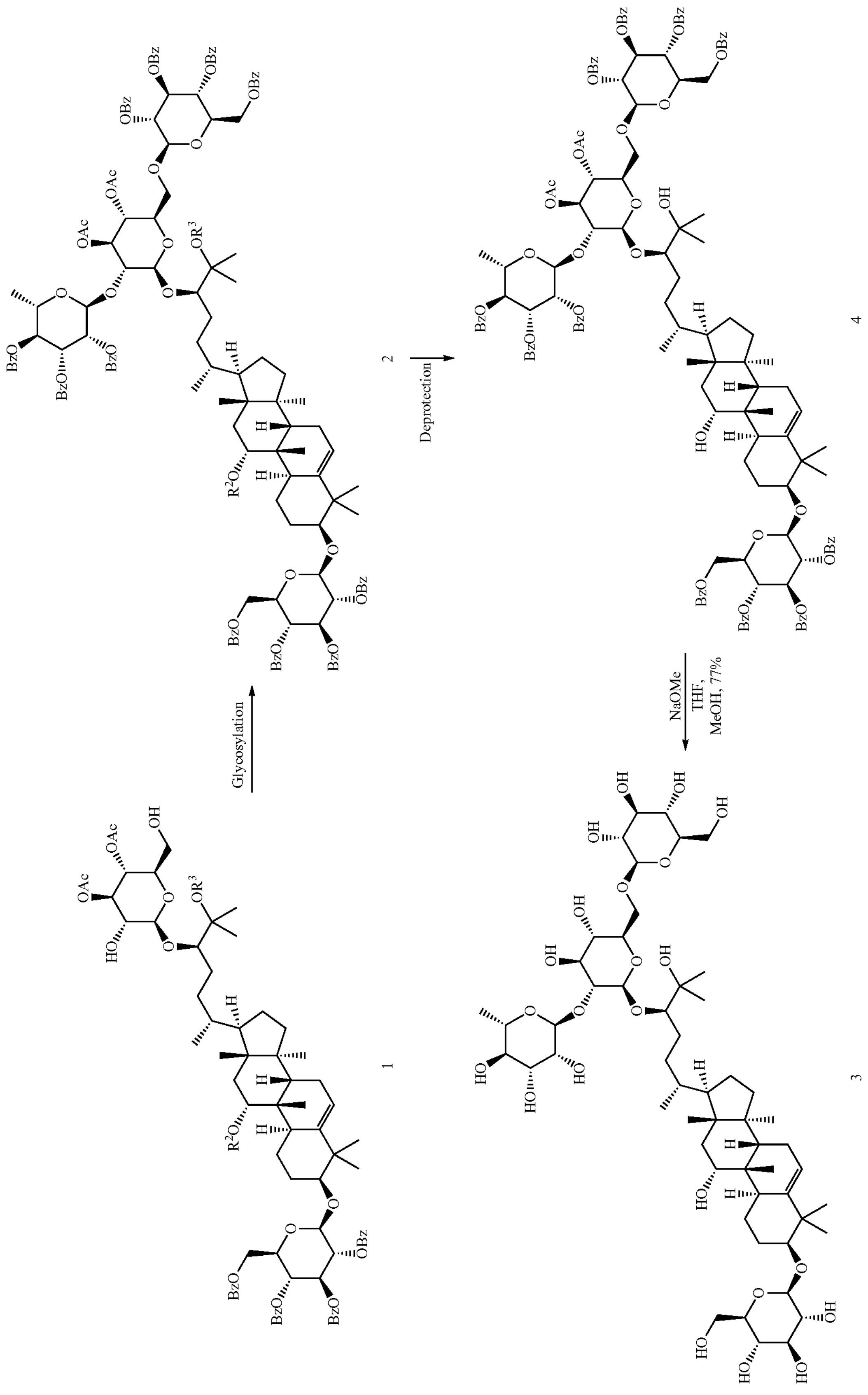
1 2 3 4

3-O-β-D-Glucopyranosyl mogrol 24-O-α-L-rhamnopyranosyl-(1→2)-β-D-glucopyranosyl-(1→6)-β-D-glucopyranoside (4). To a solution of 3 (613.8 mg, 0.2625 mmol) in dry THF (11 mL) and dry MeOH (11 mL) was added dropwise 0.5 M solution of NaOMe in MeOH (0.52 mL, 0.2625 mmol) at room temperature under $N_2$ atmosphere. The mixture was stirred at the same temperature for 18 h, neutralized with a 10% AcOH aqueous solution and concentrated under reduced pressure. The residual white solid was purified by preparative HPLC (Phenomenex Luna C18 (2) column, 21.2×250 mm, 5 μm particles, 25% $CH_3CN$ in $H_2O$, 20 mL/min, $t_R$=10.2 min). The combined fractions were concentrated under reduced pressure and the residue was dried under vacuum to give the title compound 4 (225.5 mg, 77%) as a white powder. $R_f$=0.68 (silica gel, $CH_2Cl_2$/MeOH/$H_2O$=5:4:1). $^1H$ NMR (500 MHz, pyridine-$d_5$) δ 7.68 (br s, 1H), 7.50 (br s, 1H), 7.21-6.87 (m, 4H), 6.63 (br s, 2H), 6.55 (br s, 1H), 6.42 (s, 1H), 6.36 (br s, 1H), 6.20 (br s, 1H), 5.73 (s, 1H), 5.67 (br s, 1H), 5.52 (d, J=5.7 Hz, 1H), 5.02 (d, J=7.8 Hz, 1H), 4.92 (d, J=7.8 Hz, 2H), 4.87-4.82 (m, 1H), 4.82-4.74 (m, 2H), 4.62 (dd, J=9.2, 3.3 Hz, 1H), 4.58-4.47 (m, 2H), 4.45-4.34 (m, 2H), 4.34-4.27 (m, 2H), 4.27-4.19 (m, 5H), 4.19-4.14 (m, 1H), 4.14-4.08 (m, 1H), 4.08-4.01 (m, 2H), 4.01-3.87 (m, 5H), 3.70 (s, 1H), 3.01-2.89 (m, 1H), 2.84-2.72 (m, 1H), 2.53-2.41 (m, 1H), 2.39-2.26 (m, 1H), 2.21-1.92 (m, 7H), 1.72 (d, J=6.2 Hz, 3H), 1.73-1.65 (m, 3H), 1.63 (d, J=7.5 Hz, 1H), 1.59 (s, 3H), 1.60-1.53 (m, 2H), 1.53-1.43 (m, 1H), 1.49 (s, 3H), 1.38 (s, 3H), 1.33 (s, 3H), 1.15 (s, 3H), 1.13-1.05 (m, 1H), 1.09 (d, J=4.3 Hz, 3H), 1.05-0.96 (m, 1H), 0.89 (s, 3H), 0.81 (s, 3H). $^{13}C$ NMR (125 MHz, pyridine-$d_5$) δ 144.7, 118.9, 107.9, 105.3, 103.9, 102.7, 90.0, 88.4, 79.9, 79.2, 79.0, 78.7, 78.6, 78.2, 77.1, 77.0, 76.0, 75.8, 74.5, 73.1, 73.0, 72.8 (2C), 72.2, 71.9, 70.4, 69.9, 63.5, 63.0, 52.0, 50.1, 47.9, 43.9, 42.9, 41.6, 40.6, 37.3, 36.5, 34.9, 33.4, 30.1, 30.0, 29.2, 28.2, 27.5, 27.3, 26.9, 26.7, 25.12, 25.06, 19.7, 19.3, 19.1, 17.6.

Example 14: Preparation, Purification and Characterization of CC-00551

CC-00551 was isolated from monk fruit (Luo Han Guo) extract containing 90% Mogroside V. The 1D and 2D NMR and MS spectral analysis of CC-00551 allowed a full assignment of its structure as mogrol-3-O-[{β-D-glucopyranosyl-(1→6)}-β-D-glucopyranoside]-24-O-[{β-D-glucopyranosyl-(1→2)}-{β-D-xylopyranosyl-(16)}-β-D-glucopyranoside]. The assignments for the central triterpene core was done by a combination of 1H, 13C, 1H-1H COSY, 1H-13C HSQC-DEPT and 1H-13C HMBC data whereas a series of 1D-TOCSY experiments in combination with 1D and 2D NMR data was used for the assignment and linkage of sugar units. Evaluation of NMR data led to the conclusion that this compound bears four glucose units and one xylose unit. The xylose unit is linked to GlcI by a 1→6 sugar linkage.

The ESI-TOF mass spectrum acquired by infusing a sample of CC-00551 showed a $[M-H]^-$ ion at m/z 1255.6377. The mass of the $[M-H]^-$ ion was in good agreement with the molecular formula $C_{59}H_{100}O_{28}$ (calcd for $C_{59}H_{99}O_{28}$: 1255.6323, error: 4.3 ppm) expected. The MS data confirmed a nominal mass of 1256 Daltons with the molecular formula, $C_{59}H_{100}O_{28}$. The ions observed at m/z 1291.5961 and 1353.5873 are most likely due to [M-H+HCl]− and [M-H+H3PO4]−, respectively. The MS/MS spectrum, selecting the [M-H]− ion at m/z 1255.6 for fragmentation, indicated loss of xylose unit at m/z 1123.5693 followed by sequential loss of four glucose units at m/z 961.5647, 799.5051, 637.4304 and 475.3798 indicated presence of one xylose and four glucose units in the structure.

TABLE 1

$^1H$ and $^{13}C$ NMR (500 and 125 MHz, $CD_3OD$), assignments of the CC-00551 aglycone.

| Position | $^{13}C$ | $^1H$ |
|---|---|---|
| 1 | 27.2 | 1.48 m |
| | | 2.22 m |
| 2 | 29.6 | 1.91 m |
| | | 1.95 m |
| 3 | 88.2 | 3.45 m |
| 4 | 42.9 | — |
| 5 | 145.1 | — |
| 6 | 119.6 | 5.48 brd (5.9) |
| 7 | 25.1 | 1.81 m |
| | | 2.38 m |
| 8 | 44.7 | 1.66 m |
| 9 | 40.9 | — |
| 10 | 37.2 | 2.49 brd (12.4) |
| 11 | 79.4 | 3.84 m |
| 12 | 41.1 | 1.81 m |
| | | 1.87 m |
| 13 | 48.3 | — |
| 14 | 50.6 | — |
| 15 | 35.4 | 1.13 m |
| | | 1.21 m |
| 16 | 29.4 | 1.33 m |
| | | 1.98 m |
| 17 | 51.8 | 1.62 m |
| 18 | 17.1 | 0.91 s |
| 19 | 26.2 or 26.3 | 1.10 s |
| 20 | 37.5 | 1.44 m |
| 21 | 19.3 | 0.97 d (6.3) |
| 22 | 34.2 | 1.48 m |
| | | 1.56 m |
| 23 | 29.8 | 1.40 m |
| | | 1.54 m |
| 24 | 93.2 | 3.39 m |
| 25 | 73.9 | — |
| 26 | 26.8† | 1.11 s† |
| 27 | 24.3† | 1.14 s† |
| 28 | 28.0 | 1.07 s |
| 29 | 26.2 or 26.3 | 1.18 s |
| 30 | 20.0 | 0.88 s |

†Assignments can be interchanged.

TABLE 2

$^1H$ and $^{13}C$ NMR (500 and 125 MHz, $CD_3OD$), assignments of the CC-00551 C-3 glycoside.

| Position | $^{13}C$ | $^1H$ |
|---|---|---|
| $Glc_{IV}$-1 | 106.4 | 4.28 d (7.8) |
| $Glc_{IV}$-2 | 75.6 | 3.19 m |
| $Glc_{IV}$-3 | 77.9-78.2§ | ~3.31 m |
| $Glc_{IV}$-4 | 71.6-71.9λ | ~3.30 m |
| $Glc_{IV}$-5 | 77.2 | 3.40 m |
| $Glc_{IV}$-6 | 69.8 | 3.80 m, 4.05 brdd (10.3Ψ) |
| $Glc_V$-1 | 104.8 | 4.42 d (7.8) |
| $Glc_V$-2 | 75.1 or 75.2 | 3.18 m |
| $Glc_V$-3 | 77.9-78.2§ | 3.35 m |
| $Glc_V$-4 | 71.6-71.9λ | 3.28 m |
| $Glc_V$-5 | 77.9-78.2§ | ~3.26 m |
| $Glc_V$-6 | 62.7 | 3.66 m, 3.85 m |

§Five carbon resonances in the range of 77.9-78.2 ppm (77.93, 77.98, 78.06, 78.14 and 78.19 ppm), hence chemical shifts could not be unequivocally assigned.

λThree carbon resonances in the range of 71.6-71.9 ppm (71.59, 71.65 and 71.88 ppm), hence chemical shifts could not be unequivocally assigned.

ΨSignal not resolved completely, thus smaller coupling could not be confirmed.

TABLE 3

$^{1}H$ and $^{13}C$ NMR (500 and 125 MHz, $CD_3OD$), assignments of the CC-00551 C-24 glycoside.

| Position | $^{13}C$ | $^{1}H$ |
|---|---|---|
| Glc$_{I}$-1 | 104.1 | 4.43 d (7.3) |
| Glc$_{I}$-2 | 81.3 | 3.61 m |
| Glc$_{I}$-3 | 78.8 | 3.58 m |
| Glc$_{I}$-4 | 71.6-71.9[λ] | ~3.28 m |
| Glc$_{I}$-5 | 76.5 | 3.51 m |
| Glc$_{I}$-6 | 70.5 | 3.51 m, 4.21[€] |
| Glc$_{III}$-1 | 104.5 | 4.77 d (7.8) |
| Glc$_{III}$-2 | 75.7 | 3.27 m |
| Glc$_{III}$-3 | 77.9-78.2[§] | 3.36 m |
| Glc$_{III}$-4 | 72.3 | 3.21 m |
| Glc$_{III}$-5 | 77.9-78.2[§] | ~3.27 m |
| Glc$_{III}$-6 | 63.5 | 3.63 m, 3.86 m |
| Xyl-1 | 105.4 | 4.22 d (7.4) |
| Xyl-2 | 75.1 or 75.2 | 3.19 m |
| Xyl-3 | 77.5 | 3.31 m |
| Xyl-4 | 71.2 | 3.47 m |
| Xyl-5 | 66.9 | 3.18 m, 3.84 m |

§Five carbon resonances in the range of 77.9-78.2 ppm (77.93, 77.98, 78.06, 78.14 and 78.19 ppm), hence chemical shifts could not be unequivocally assigned.
λThree carbon resonances in the range of 71.6-71.9 ppm (71.59, 71.65 and 71.88 ppm), hence chemical shifts could not be unequivocally assigned.
€Resonance partially overlapped with xylose anomeric proton. So, multiplicity could not be assigned.

Example 15: Sensory Analysis

The following samples were tested at 400 ppm in water at 4° C. The sample amount was limited. As such, the number of panelists per sample was 1-10 and the volume tested was 2-10 mL. The sweetness of each sample was compared to sucrose references.

| Compound | Sweetness (SE) |
|---|---|
| CC-00489 | >9 SE |
| CC-00491 | >10 |
| CC-00500 | >5 |
| CC-00518 | >9 |
| CC-00520 | >7 |
| CC-00539 | >3 |
| CC-00540 | >2 |
| CC-00541 | >1 |
| CC-00542 | >2 |

Example 16: Preparation of Cc-00497

CC-00497 was prepared by bioconversion of isomogroside V. 250 mg of isomogroside V and 10 mg of beta-galactosidase G5160 in 3.1 mL of pH 5 sodium acetate buffer was stirred at 37° C. for 3 days and heated for 30 minutes. The crude mixture was directly purified using preparative HPLC to provide 2.8 mg of CC-00497. The structure was confirmed by 1D and 2D NMR analysis.

TABLE 1

$^{1}H$ and $^{13}C$ NMR (500 and 125 MHz, $CD_3OD$), assignments of the CC-00497 aglycone.

| | CC-00497 | |
|---|---|---|
| Position | $^{13}C$ | $^{1}H$ |
| 1 | 27.2 | 1.48 m |
| | | 2.22 m |
| 2 | 29.6 | 1.90 m |
| | | 1.93 m |
| 3 | 88.2 | 3.45 m |
| 4 | 42.8 | — |
| 5 | 145.0 | — |
| 6 | 119.7 | 5.48 brd (5.7) |
| 7 | 25.1 | 1.80 m |
| | | 2.38 m |
| 8 | 44.6 | 1.66 m |
| 9 | 40.9 | — |
| 10 | 37.3[§] | 2.47 brd (12.1) |
| 11 | 79.4 | 3.84 m |
| 12 | 41.1 | 1.80 m |
| | | 1.83 m |
| 13 | 48.2 | — |
| 14 | 50.5 | — |
| 15 | 35.4 | 1.12 m |
| | | 1.18 m |
| 16 | 29.0 | 1.34 m |
| | | 1.96 m |
| 17 | 51.8 | 1.60 m |
| 18 | 17.1 | 0.91 s |
| 19 | 26.2[¥] | 1.10 s[Å] |
| 20 | 37.3[§] | 1.46 m |
| 21 | 19.0 | 0.95 brd (4.9) |
| 22 | 34.0 | 1.47 m |
| | | 1.51 m |
| 23 | 30.0 | 1.41 m |
| | | 1.52 m |
| 24 | 92.7 | 3.38 m |
| 25 | 73.8 | — |
| 26 | 26.8[†] | 1.11 s[†, Å] |
| 27 | 24.2[†] | 1.12 s[†] |
| 28 | 27.8 | 1.06 s |
| 29 | 26.2[¥] | 1.18 s |
| 30 | 19.8 | 0.86 s |

†Assignments can be interchanged.
§Two carbon resonances at 37.3 ppm (37.25 and 37.31 ppm), hence chemical shifts could not be unequivocally assigned.
¥Two carbon resonances at 26.2 ppm (26.20 and 26.23 ppm), hence chemical shifts could not be unequivocally assigned.
ÅPartially overlapped methyl resonances.

TABLE 2

$^{1}H$ and $^{13}C$ NMR (500 and 125 MHz, $CD_3OD$), assignments of the CC-00497 C-3 glycoside.

| | CC-00497 | |
|---|---|---|
| Position | $^{13}C$ | $^{1}H$ |
| Glc$_{IV}$-1 | 106.3 | 4.28 d (7.5) |
| Glc$_{IV}$-2 | 75.1-75.5[€] | 3.19 m |
| Glc$_{IV}$-3 | 77.9-78.1[§] | 3.30 m |
| Glc$_{IV}$-4 | 71.6[λ] | 3.32 m |
| Glc$_{IV}$-5 | 77.2 | 3.40 m |
| Glc$_{IV}$-6 | 69.8 | 3.80 m, 4.05 m |
| Glc$_{V}$-1 | 104.8 | 4.42 d (7.8) |
| Glc$_{V}$-2 | 75.1-75.5[€] | 3.19 m |
| Glc$_{V}$-3 | 77.9-78.1[§] | 3.36 m |
| Glc$_{V}$-4 | 71.6[λ] | 3.29 m |
| Glc$_{V}$-5 | 77.9-78.1[§] | 3.26 m |
| Glc$_{V}$-6 | 62.7 | 3.66 m, 3.85 m |

€Four carbon resonances in the range of 75.1-75.5 ppm (75.12, 75.15, 75.18 and 75.54 ppm), hence chemical shifts could not be unequivocally assigned.
§Four carbon resonances in the range of 77.9-78.1 ppm (77.89, 77.95, 78.04 and 78.08 ppm), hence chemical shifts could not be unequivocally assigned.
λTwo carbon resonances at 71.6 ppm (71.57 and 71.62 ppm), hence chemical shifts could not be unequivocally assigned.

TABLE 3

| $^{1}H$ and $^{13}C$ NMR (500 and 125 MHz, $CD_3OD$), assignments of the CC-00497 C-24 glycoside. | | |
|---|---|---|
| | CC-00497 | |
| Position | $^{13}C$ | $^{1}H$ |
| $Glc_I$-1 | 105.8 | 4.29 d (~7.5£) |
| $Glc_I$-2 | 75.1-75.5€ | 3.25 m |
| $Glc_I$-3 | 77.9-78.1§ | 3.36 m |
| $Glc_I$-4 | 72.2 | 3.23 m |
| $Glc_I$-5 | 76.5 | 3.50 m |
| $Glc_I$-6 | 70.6 | 3.51 m, 4.20 m |
| Xyl-1 | 105.4 | 4.21 d (7.5) |
| Xyl-2 | 75.1-75.5€ | 3.20 m |
| Xyl-3 | 77.4 | 3.32 m |
| Xyl-4 | 71.2 | 3.47 m |
| Xyl-5 | 66.9 | 3.18 m, 3.84 m |

€Four carbon resonances in the range of 75.1-75.5 ppm (75.12, 75.15, 75.18 and 75.54 ppm), hence chemical shifts could not be unequivocally assigned.

§Four carbon resonances in the range of 77.9-78.1 ppm (77.89, 77.95, 78.04 and 78.08 ppm), hence chemical shifts could not be unequivocally assigned.

£The coupling constant could not assigned unequivocally due to partial overlap of $Glc_I$ H-1 at 4.29 ppm with $Glc_{IV}$ H-1 at 4.28 ppm and impurity.

The invention claimed is:

1. A mogroside selected from the group consisting of:

CC-00489

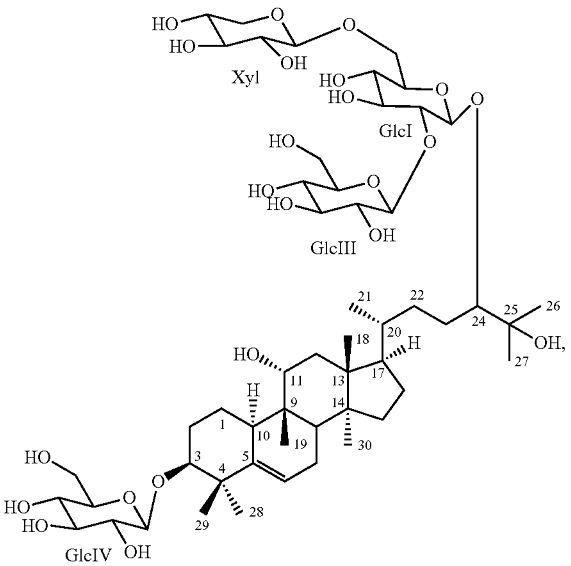

CC-00491

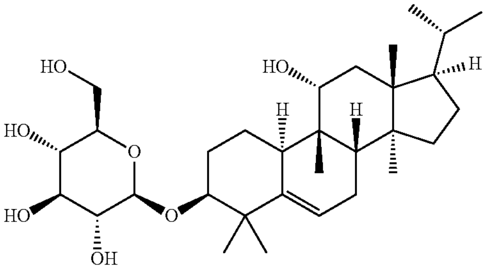

-continued

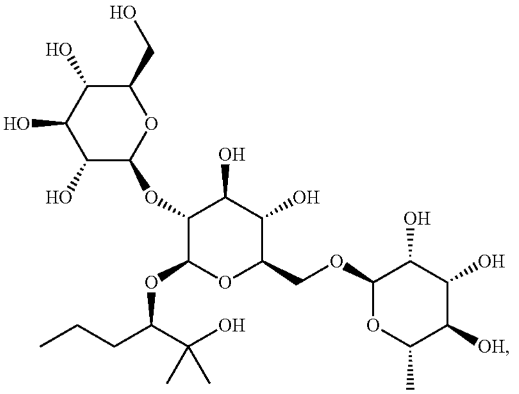

CC-00497

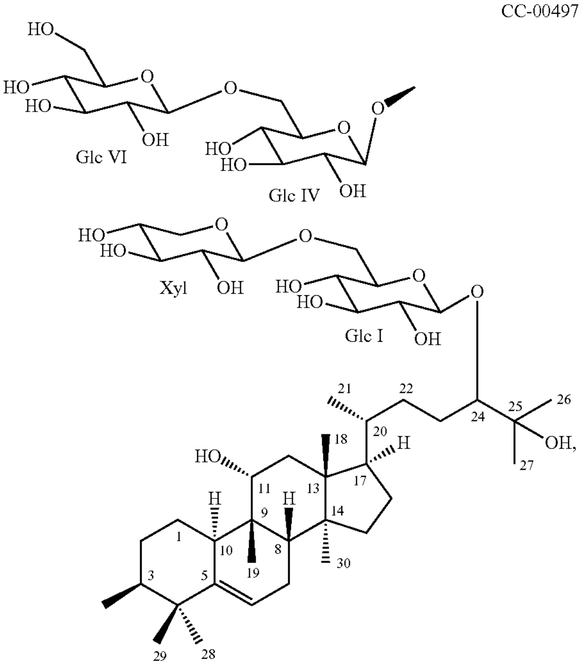

CC-00498

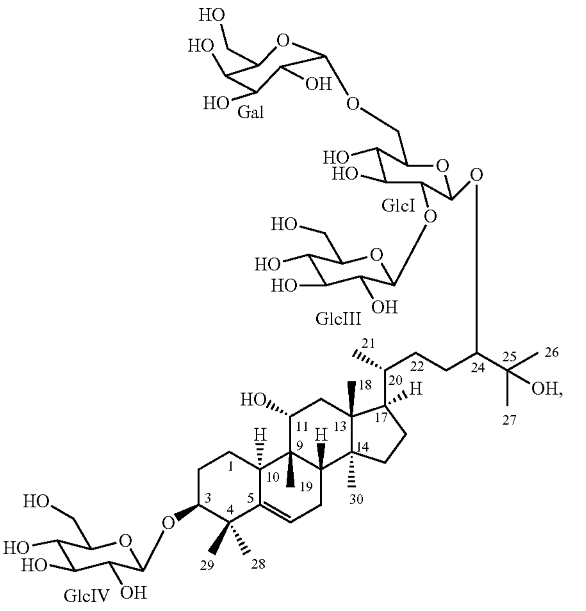

-continued
CC-00500
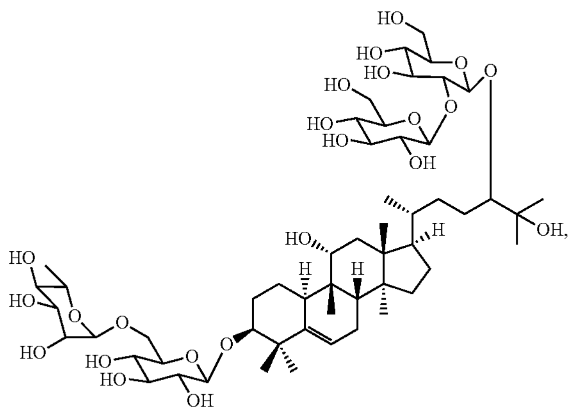
CC-00518
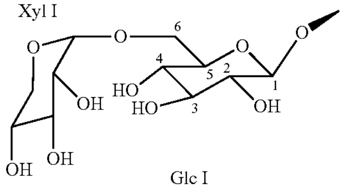
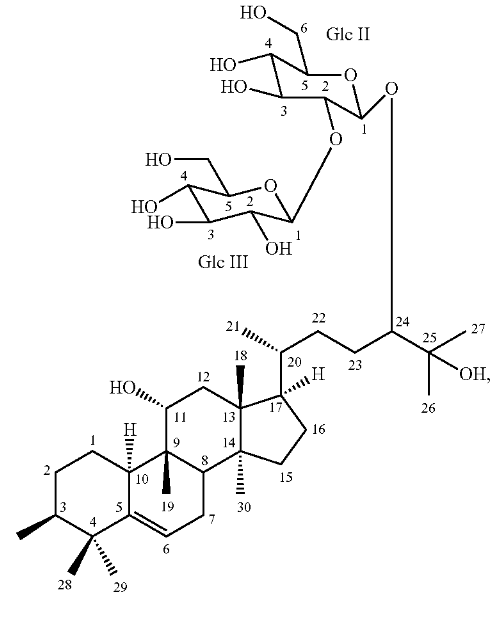
CC-00540
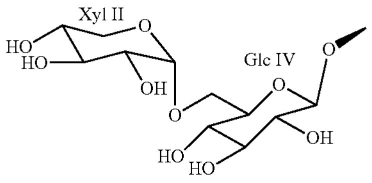
-continued
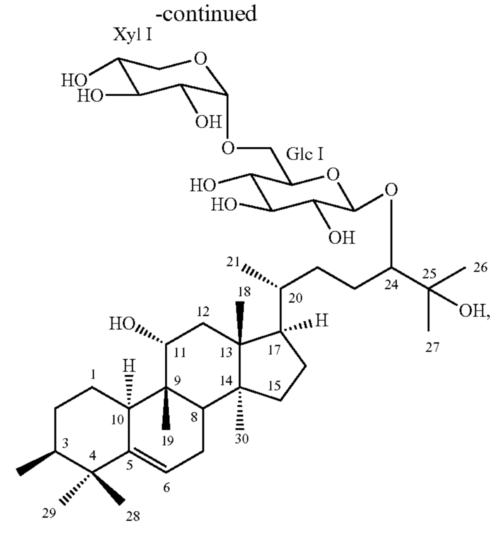
CC-00541
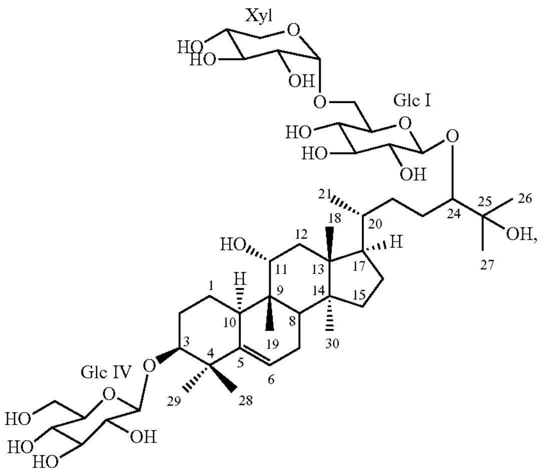
and
CC-00542
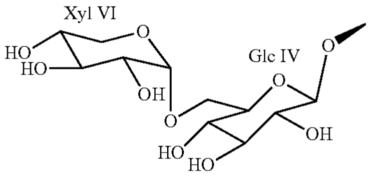
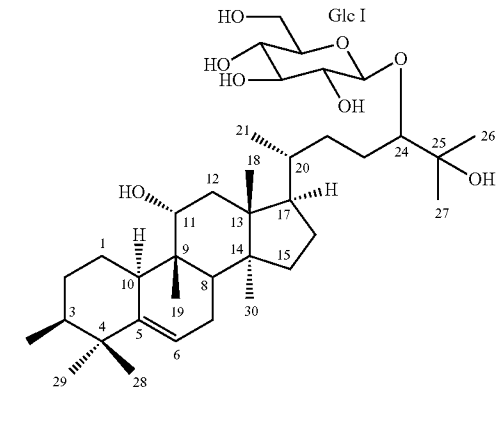
wherein the mogroside is isolated and purified.

2. A composition comprising a mogroside of claim 1 and at least one other substance, wherein the composition comprises at least about 5% of the mogroside of claim 1 by weight.

3. A consumable comprising a mogroside of claim 1.

4. The consumable of claim 3, wherein the consumable is a beverage or beverage product.

5. The consumable of claim 4, wherein the beverage comprises said mogroside in a concentration from about 10 ppm to about 1,000 ppm or about 1 ppm to about 100 ppm.

6. The consumable of claim 4, wherein the beverage further comprises at least one additional sweetener selected from the group consisting of a carbohydrate sweetener, a rare sugar sweetener, a high potency sweetener, a synthetic sweetener and combinations thereof.

7. The consumable of claim 4, wherein the beverage further comprises at least one additional sweetener selected from the group consisting of rebaudioside A, rebaudioside M, rebaudioside D, mogroside V, siamenoside I and mogrol-3-O-[β-D-glucopyranoside]-24-O-{[β-D-glucopyranosyl-(1→2)]-[α-D-glucopyranosyl-(1→6)]-β-D-glucopyranoside}.

8. The consumable of claim 4, wherein the beverage further comprises at least one functional ingredient selected from the group consisting of saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

9. The consumable of claim 4, wherein the beverage further comprises at least one additive selected from the group consisting of carbohydrates, polyols, amino acids, salts of amino acids, poly-amino acids, salts of poly-amino acids, sugar acids, salts of sugar acids, nucleotides, organic acids, inorganic acids, organic acid salt, organic base salt, inorganic salts, bitter compounds, caffeine, flavorants, flavoring ingredients, astringent compounds, proteins, protein hydrolysates, surfactants, emulsifiers, plant extracts, flavonoids, alcohols, polymers and combinations thereof.

10. The consumable of claim 4, wherein the beverage is selected from the group consisting of frozen carbonated beverages, enhanced sparkling beverages, cola, fruit-flavored sparkling beverages, ginger-ale, soft drinks, root beer, fruit juice, fruit-flavored juice, juice drinks, nectars, vegetable juice, vegetable-flavored juice, sports drinks, energy drinks, enhanced water drinks, enhanced water with vitamins, near water drinks, coconut water, tea type drinks, coffee, cocoa drink, beverage containing milk components, beverages containing cereal extracts, protein drinks, drinkable yogurt, and smoothies.

11. The consumable of claim 4, wherein the beverage is a beverage that has up to 40 calories per eight ounce serving or a beverage that has up to 60 calories per eight ounce serving.

* * * * *